United States Patent
Morgans, Jr. et al.

(10) Patent No.: US 10,696,672 B2
(45) Date of Patent: Jun. 30, 2020

(54) AMINO ACID COMPOUNDS AND METHODS OF USE

(71) Applicant: Pliant Therapeutics, Inc., South San Francisco, CA (US)

(72) Inventors: David John Morgans, Jr., Los Altos, CA (US); Randall L. Halcomb, Foster City, CA (US); Gustave Bergnes, Pacifica, CA (US); Hui Li, Santa Clara, CA (US); Lan Jiang, Foster City, CA (US); Jacob Cha, San Bruno, CA (US); Timothy Hom, Sunnyvale, CA (US)

(73) Assignee: Pliant Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/471,521

(22) PCT Filed: Dec. 20, 2017

(86) PCT No.: PCT/US2017/067622
§ 371 (c)(1),
(2) Date: Jun. 19, 2019

(87) PCT Pub. No.: WO2018/119087
PCT Pub. Date: Jun. 28, 2018

(65) Prior Publication Data
US 2019/0322663 A1    Oct. 24, 2019

Related U.S. Application Data

(60) Provisional application No. 62/438,951, filed on Dec. 23, 2016, provisional application No. 62/538,564, filed on Jul. 28, 2017.

(51) Int. Cl.
*A61K 31/415* (2006.01)
*C07D 471/04* (2006.01)
*C07C 53/00* (2006.01)

(52) U.S. Cl.
CPC .................. *C07D 471/04* (2013.01)

(58) Field of Classification Search
CPC ........ C07D 471/04; C07C 53/00; A61K 45/06
See application file for complete search history.

(56) References Cited

U.S. PATENT DOCUMENTS

| | | |
|---|---|---|
| 10,131,658 B2 | 11/2018 | Degrado |
| 10,214,522 B2 | 2/2019 | Degrado |
| 2004/0092454 A1 | 5/2004 | Schadt |
| 2008/0045521 A1 | 2/2008 | Arnould |
| 2009/0104116 A1 | 4/2009 | Zischinsky et al. |
| 2016/0264566 A1 | 9/2016 | Degrado |
| 2016/0280705 A1 | 9/2016 | Anderson |
| 2016/0376266 A1 | 12/2016 | Degrado |
| 2018/0093984 A1 | 4/2018 | Jiang |
| 2018/0244648 A1 | 8/2018 | Harrison |
| 2019/0276449 A1 | 9/2019 | Cha |

FOREIGN PATENT DOCUMENTS

| | | |
|---|---|---|
| WO | WO2016046226 A1 | 3/2016 |
| WO | WO2016145258 A1 | 9/2016 |
| WO | WO2018049068 A1 | 3/2018 |
| WO | WO2019173653 A1 | 9/2019 |
| WO | WO2020006315 A1 | 1/2020 |

OTHER PUBLICATIONS

International Preliminary Report on Patentability dated Jun. 25, 2019 for PCT Application No. PCT/US2017/067622 filed on Dec. 20, 2017, 5 pages.
International Search Report and Written Opinion dated Mar. 8, 2018 for PCT Application No. PCT/US2017/067622 filed on Dec. 20, 2017, 7 pages.
U.S. Appl. No. 16/455,490, Leftheris et al., filed Jun. 27, 2019. (Copy not submitted herewith pursuant to the waiver of 37 C.F.R. § 1.98(a)(2)(iii) issued by the Office on Sep. 21, 2004).

*Primary Examiner* — John M Mauro
(74) *Attorney, Agent, or Firm* — Morrison & Foerster LLP

(57) ABSTRACT

The invention relates to compounds of formula (I): formula (I) or a salt thereof wherein $R^1$, $R^5$, $R^7$, $R^8$, X, m, n, p and q are as described herein. Compounds of formula (I) and pharmaceutical compositions thereof are αvβ6 integrin inhibitors that are useful for treating tissue specific fibrosis such as idiopathic pulmonary fibrosis (IPF) and nonspecific interstitial pneumonia (NSIP).

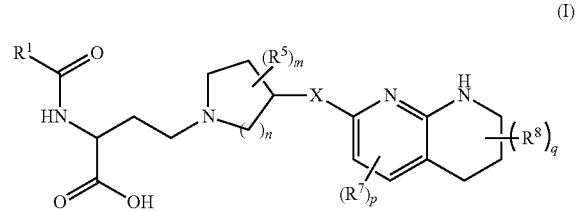

(I)

34 Claims, No Drawings

AMINO ACID COMPOUNDS AND METHODS OF USE

CROSS-REFERENCE TO RELATED APPLICATIONS

This application is a National Phase filing under 35 U.S.C. § 371 of International Application No. PCT/US2017/067622 having an International Filing Date of Dec. 20, 2017, which claims priority benefit of U.S. Provisional Patent Application No. 62/438,951 filed Dec. 23, 2016, and of U.S. Provisional Patent Application No. 62/538,564 filed Jul. 28, 2017. The entire contents of those applications are hereby incorporated by reference herein.

TECHNICAL FIELD OF THE INVENTION

This invention relates to amino acid compounds, pharmaceutical compositions comprising the amino acid compounds, and methods of use of the compounds and compositions in treating diseases, such as fibrotic diseases.

BACKGROUND OF THE INVENTION

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. http://my.clevelandclinic.org/health/diseases_conditions/hic_Pneumonia/hic-nonspecific-interstitial-pneumonia.

Available courses of treatment are scarce, as there are currently no options on the market proven to have an effect on long-term patient survival or symptomatology. There remains a need for treatment of fibrotic diseases.

The $\alpha v \beta 6$ integrin is expressed in epithelial cells, and binds to the latency-associated peptide of transforming growth factor-$\beta 1$ (TGF$\beta 1$) and mediates TGF$\beta 1$ activation. Its expression level is significantly increased after injury to lung and cholangiocytes, and plays a critical in vivo role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of $\alpha v \beta 6$ is elevated in liver and bile duct of PSC patients.

The present disclosure provides for $\alpha v \beta 6$ integrin inhibitors that may be useful for tissue-specific treatment of fibrosis.

BRIEF SUMMARY OF THE INVENTION

Disclosed are amino acid compounds that are $\alpha v \beta 6$ integrin inhibitors, compositions containing these compounds and methods for treating diseases mediated by $\alpha v \beta 6$ integrin such as a fibrotic disease.

In one aspect, provided is a compound of formula (I), or any variation thereof, or a salt thereof (e.g., a pharmaceutically acceptable salt thereof), as detailed herein. Also provided is a compound of (I-A), or any variation thereof, or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient. Also provided is a pharmaceutical composition comprising a compound of formula (I-A), or any variation thereof detailed herein, or a salt thereof (e.g., a pharmaceutically acceptable salt thereof), and a pharmaceutically acceptable carrier or excipient.

In another aspect, provided is a method of treating a fibrotic disease in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease is pulmonary fibrosis, liver fibrosis, skin fibrosis, cardiac fibrosis, kidney fibrosis, gastrointestinal fibrosis, primary sclerosing cholangitis, or biliary fibrosis. A compound of formula (I-A), or any variation thereof, or a salt thereof (e.g., a pharmaceutically acceptable salt thereof), as detailed herein may also be used in any of the methods detailed herein, such as in a method of delaying the onset and/or development of a fibrotic disease in an individual (such as a human) who is at risk for developing a fibrotic disease.

In another aspect, provided is a method of delaying the onset and/or development of a fibrotic disease in an individual (such as a human) who is at risk for developing a fibrotic disease.

Also provided is a compound of formula (I), or any variation thereof detailed herein, or a pharmaceutical composition thereof, for the treatment of a fibrotic disease.

Also provided is use of a compound of formula (I), or any variation thereof detailed herein, or a pharmaceutically acceptable salt thereof, in the manufacture of a medicament for the treatment of a fibrotic disease. Also provided is use of a compound of formula (I-A), or any variation thereof detailed herein, or a pharmaceutically acceptable salt thereof, in the manufacture of a medicament for the treatment of a fibrotic disease.

Further provided is a kit comprising a compound of formula (I), or any variation thereof detailed herein, or a pharmaceutically acceptable salt thereof. Further provided is a kit comprising a compound of formula (I-A), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (I) or any variation thereof. Also provided is a method of making a compound of formula (I-A) or any variation thereof. Also provided are compound intermediates useful in synthesis of a compound of formula (I) or (I-A), or any variation thereof.

DETAILED DESCRIPTION OF THE INVENTION

The invention provides, inter alia, compounds of formula (I), and variations thereof, pharmaceutical compositions comprising compounds of formula (I), and methods of using such compounds and compositions in treating fibrotic diseases. Also provided are compounds of formula (I-A), and variations thereof, pharmaceutical compositions comprising compounds of formula (I-A), and methods of using such compounds and compositions in treating fibrotic diseases.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms).

Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_0$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, for example, pent-1-enyl, pent-2-enyl, hex-1-enyl, hex-2-enyl, hex-3-enyl, and the like.

"Alkenylene" as used herein refers to the same residues as alkenyl, but having bivalency. Particular alkylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH_2—), 1,4-but-1-enylene (—CH=CH—$CH_2CH_2$—), 1,4-but-2-enylene (—$CH_2$CH=CH$CH_2$—), 1,6-hex-1-enylene (—CH=CH—$(CH_2)_3CH_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

"Alkynylene" as used herein refers to the same residues as alkynyl, but having bivalency. Particular alkylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C═C) and having the number of carbon atoms designated (i.e., $C_2$-$C_{10}$ means two to ten carbon atoms). Cycloalkenyl can consist of one ring, such as cyclohexyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof. In fused ring systems, one or more of the fused rings can be cycloalkyl, aryl or heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl ($-CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($-OCF_3$).

"Carbonyl" refers to the group C=O.

"Thiocarbonyl" refers to the group C=S.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this invention, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier.

Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Compounds

In one aspect, provided is a compound of formula (I):

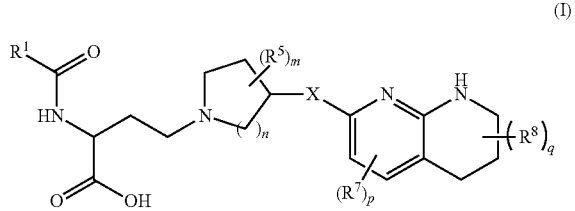

(I)

or a salt thereof, wherein:

$R^1$ is $C_1$-$C_6$ alkyl, $C_3$-$C_8$ cycloalkyl, $C_6$-$C_{14}$ aryl, 5- to 10-membered heteroaryl, 3- to 12-membered heterocyclyl, —$OR^2$ or —$NR^{3a}R^{3b}$, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^1$ are independently optionally substituted by $R^{10}$;

$R^2$ is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^2$ are independently optionally substituted by $R^{10}$;

$R^{3a}$ and $R^{3b}$ are independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{3a}$ and $R^{3b}$ are independently optionally substituted by $R^{10}$;

or $R^{3a}$ and $R^{3b}$ are taken together with the nitrogen to which they are attached to form a 4- to 8-membered heterocyclyl optionally substituted by $R^{10}$;

n is 1 or 2;

m is 0 to 6;

each $R^5$, where present, is independently $C_1$-$C_6$ alkyl, $C_3$-$C_6$ cycloalkyl, halogen, —CN, —$OR^{5a}$, —$C(O)OR^{5a}$, —$NR^{5a}C(O)R^{5b}$; —$NR^{5c}R^{5d}$, —$C(O)NR^{5c}R^{5d}$, —$SO_2R^{5c}$, or —$SO_2NR^{5c}R^{5d}$, wherein the $C_1$-$C_6$ alkyl and $C_3$-$C_6$ cycloalkyl are independently optionally substituted by $R^{10}$;

each $R^{5a}$ and $R^{5b}$ is independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5a}$ and $R^{5b}$ are independently optionally substituted by $R^{10}$;

each $R^{5c}$ and $R^{5d}$ is independently hydrogen, $C_1$-$C_6$ alkyl, $C_3$-$C_8$ cycloalkyl, $C_6$-$C_4$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5c}$ and $R^{5d}$ are independently optionally substituted by $R^{10}$;

or $R^{5c}$ and $R^{5d}$ are taken together with the nitrogen to which they are attached to form a 4- to 8-membered heterocyclyl optionally substituted by $R^{10}$;

each $R^{5e}$ is independently $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5e}$ are independently optionally substituted by $R^{10}$;

X is $C_1$-$C_3$ alkylene optionally substituted by $R^{10}$;

p is 0 to 2;

q is 0 to 6;

each $R^7$, where present, is independently $C_1$-$C_6$ alkyl optionally substituted by halogen or —OH, $C_3$-$C_6$ cycloalkyl, halogen, —CN, —$NO_2$, —$OR^{7a}$, or —$NR^{7b}R^{7c}$;

each $R^{7a}$, $R^{7b}$ and $R^{7c}$ is independently hydrogen or $C_1$-$C_3$ alkyl; each $R^8$, where present, is independently $C_1$-$C_6$ alkyl, $C_3$-$C_6$ cycloalkyl; halogen, oxo or —$OR^{8a}$, wherein the $C_1$-$C_6$ alkyl and $C_3$-$C_6$ cycloalkyl are independently optionally substituted by $R^{10}$;

$R^{8a}$ is hydrogen or $C_1$-$C_6$ alkyl;

each $R^9$ is independently $C_1$-$C_6$ alkyl, $C_2$-$C_6$ alkenyl, $C_2$-$C_6$ alkynyl, halogen, —CN, —$OR^{11}$, —$SR^{11}$, —$NR^{12}R^{13}$, —$NO_2$, —C=NH($OR^{11}$), —$C(O)R^{11}$, —OC(O)$R^{11}$, —C(O)O$R^{11}$, —C(O)N$R^{12}R^{13}$, —$NR^{11}C(O)R^{12}$, —$NR^{11}C(O)OR^{12}$, —$NR^{11}C(O)NR^{12}R^{13}$, —$S(O)R^{11}$, —$S(O)_2R^{11}$, —$NR^{11}S(O)R^{12}$, —$NR^{11}S(O)_2R^{12}$, —$S(O)NR^{12}R^{13}$, —$S(O)_2NR^{12}R^{13}$, —$P(O)(OR^{12})(OR^{13})$, $C_3$-$C_8$ cycloalkyl, 3- to 12-membered heterocyclyl, 5- to 10-membered heteroaryl, $C_6$-$C_{14}$ aryl, wherein each $R^9$ is independently optionally substituted by halogen, oxo, —$OR^{14}$, —$NR^{14}R^{15}$, —$C(O)R^{14}$, —CN, —$S(O)R^{14}$, —$S(O)_2R^{14}$, —$P(O)(OR^{14})(OR^{15})$, $C_3$-$C_8$ cycloalkyl, 3- to 12-membered heterocyclyl, 5- to 10-membered heteroaryl, $C_6$-$C_4$ aryl, or $C_1$-$C_6$ alkyl optionally substituted by oxo, —OH or halogen;
each $R^{10}$ is independently oxo or $R^9$;
$R^{11}$ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —$OR^{16}$, —$NR^{16}R^{17}$, —$P(O)(OR^{16})(OR^7)$, or $C_1$-$C_6$ alkyl optionally substituted by halogen, —OH or oxo;
$R^{12}$ and $R^{13}$ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —$OR^{16}$, —$NR^{16}R^{17}$ or $C_1$-$C_6$ alkyl optionally substituted by halogen, —OH or oxo;
or $R^{12}$ and $R^{13}$ are taken together with the atom to which they attached to form a 3- to 6-membered heterocyclyl optionally substituted by halogen, oxo, —$OR^{16}$, —$NR^{16}R^{17}$ or $C_1$-$C_6$ alkyl optionally substituted by halogen, oxo or —OH;
$R^{14}$ and $R^{15}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;
or $R^{14}$ and $R^{15}$ are taken together with the atom to which they attached to form a 3- to 6-membered heterocyclyl optionally substituted by halogen, oxo or $C_1$-$C_6$ alkyl optionally substituted by halogen or oxo; and
$R^{16}$ and $R^{17}$ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;
or $R^{16}$ and $R^{17}$ are taken together with the atom to which they attached to form a 3-6 membered heterocyclyl optionally substituted by halogen, oxo or $C_1$-$C_6$ alkyl optionally substituted by oxo or halogen.

In another aspect is provided is a compound of formula (I-A):

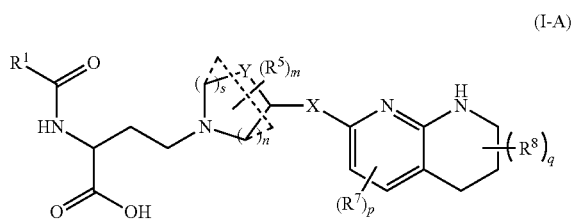

(I-A)

or a salt thereof, wherein:
$R^1$ is $C_1$-$C_6$ alkyl, $C_3$-$C_8$ cycloalkyl, $C_6$-$C_{14}$ aryl, 5- to 10-membered heteroaryl, 3- to 12-membered heterocyclyl, —$OR^2$ or —$NR^{3a}R^{3b}$, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^1$ are independently optionally substituted by $R^0$;

$R^2$ is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^2$ are independently optionally substituted by $R^{10}$;
$R^{3a}$ and $R^{3b}$ are independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{3a}$ and $R^{3b}$ are independently optionally substituted by $R^{10}$;
or $R^{3a}$ and $R^{3b}$ are taken together with the nitrogen to which they are attached to form a 4- to 8-membered heterocyclyl optionally substituted by $R^{10}$;
n is 1 or 2;
s is 0, 1 or 2, wherein the sum of n and s is 1, 2 or 3;
the ring defined by - - - - - - is present or absent;
m is 0 to 6;
each $R^5$, where present, is independently $C_1$-$C_6$ alkyl, $C_3$-$C_6$ cycloalkyl, halogen, —CN, —$OR^{5a}$, —$C(O)OR^{5a}$, —$NR^{5a}C(O)R^{5b}$; —$NR^{5c}R^{5d}$, —$C(O)NR^{5c}R^{5d}$, —$SO_2R^{5e}$, or —$SO_2NR^{5c}R^{5d}$, wherein the $C_1$-$C_6$ alkyl and $C_3$-$C_6$ cycloalkyl are independently optionally substituted by $R^{10}$;
each $R^{5a}$ and $R^{5b}$ is independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5a}$ and $R^{5b}$ are independently optionally substituted by $R^{10}$;
each $R^{5c}$ and $R^{5d}$ is independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5c}$ and $R^{5d}$ are independently optionally substituted by $R^{10}$;
or $R^{5c}$ and $R^{5d}$ are taken together with the nitrogen to which they are attached to form a 4- to 8-membered heterocyclyl optionally substituted by $R^{10}$;
each $R^{5e}$ is independently $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^{5e}$ are independently optionally substituted by $R^{10}$;
X is $C_1$-$C_3$ alkylene optionally substituted by $R^{10}$, —$N(R^{11})$—$C_1$-$C_3$ alkylene optionally substituted by $R^{10}$, —$C_1$-$C_3$ alkylene-$N(R^{11})$— optionally substituted by $R^{10}$, —$C_1$-$C_3$ alkylene-$N(R^{11})$— $C_1$-$C_3$ alkylene- optionally substituted by $R^{10}$, —O—$C_1$-$C_3$ alkylene optionally substituted by $R^{10}$, —$C_1$-$C_3$ alkylene-O— optionally substituted by $R^{10}$, —$C_1$-$C_3$ alkylene-O—$C_1$-$C_3$ alkylene- optionally substituted by $R^{10}$;
Y is $C(R^{ya})(R^{yb})$ or $N(R^{11})$;
each of $R^{ya}$ and $R^{yb}$ is independently H, $C_1$-$C_6$ alkyl, $C_3$-$C_6$ cycloalkyl, halogen, —CN, —$OR^{5a}$, —$C(O)OR^{5a}$, —$NR^{5a}C(O)R^{5b}$; —$NR^{5c}R^{5d}$, —$C(O)NR^{5c}R^{5d}$, —$SO_2R^{5e}$, or —$SO_2NR^{5c}R^{5d}$, wherein the $C_1$-$C_6$ alkyl and $C_3$-$C_6$ cycloalkyl are independently optionally substituted by $R^{10}$;
p is 0 to 2;
q is 0 to 6;
each $R^7$, where present, is independently $C_1$-$C_6$ alkyl optionally substituted by halogen or —OH, $C_3$-$C_6$ cycloalkyl, halogen, —CN, —$NO_2$, —$OR^{7a}$, or —$NR^{7b}R^{7c}$;
each $R^{7a}$, $R^{7b}$ and $R^{7c}$ is independently hydrogen or $C_1$-$C_3$ alkyl;

each R$^{8a}$, where present, is independently C$_1$-C$_6$ alkyl, C$_3$-C$_6$ cycloalkyl; halogen, oxo or —OR$^{8a}$, wherein the C$_1$-C$_6$ alkyl and C$_3$-C$_6$ cycloalkyl are independently optionally substituted by R$^{10}$;

R$^{8a}$ is hydrogen or C$_1$-C$_6$ alkyl;

each R$^9$ is independently C$_1$-C$_6$ alkyl, C$_2$-C$_6$ alkenyl, C$_2$-C$_6$ alkynyl, halogen, —CN, —OR$^{11}$, —SR$^{11}$, —NR$^{12}$R$^{13}$, —NO$_2$, —C=NH(OR$^{11}$), —C(O)R$^{11}$, —OC(O)R$^{11}$, —C(O)OR$^{11}$, —C(O)NR$^{12}$R$^{13}$, —NR$^{11}$C(O)R$^{12}$, —NR$^{11}$C(O)OR$^{12}$, —NR$^{11}$C(O)NR$^{12}$R$^{13}$, —S(O)R$^{11}$, —S(O)$_2$R$^{11}$, —NR$^{11}$S(O)R$^{12}$, —NR$^{11}$S(O)$_2$R$^{12}$, —S(O)NR$^{12}$R$^{13}$, —S(O)$_2$NR$^{12}$R$^{13}$, —P(O)(OR$^{12}$)(OR$^{13}$), C$_3$-C$_8$ cycloalkyl, 3- to 12-membered heterocyclyl, 5- to 10-membered heteroaryl, C$_6$-C$_{14}$ aryl, wherein each R$^9$ is independently optionally substituted by halogen, oxo, —OR$^{14}$, —NR$^{14}$R$^{15}$, —C(O)R$^{14}$, —CN, —S(O)R$^{14}$, —S(O)$_2$R$^{14}$, —P(O)(OR$^{14}$)(OR$^{15}$), C$_3$-C$_8$ cycloalkyl, 3- to 12-membered heterocyclyl, 5- to 10-membered heteroaryl, C$_6$-C$_4$ aryl, or C$_1$-C$_6$ alkyl optionally substituted by oxo, —OH or halogen;

each R$^{10}$ is independently oxo or R$^9$;

R$^{11}$ is independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$, —P(O)(OR$^{16}$)(OR$^{17}$), or C$_1$-C$_6$ alkyl optionally substituted by halogen, —OH or oxo;

R$^{12}$ and R$^{13}$ are each independently hydrogen, C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl or 3- to 6-membered heterocyclyl, wherein the C$_1$-C$_6$ alkyl, C$_2$-C$_6$ alkenyl, C$_2$-C$_6$ alkynyl, C$_3$-C$_6$ cycloalkyl, C$_6$-C$_{14}$ aryl, 5- to 6-membered heteroaryl and 3- to 6-membered heterocyclyl are independently optionally substituted by halogen, oxo, —CN, —OR$^{16}$, —NR$^{16}$R$^{17}$ or C$_1$-C$_6$ alkyl optionally substituted by halogen, —OH or oxo;

or R$^{12}$ and R$^{13}$ are taken together with the atom to which they attached to form a 3- to 6-membered heterocyclyl optionally substituted by halogen, oxo, —OR$^{16}$, —NR$^{16}$R$^{17}$ or C$_1$-C$_6$ alkyl optionally substituted by halogen, oxo or —OH;

R$^{14}$ and R$^{15}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{14}$ and R$^{15}$ are taken together with the atom to which they attached to form a 3- to 6-membered heterocyclyl optionally substituted by halogen, oxo or C$_1$-C$_6$ alkyl optionally substituted by halogen or oxo; and R$^{16}$ and R$^{17}$ are each independently hydrogen, C$_1$-C$_6$ alkyl optionally substituted by halogen or oxo, C$_2$-C$_6$ alkenyl optionally substituted by halogen or oxo, or C$_2$-C$_6$ alkynyl optionally substituted by halogen or oxo;

or R$^{16}$ and R$^{17}$ are taken together with the atom to which they attached to form a 3-6 membered heterocyclyl optionally substituted by halogen, oxo or C$_1$-C$_6$ alkyl optionally substituted by oxo or halogen.

It is understood that when the ring defined by - - - - - - is present, only one such ring is present.

In some embodiments, the compound of the formula (I) is a derivative of (S)-2-acylaminobutanoic acid, having the formula (Ia):

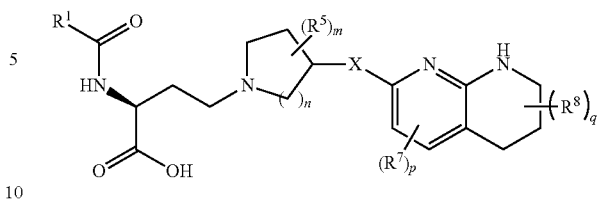

(Ia)

or a salt thereof, wherein R$^1$, R$^5$, R$^7$, R$^8$, X, m, n, p and q are as defined for formula (I).

In some embodiments, the compound of the formula (I) is a derivative of (R)-2-acylaminobutanoic acid, having the formula (Ib):

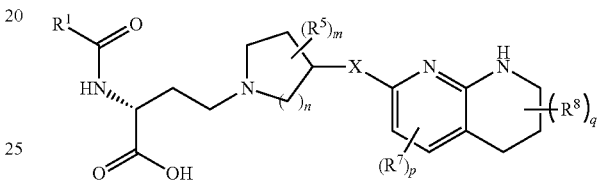

(Ib)

or a salt thereof, wherein R$^1$, R$^5$, R$^7$, R$^8$, X, m, n, p and q are as defined for formula (I).

In some embodiments of the compound of formula (I), (Ia) or (Ib), or a salt thereof, n is 1. In some embodiments, n is 2. In some of these embodiments, m is 0. In some these embodiments, m is 1. In some these embodiments, m is 2. In some these embodiments, m is 3. In some these embodiments, m is 4. In some these embodiments, m is 5. In some these embodiments, m is 6. In some embodiments, m is 1 or 2.

In some embodiments of the compound of formula (I), (Ia) or (Ib), or a salt thereof, each R$^5$, where present, is independently C$_1$-C$_6$ alkyl optionally substituted by R$^{10}$, C$_3$-C$_6$ cycloalkyl optionally substituted by R$^0$, halogen, —CN, —OR$^{5a}$, —C(O)OR$^{5a}$, —NR$^{5a}$C(O)R$^{5b}$; —NR$^{5c}$R$^{5d}$, —C(O)NR$^{5c}$R$^{5d}$, —SO$_2$R$^{5e}$, or —SO$_2$NR$^{5c}$R$^{5d}$. In some of these embodiments, each R$^{5a}$ and R$^{5b}$ is independently hydrogen, C$_1$-C$_6$ alkyl optionally substituted by R$^{10}$; C$_3$-C$_8$ cycloalkyl optionally substituted by R$^0$; C$_6$-C$_{14}$ aryl optionally substituted by R$^{10}$; 5- to 10-membered heteroaryl optionally substituted by R$^{10}$; or 3- to 12-membered heterocyclyl optionally substituted by R$^{10}$. In some of these embodiments, each R$^{5c}$ and R$^{5d}$ is independently hydrogen, C$_1$-C$_6$ alkyl optionally substituted by R$^{10}$; C$_3$-C$_8$ cycloalkyl optionally substituted by R$^{10}$; C$_6$-C$_4$ aryl optionally substituted by R$^{10}$; 5- to 10-membered heteroaryl optionally substituted by R$^{10}$; or 3- to 12-membered heterocyclyl optionally substituted by R$^{10}$; or R$^{5c}$ and R$^{5d}$ are taken together with the nitrogen to which they are attached to form a 4- to 8-membered heterocyclyl optionally substituted by R$^{10}$. In some of these embodiments, R$^{5e}$ is C$_1$-C$_6$ alkyl optionally substituted by R$^{10}$; C$_3$-C$_8$ cycloalkyl optionally substituted by R$^{10}$; C$_6$-C$_{14}$ aryl optionally substituted by R$^0$; 5- to 10-membered heteroaryl optionally substituted by R$^{10}$; or 3- to 12-membered heterocyclyl optionally substituted by R$^{10}$.

In some embodiments of the compound of formula (I), where n is 1 and m is 0, the compound is of the formula (II):

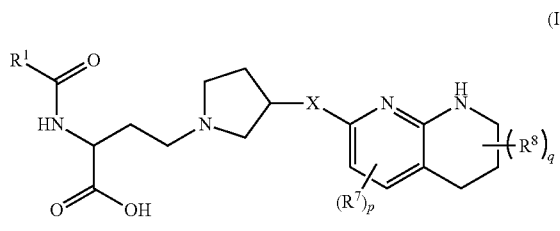

(II)

or a salt thereof, wherein $R^1$, $R^7$, $R^8$, X, p and q are as defined for formula (I).

In some embodiments, the compound of the formula (II) is a derivative of (S)-2-acylaminobutanoic acid, having the formula (IIa):

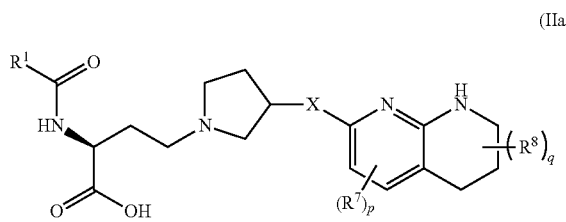

(IIa)

or a salt thereof, wherein $R^1$, $R^7$, $R^8$, X, p and q are as defined for formula (I) or (II).

In some embodiments, the compound of the formula (II) is a derivative of (R)-2-acylaminobutanoic acid, having the formula (IIb):

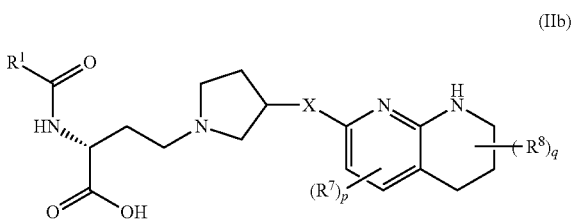

(IIb)

or a salt thereof, wherein $R^1$, $R^7$, $R^8$, X, p and q are as defined for formula (I) or (II).

In some embodiments of the compound of formula (I), where n is 2 and m is 0, the compound is of the formula (III):

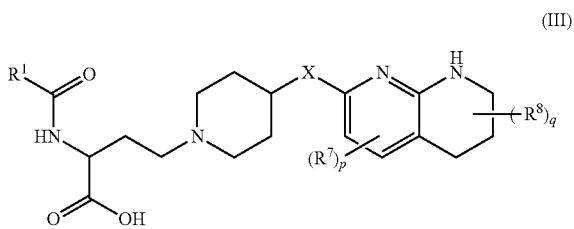

(III)

or a salt thereof, wherein $R^1$, $R^7$, $R^8$, X, p and q are as defined for formula (I).

In some embodiments, the compound of the formula (III) is a derivative of (S)-2-acylaminobutanoic acid, having the formula (IIIa):

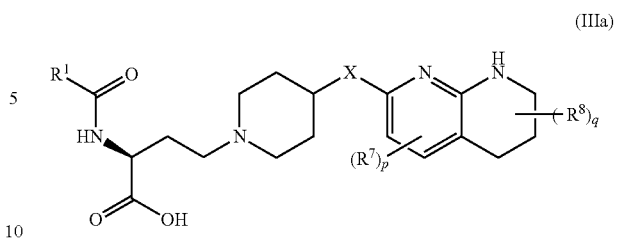

(IIIa)

or a salt thereof, wherein $R^1$, $R^7$, $R^8$, X, p and q are as defined for formula (I) or (III).

In some embodiments, the compound of the formula (III) is a derivative of (R)-2-acylaminobutanoic acid, having the formula (IIIb):

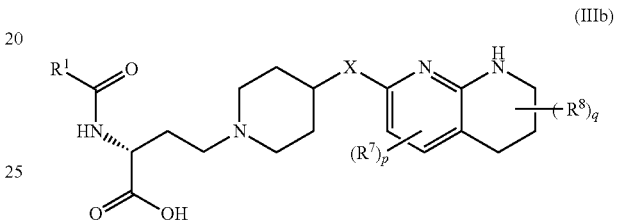

(IIIb)

or a salt thereof, wherein $R^1$, $R^7$, $R^8$, X, p and q are as defined for formula (I) or (III).

In some embodiments of the compound of formula (I), (Ia), (Ib), (II), (IIa), (IIb), (III), (IIIa) or (IIIb), or a salt thereof, X is $C_1$-$C_3$ alkylene optionally substituted by $R^{10}$. In some embodiments, X is $C_1$-$C_2$ alkylene optionally substituted by $R^{10}$. In some embodiments, X is methylene optionally substituted by 1 or 2 groups selected from $R^{10}$. In some embodiments, X is ethylene optionally substituted by 1 to 4 groups selected from $R^{10}$. In some embodiments, X is propylene optionally substituted by 1 or 5 groups selected from $R^{10}$. In some embodiments, X is methylene. In some embodiments, X is ethylene. In some embodiments, X is propylene.

It is intended and understood that each and every variation of n, m and $R^5$ described herein, may be combined with each and every variation of X described herein, the same as if each and every combination is individually and specifically described. For example, in some embodiments of the compound of formula (I), (Ia), (Ib), (II), (IIa), (IIb), (III), (IIIa) or (IIIb), or a salt thereof, n is 1, m is 0, and X is ethylene. In some embodiments of the compound of formula (I), (Ia), (Ib), (II), (IIa), (IIb), (III), (IIIa) or (IIIb), or a salt thereof, n is 2, m is 0, and X is ethylene.

In some embodiments of the compound of formula (I), where n is 1, m is 0, and X is ethylene, the compound is of the formula (IV):

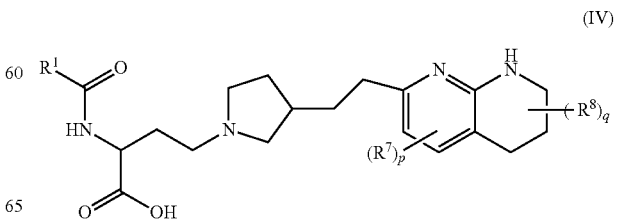

(IV)

or a salt thereof, wherein $R^1$, $R^7$, $R^8$, p and q are as defined for formula (I) or (II).

In some embodiments, the compound of the formula (IV) is of the formula (IVa):

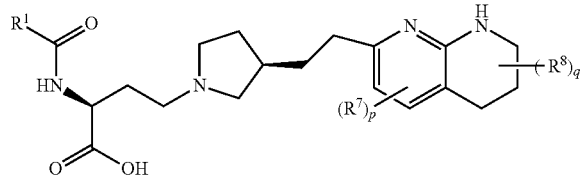

(IVa)

or a salt thereof, wherein $R^1$, $R^7$, $R^8$, p and q are as defined for formula (I) or (II).

In some embodiments, the compound of the formula (IV) is of the formula (IVb):

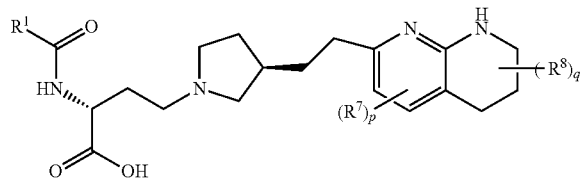

(IVb)

or a salt thereof, wherein $R^1$, $R^7$, $R^8$, p and q are as defined for formula (I) or (II).

In some embodiments, the compound of the formula (IV) is of the formula (IVc):

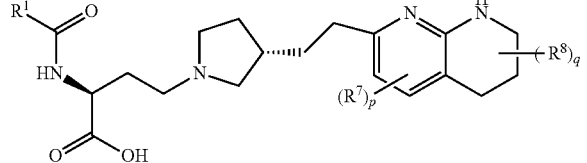

(IVc)

or a salt thereof, wherein $R^1$, $R^7$, $R^8$, p and q are as defined for formula (I) or (II).

In some embodiments, the compound of the formula (IV) is of the formula (IVd):

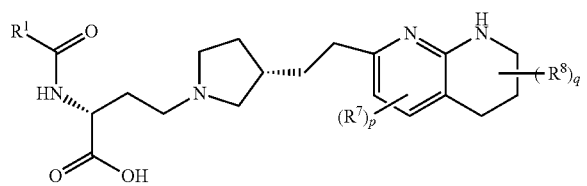

(IVd)

or a salt thereof, wherein $R^1$, $R^7$, $R^8$, p and q are as defined for formula (I) or (II).

In some embodiments of the compound of formula (I), where n is 2, m is 0, and X is ethylene, the compound is of the formula (V):

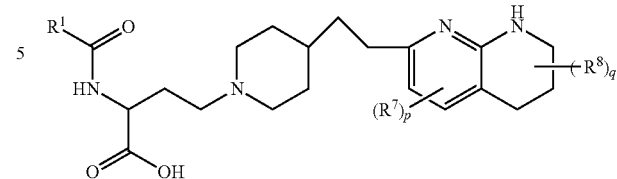

(V)

or a salt thereof, wherein $R^1$, $R^7$, $R^8$, p and q are as defined for formula (I) or (III).

In some embodiments, the compound of the formula (V) is of the formula (Va):

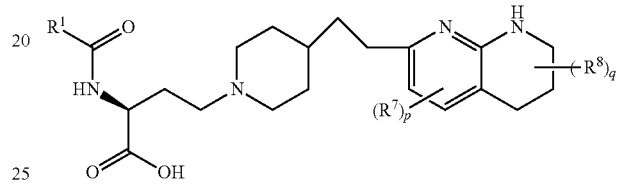

(Va)

or a salt thereof, wherein $R^1$, $R^7$, $R^8$, p and q are as defined for formula (I) or (III).

In some embodiments, the compound of the formula (V) is of the formula (Vb):

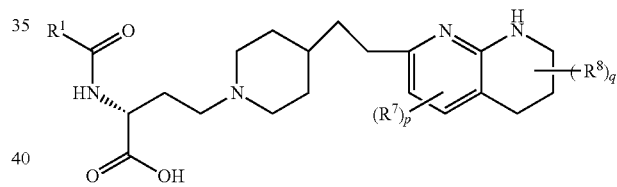

(Vb)

or a salt thereof, wherein $R^1$, $R^7$, $R^8$, p and q are as defined for formula (I) or (III).

In some embodiments of the compound of formula (I), (Ia), (Ib), (II), (IIa), (IIb), (III), (IIIa), (IIIb), (IV), (IVa), (IVb), (IVc), (IVd), (V), (Va) or (Vb), or a salt thereof, $R^1$ is $C_1$-$C_6$ alkyl optionally substituted by $R^{10}$; $C_3$-$C_8$ cycloalkyl optionally substituted by $R^{10}$; $C_6$-$C_{14}$ aryl optionally substituted by $R^{10}$; 5- to 10-membered heteroaryl optionally substituted by $R^{10}$; 3- to 12-membered heterocyclyl optionally substituted by $R^{10}$; —$OR^2$; or —$NR^{3a}R^{3b}$.

In some embodiments, $R^1$ is a $C_1$-$C_6$ alkyl (e.g., t-butyl) optionally substituted by $R^{10}$.

In some embodiments. $R^1$ is —$OR^2$ or —$NR^{3a}R^{3b}$.

In some embodiments, $R^1$ is —$OR^2$. In some embodiments, $R^2$ is $C_1$-$C_6$ alkyl (e.g., t-butyl).

In some embodiments, $R^1$ is —$NR^{3a}R^{3b}$. In some embodiments, $R^1$ is a 4- to 8-membered heterocyclyl optionally substituted by $R^{10}$ formed by $R^{3a}$ and $R^{3b}$ taken together with the nitrogen to which they are attached.

In some embodiments, $R^1$ is $C_3$-$C_8$ cycloalkyl (e.g., cyclohexyl) optionally substituted by $R^{10}$. In some embodiments, $R^1$ is 4,4-difluorocyclohexyl.

In some embodiments, $R^1$ is $C_6$-$C_{14}$ aryl optionally substituted by $R^{10}$. In some embodiments, $R^1$ is phenyl optionally substituted by $R^{10}$.

In some embodiments, $R^1$ is 5- or 10-membered heteroaryl optionally substituted by $R^{10}$. In some embodiments, $R^1$ is 5- to 6-membered monocyclic heteroaryl optionally substituted by $R^{10}$. In some embodiments, $R^1$ is pyridyl (e.g., 2-pyridyl, 3-pyridyl or 4-pyridyl) optionally substituted by $R^{10}$. In some embodiments, $R^1$ is 8- to 10-membered bicyclic heteroaryl optionally substituted by $R^{10}$. In some embodiments, $R^1$ is indazolyl (e.g., 4-indozyl, 5-indozyl, 6-indozyl or 7-indozyl) optionally substituted by $R^{10}$.

In some embodiments, $R^1$ is 3- to 12-membered heterocyclyl optionally substituted by $R^{10}$. In some embodiments, $R^1$ is piperidinyl (e.g., piperidin-4-yl) optionally substituted by $R^{10}$. In some embodiments, $R^1$ is 1-cyclopropylpiperidin-4-yl. In some embodiments, $R^1$ is tetrahydropyranyl (e.g., tetrahydropyran-4-yl) optionally substituted by $R^{10}$. In some embodiments, $R^1$ is 4-methyltetrahydropyran-4-yl.

It is intended and understood that each and every variation of $R^1$ described herein, may be combined with each and every variation of X, n, m and $R^5$ described herein, the same as if each and every combination is individually and specifically described. For example, in some embodiments of the compound of formula (I), (Ia), (Ib), (II), (IIa), (IIb), (III), (IIIa), (IIIb), (IV), (IVa), (IVb), (IVc), (IVd), (V), (Va) or (Vb), or a salt thereof, $R^1$ is selected from the group consisting of:

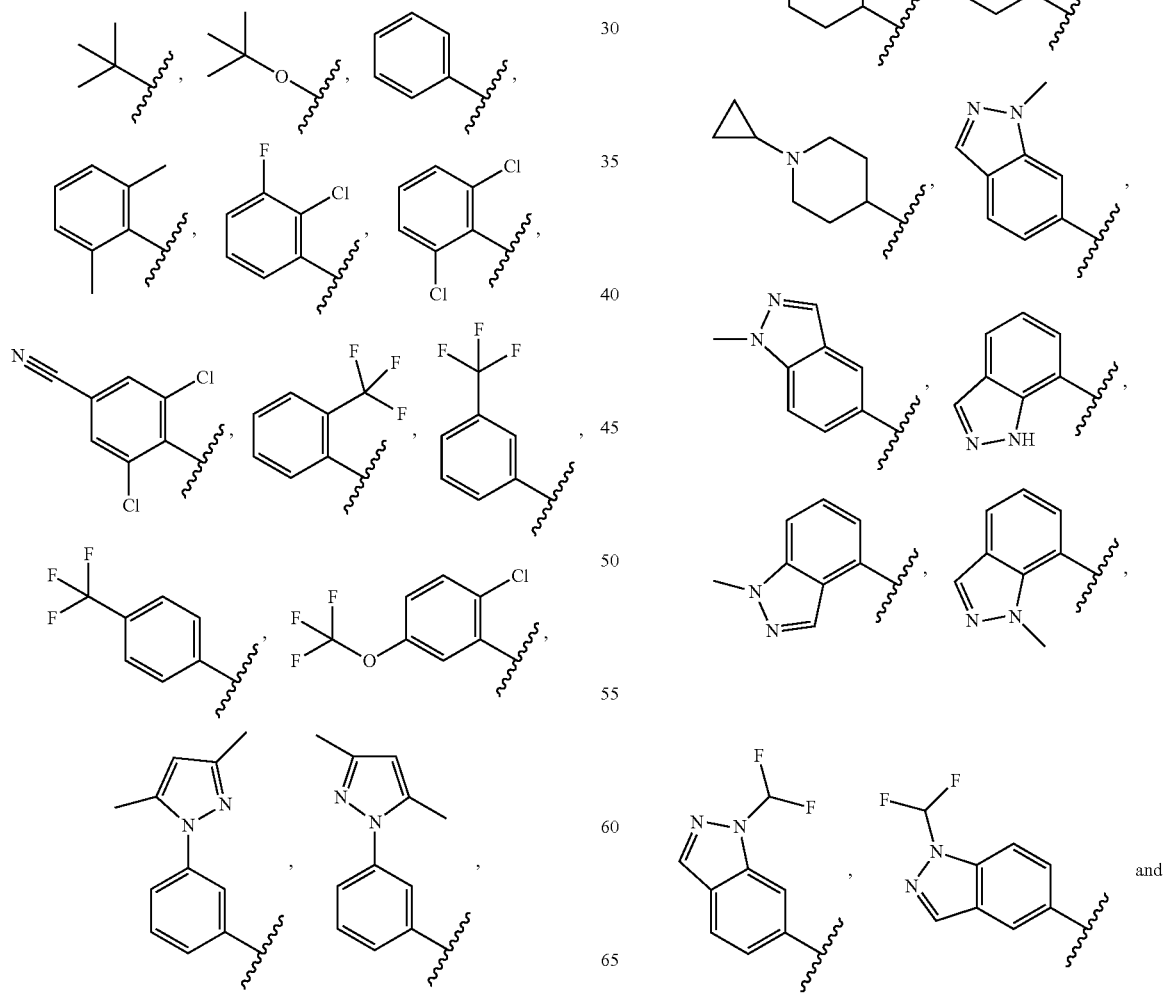

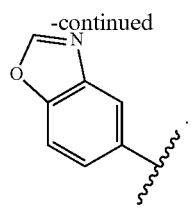

In the compound of formula (I), (Ia), (Ib), (II), (IIa), (IIb), (III), (IIIa), (IIIb), (IV), (IVa), (IVb), (IVc), (IVd), (V), (Va) or (Vb), or a salt thereof, the 5,6,7,8-tetrahydro-1,8-naphthyridine ring may be unsubstituted or substituted. In some embodiments, p is 0. In some embodiments, q is 0. In some embodiments, p and q are 0. In some embodiments, p is 1 or 2, and each $R^7$ is independently $C_1$-$C_6$ alkyl optionally substituted by halogen or —OH, $C_3$-$C_6$ cycloalkyl, halogen, —CN, —$NO_2$, —$OR^{7a}$, or —$NR^{7b}R^{7c}$; where each $R^{7a}$, $R^{7b}$ and $R^{7c}$ is independently hydrogen or $C_1$-$C_3$ alkyl. In some embodiments, $R^7$ is —$CH_3$, —$CHF_2$, —$CH_2F$, —$CF_3$, or —$CH_2OH$. In some embodiments, q is 1 to 6, and each $R^8$ is independently $C_1$-$C_6$ alkyl optionally substituted by $R^{10}$, $C_3$-$C_6$ cycloalkyl optionally substituted by $R^{10}$, halogen, oxo or —$OR^{8a}$. In some embodiments, $R^8$ is —$OR^{8a}$ where $R^{8a}$ is hydrogen or $C_1$-$C_6$ alkyl. In some embodiments, $R^{8a}$ is hydrogen.

In some embodiments, each optional substituent $R^9$ is independently $C_1$-$C_6$ alkyl, $C_2$-$C_6$ alkenyl, $C_2$-$C_6$ alkynyl, halogen, —CN, —$OR^{11}$, —$SR^{11}$, —$NR^{12}R^{13}$, —$NO_2$, —C=NH($OR^{11}$), —C(O)$R^{11}$, —OC(O)$R^{11}$, —C(O)$OR^{11}$, —C(O)$NR^{12}R^{13}$, —$NR^{11}$C(O)$R^{12}$, —$NR^{11}$C(O)$OR^{12}$, —$NR^{11}$C(O)$NR^{12}R^{13}$, —S(O)$R^{11}$, —S(O)$_2R^{11}$, —$NR^{11}$S(O)$R^{12}$, —$NR^{11}$S(O)$_2R^{12}$, —S(O)$NR^{12}R^{13}$, —S(O)$_2NR^{12}R^{13}$, —P(O)($OR^{12}$)($OR^{13}$), $C_3$-$C_8$ cycloalkyl, 3- to 12-membered heterocyclyl, 5- to 10-membered heteroaryl or $C_6$-$C_{14}$ aryl, wherein each $R^9$ is independently optionally substituted by halogen, oxo, —$OR^{14}$, —$NR^{14}R^{15}$, —C(O)$R^{14}$, —CN, —S(O)$R^{14}$, —S(O)$_2R^{14}$, —P(O)($OR^{14}$)($OR^5$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen.

In some embodiments, $R^9$ is independently $C_1$-$C_6$ alkyl, halogen, —CN, —$OR^{11}$, —$NR^{12}R^{13}$, —C(O)$R^{11}$, $C_3$-$C_8$ cycloalkyl, 3- to 12-membered heterocyclyl, 5- to 10-membered heteroaryl or $C_6$-$C_4$ aryl, wherein each $R^9$ is independently optionally substituted by halogen, oxo, —$OR^{14}$, —$NR^{14}R^{15}$, —C(O)$R^{14}$, —CN, $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen. In some embodiments, $R^9$ is independently selected from F, Cl, —CN, methyl, —$CHF_2$, —$CF_3$, cyclopropylmethyl, tert-butyl, cyclopropyl and phenyl. In some embodiments, $R^9$ is independently F, Cl or —CN. In some embodiments, $R^9$ is independently methyl, —$CHF_2$, —$CF_3$, cyclopropylmethyl, tert-butyl or cyclopropyl. In some embodiments, $R^9$ is independently phenyl optionally substituted by halogen or $C_1$-$C_6$ alkyl. In some embodiments, $R^9$ is 5- to 10-membered heteroaryl optionally substituted by $C_1$-$C_6$ alkyl. In some embodiments, $R^9$ is 3,5-dimethylpyrazol-1-yl. In some embodiments, $R^9$ is independently 3- to 12-membered heterocyclyl optionally substituted by oxo or $C_1$-$C_6$ alkyl.

In some embodiments, $R^9$ is morpholin-4-yl.

In some embodiments. $R^{10}$ is independently oxo or any variation detailed herein for $R^9$. In some embodiments, $R^{10}$ is independently oxo, $C_1$-$C_6$ alkyl, halogen, —CN, —$OR^{11}$, —$NR^{12}R^{13}$, —C(O)$R^{11}$, $C_3$-$C_x$ cycloalkyl, 3- to 12-membered heterocyclyl, 5- to 10-membered heteroaryl or $C_6$-$C_4$ aryl, wherein each $R^9$ is independently optionally substituted by halogen, oxo, —$OR^{14}$, —$NR^{14}R^{15}$, —C(O)$R^{14}$, —CN, $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen. In some embodiments, $R^{10}$ is independently selected from oxo, F, Cl, —CN, methyl, —$CHF_2$, —$CF_3$, cyclopropylmethyl, tert-butyl, cyclopropyl and phenyl. In some embodiments, $R^{10}$ is independently phenyl optionally substituted by halogen or $C_1$-$C_6$ alkyl. In some embodiments, $R^{10}$ is 5- to 10-membered heteroaryl optionally substituted by $C_1$-$C_6$ alkyl. In some embodiments, $R^{10}$ is 3,5-dimethylpyrazol-1-yl. In some embodiments, $R^{10}$ is independently 3- to 12-membered heterocyclyl optionally substituted by oxo or $C_1$-$C_6$ alkyl. In some embodiments, $R^{10}$ is morpholin-4-yl.

In some embodiments, $R^{11}$, $R^{12}$ and $R^{13}$ are each independently hydrogen or $C_1$-$C_6$ alkyl. In some embodiments, $R^{11}$ is hydrogen. In some embodiments. $R^{12}$ and $R^{13}$ are each hydrogen.

In some embodiments, $R^{14}$ and $R^{15}$ are each independently hydrogen or $C_1$-$C_6$ alkyl.

In one variation is provided a compound of the formula (I), or a salt thereof, wherein the carbon bearing the $CO_2H$ and NHC(O)$R^1$ moieties is in the "S" configuration. In another variation is provided a compound of the formula (I), or a salt thereof, wherein the carbon bearing the $CO_2H$ and NHC(O)R moieties is in the "R" configuration. In one variation is provided a compound of the formula (I), or a salt thereof, wherein the carbon bearing the X moiety is in the "S" configuration. In another variation is provided a compound of the formula (I), or a salt thereof, wherein the carbon bearing the X moiety is in the "R" configuration. In one aspect of formula (I), the carbon bearing the $CO_2H$ and NHC(O)$R^1$ moieties is in the "S" configuration and the carbon bearing the X moiety is in the "S" configuration. In one aspect of formula (I), the carbon bearing the $CO_2H$ and NHC(O)$R^1$ moieties is in the "S" configuration and the carbon bearing the X moiety is in the "R" configuration. In one aspect of formula (I), the carbon bearing the $CO_2H$ and NHC(O)$R^1$ moieties is in the "R" configuration and the carbon bearing the X moiety is in the "S" configuration. In one aspect of formula (I), the carbon bearing the $CO_2H$ and NHC(O)$R^1$ moieties is in the "R" configuration and the carbon bearing the X moiety is in the "R" configuration. It is understood that the stereochemistry described is equally applicable to and described for other compounds detailed herein, such as compounds of the formula (I-A) and compounds in the associated compound tables, such as Table 1 and Table 1-A.

Representative compounds are listed in Table 1.

TABLE 1

| Compound No. | Structure | Chemical Name [1] |
|---|---|---|
| 1 | (structure shown) | 2-pivalamido-4-(3-(2-(5,6,7,8-tetrahydro-1,8-naphthyridin-2-yl)ethyl)pyrrolidin-1-yl)butanoic acid |
| 1a | | (S)-2-pivalamido-4-((R)-3-(2-(5,6,7,8-tetrahydro-1,8-naphthyridin-2-yl)ethyl)pyrrolidin-1-yl)butanoic acid |
| 1b | | (S)-2-pivalamido-4-((S)-3-(2-(5,6,7,8-tetrahydro-1,8-naphthyridin-2-yl)ethyl)pyrrolidin-1-yl)butanoic acid |
| 1c | | (R)-2-pivalamido-4-((R)-3-(2-(5,6,7,8-tetrahydro-1,8-naphthyridin-2-yl)ethyl)pyrrolidin-1-yl)butanoic acid |
| 1d | | (R)-2-pivalamido-4-((S)-3-(2-(5,6,7,8-tetrahydro-1,8-naphthyridin-2-yl)ethyl)pyrrolidin-1-yl)butanoic acid |
| 2 | (structure shown) | 2-((tert-butoxycarbonyl)amino)-4-(3-(2-(5,6,7,8-tetrahydro-1,8-naphthyridin-2-yl)ethyl)pyrrolidin-1-yl)butanoic acid |
| 2a | | (S)-2-((tert-butoxycarbonyl)amino)-4-((R)-3-(2-(5,6,7,8-tetrahydro-1,8-naphthyridin-2-yl)ethyl)pyrrolidin-1-yl)butanoic acid |
| 2b | | (S)-2-((tert-butoxycarbonyl)amino)-4-((S)-3-(2-(5,6,7,8-tetrahydro-1,8-naphthyridin-2-yl)ethyl)pyrrolidin-1-yl)butanoic acid |
| 2c | | (R)-2-((tert-butoxycarbonyl)amino)-4-((R)-3-(2-(5,6,7,8-tetrahydro-1,8-naphthyridin-2-yl)ethyl)pyrrolidin-1-yl)butanoic acid |
| 2d | | (R)-2-((tert-butoxycarbonyl)amino)-4-((S)-3-(2-(5,6,7,8-tetrahydro-1,8-naphthyridin-2-yl)ethyl)pyrrolidin-1-yl)butanoic acid |
| 3 | (structure shown) | 2-benzamido-4-(3-(2-(5,7,8-tetrahydro-1,8-naphthyridin-2-yl)ethyl)pyrrolidin-1-yl)butanoic acid |
| 3a | | (S)-2-benzamido-4-((R)-3-(2-(5,6,7,8-tetrahydro-1,8-naphthyridin-2-yl)ethyl)pyrrolidin-1-yl)butanoic acid |
| 3b | | (S)-2-benzamido-4-((S)-3-2-(5,6,7,8-tetrahydro-1,8-naphthyridin-2-yl)ethyl)pyrrolidin-1-yl)butanoic acid |
| 3c | | (R)-2-benzamido-4-((R)-3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name [1] |
|---|---|---|
| 3d | | (R)-2-benzamido-4-((S)-3-(2-(5,6,7,8-tetrahydro-1,8-naphthyridin-2-yl)ethyl)pyrrolidin-1-yl)butanoic acid |
| 4 | *(structure shown)* | 2-(2,6-dimethylbenzamido)-4-(3-(2-(5,6,7,8-tetrahydro-1,8-naphthyridin-2-yl)ethyl)pyrrolidin-1-yl)butanoic acid |
| 4a | | (S)-2-(2,6-dimethylbenzamido)-4-((R)-3-(2-(5,6,7,8-tetrahydro-1,8-naphthyridin-2-yl)ethyl)pyrrolidin-1-yl)butanoic acid |
| 4b | | (S)-2-(2,6-dimethylbenzamido)-4-((S)-3-(2-(5,6,7,8-tetrahydro-1,8-naphthyridin-2-yl)ethyl)pyrrolidin-1-yl)butanoic acid |
| 4c | | (R)-2-(2,6-dimethylbenzamido)-4-((R)-3-(2-(5,6,7,8-tetrahydro-1,8-naphthyridin-2-yl)ethyl)pyrrolidin-1-yl)butanoic acid |
| 4d | | (R)-2-(2,6-dimethylbenzamido)-4-((S)-3-(2-(5,6,7,8-tetrahydro-1,8-naphthyridin-2-yl)ethyl)pyrrolidin-1-yl)butanoic acid |
| 5 | *(structure shown)* | 2-(2-chloro-3-fluorobenzamido)-4-(3-(2-(5,6,7,8-tetrahydro-1,8-naphthyridin-2-yl)ethyl)pyrrolidin-1-yl)butanoic acid |
| 5a | | (S)-2-(2-chloro-3-fluorobenzamido)-4-((R)-3-(2-(5,6,7,8-tetrahydro-1,8-naphthyridin-2-yl)ethyl)pyrrolidin-1-yl)butanoic acid |
| 5b | | (S)-2-(2-chloro-3-fluorobenzamido)-4-((S)-3-(2-(5,6,7,8-tetrahydro-1,8-naphthyridin-2-yl)ethyl)pyrrolidin-1-yl)butanoic acid |
| 5c | | (R)-2-(2-chloro-3-fluorobenzamido)-4-((R)-3-(2-(5,6,7,8-tetrahydro-1,8-naphthyridin-2-yl)ethyl)pyrrolidin-1-yl)butanoic acid |
| 5d | | (R)-2-(2-chloro-3-fluorobenzamido)-4-((S)-3-(2-(5,6,7,8-tetrahydro-1,8-naphthyridin-2-yl)ethyl)pyrrolidin-1-yl)butanoic acid |
| 6 | *(structure shown)* | |

TABLE 1-continued

| Compound No. | Structure | Chemical Name [1] |
|---|---|---|
| 6a | | (S)-2-(2,6-dichlorobenzamido)-4-((R)-3-(2-(5,6,7,8-tetrahydro-1,8-naphthyridin-2-yl)ethyl)pyrrolidin-1-yl)butanoic acid |
| 6b | | (S)-2-(2,6-dichlorobenzamido)-4-((S)-3-(2-(5,6,7,8-tetrahydro-1,8-naphthyridin-2-yl)ethyl)pyrrolidin-1-yl)butanoic acid |
| 6c | | (R)-2-(2,6-dichlorobenzamido)-4-((R)-3-(2-(5,6,7,8-tetrahydro-1,8-naphthyridin-2-yl)ethyl)pyrrolidin-1-yl)butanoic acid |
| 6d | | (R)-2-(2,6-dichlorobenzamido)-4-((S)-3-(2-(5,6,7,8-tetrahydro-1,8-naphthyridin-2-yl)ethyl)pyrrolidin-1-yl)butanoic acid |
| 7 | (structure) | 2-(2,6-dichloro-4-cyanobenzamido)-4-(3-(2-(5,6,7,8-tetrahydro-1,8-naphthyridin-2-yl)ethyl)pyrrolidin-1-yl)butanoic acid |
| 7a | | (S)-2-(2,6-dichloro-4-cyanobenzamido)-4-((R)-3-(2-(5,6,7,8-tetrahydro-1,8-naphthyridin-2-yl)ethyl)pyrrolidin-1-yl)butanoic acid |
| 7b | | (S)-2-(2,6-dichloro-4-cyanobenzamido)-4-((S)-3-(2-(5,6,7,8-tetrahydro-1,8-naphthyridin-2-yl)ethyl)pyrrolidin-1-yl)butanoic acid |
| 7c | | (R)-2-(2,6-dichloro-4-cyanobenzamido)-4-((R)-3-(2-(5,6,7,8-tetrahydro-1,8-naphthyridin-2-yl)ethyl)pyrrolidin-1-yl)butanoic acid |
| 7d | | (R)-2-(2,6-dichloro-4-cyanobenzamido)-4-((S)-3-(2-(5,6,7,8-tetrahydro-1,8-naphthyridin-2-yl)ethyl)pyrrolidin-1-yl)butanoic acid |
| 8 | (structure) | 4-(3-(2-(5,6,7,8-tetrahydro-1,8-naphthyridin-2-yl)ethyl)pyrrolidin-1-yl)-2-(2-(trifluoromethyl)benzamido)butanoic acid |
| 8a | | (S)-4-((R)-3-(2-(5,6,7,8-tetrahydro-1,8-naphthyridin-2-yl)ethyl)pyrrolidin-1-yl)-2-(2-(trifluoromethyl)benzamido)butanoic acid |
| 8b | | (S)-4-((S)-3-(2-(5,6,7,8-tetrahydro-1,8-naphthyridin-2-yl)ethyl)pyrrolidin-1-yl)-2-(2-(trifluoromethyl)benzamido)butanoic acid |
| 8c | | (R)-4-(R)-3-(2-(5,6,7,8-tetrahydro-1,8-naphthyridin-2-yl)ethyl)pyrrolidin-1-yl)-2-(2-(trifluoromethyl)benzamido)butanoic acid |

TABLE 1-continued

| Compound No. | Structure | Chemical Name [1] |
|---|---|---|
| 8d | | (R)-4-((S)-3-(2-(5,6,7,8-tetrahydro-1,8-naphthyridin-2-yl)ethyl)pyrrolidin-1-yl)-2-(2-(trifluoromethyl)benzamido)butanoic acid |
| 9 | (structure shown) | 4-(3-(2-(5,6,7,8-tetrahydro-1,8-naphthyridin-2-yl)ethyl)pyrrolidin-1-yl)-2-(3-(trifluoromethyl)benzamido)butanoic acid |
| 9a | | (S)-4-((R)-3-(2-(5,6,7,8-tetrahydro-1,8-naphthyridin-2-yl)ethyl)pyrrolidin-1-yl)-2-(3-(trifluoromethyl)benzamido)butanoic acid |
| 9b | | (S)-4-((S)-3-(2-(5,6,7,8-tetrahydro-1,8-naphthyridin-2-yl)ethyl)pyrrolidin-1-yl)-2-(3-(trifluoromethyl)benzamido)butanoic acid |
| 9c | | (R)-4-((R)-3-(2-(5,6,7,8-tetrahydro-1,8-naphthyridin-2-yl)ethyl)pyrrolidin-1-yl)-2-(3-(trifluoromethyl)benzamido)butanoic acid |
| 9d | | (R)-4-((S)-3-(2-(5,6,7,8-tetrahydro-1,8-naphthyridin-2-yl)ethyl)pyrrolidin-1-yl)-2-(3-(trifluoromethyl)benzamido)butanoic acid |
| 10 | (structure shown) | 4-(3-(2-(5,6,7,8-tetrahydro-1,8-naphthyridin-2-yl)ethyl)pyrrolidin-1-yl)-2-(4-(trifluoromethyl)benzamido)butanoic acid |
| 10a | | (S)-4-((R)-3-(2-(5,6,7,8-tetrahydro-1,8-naphthyridin-2-yl)ethyl)pyrrolidin-1-yl)-2-(4-(trifluoromethyl)benzamido)butanoic acid |
| 10b | | (S)-4-((S)-3-(2-(5,6,7,8-tetrahydro-1,8-naphthyridin-2-yl)ethyl)pyrrolidin-1-yl)-2-(4-(trifluoromethyl)benzamido)butanoic acid |
| 10c | | (R)-4-((R)-3-(2-(5,6,7,8-tetrahydro-1,8-naphthyridin-2-yl)ethyl)pyrrolidin-1-yl)-2-(4-trifluoromethyl)benzamido)butanoic acid |
| 10d | | (R)-4-((S)-3-(2-(5,6,7,8-tetrahydro-1,8-naphthyridin-2-yl)ethyl)pyrrolidin-1-yl)-2-(4-(trifluoromethyl)benzamido)butanoic acid |

TABLE 1-continued

| Compound No. | Structure | Chemical Name[1] |
|---|---|---|
| 11 | 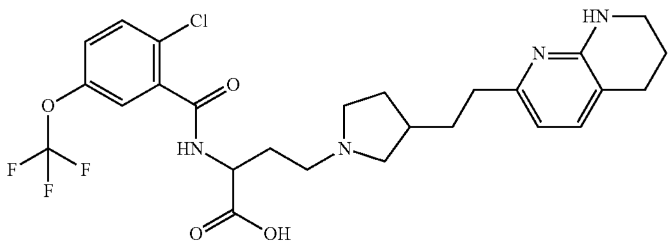 [SMILES: O=C(NC(CCN1CCC(CCc2ccc3c(n2)NCCC3)C1)C(=O)O)c1cc(OC(F)(F)F)ccc1Cl] | 2-(2,6-dichlorobenzamido)-4-(3-(2-(5,6,7,8-tetrahydro-1,8-naphthyridin-2-yl)ethyl)pyrrolidin-1-yl)butanoic acid |
| 11a | | (S)-2-(2,6-dichlorobenzamido)-4-((R)-3-(2-(5,6,7,8-tetrahydro-1,8-naphthyridin-2-yl)ethyl)pyrrolidin-1-yl)butanoic acid |
| 11b | | (S)-2-(2,6-dichlorobenzamido)-4-((S)-3-(2-(5,6,7,8-tetrahydro-1,8-naphthyridin-2-yl)ethyl)pyrrolidin-1-yl)butanoic acid |
| 11c | | (R)-2-(2,6-dichlorobenzamido)-4-((R)-3-(2-(5,6,7,8-tetrahydro-1,8-naphthyridin-2-yl)ethyl)pyrrolidin-1-11dyl)butanoic acid |
| 11d | | (R)-2-(2,6-dichlorobenzamido)-4-((S)-3-(2-(5,6,7,8-tetrahydro-1,8-naphthyridin-2-yl)ethyl)pyrrolidin-1-yl)butanoic acid |
| 12 | 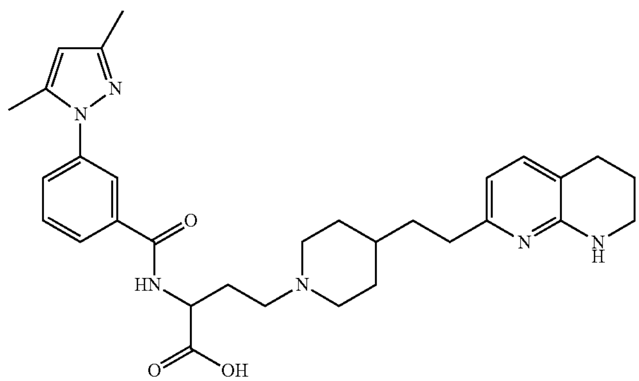 [SMILES: Cc1cc(C)n(-c2cccc(C(=O)NC(CCN3CCC(CCc4ccc5c(n4)NCCC5)CC3)C(=O)O)c2)n1] | 2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid |
| 12a | | (S)-2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid |
| 12b | | (R)-2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid |
| 13 | 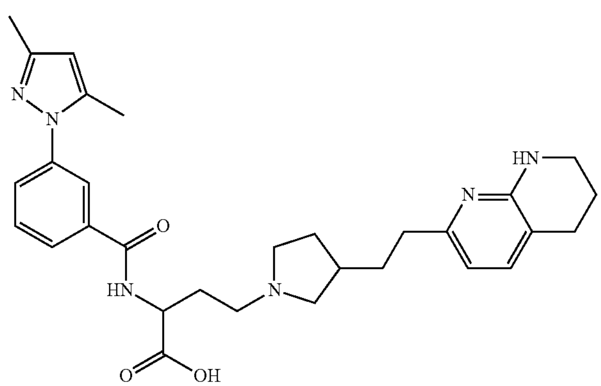 [SMILES: Cc1cc(C)n(-c2cccc(C(=O)NC(CCN3CCC(CCc4ccc5c(n4)NCCC5)C3)C(=O)O)c2)n1] | 2-(3-(3,5-dimethyl-1H-pyrazol-1-yl)benzamido)-4-(3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name[1] |
|---|---|---|
| 13a | | (S)-2-(3-(3,5-dimethyl-1H-pyrazol-1-yl)benzamido)-4-((R)-3-(2-(5,6,7,8-tetrahydro-1,8-naphthyridin-2-yl)ethyl)pyrrolidin-1-yl)butanoic acid |
| 13b | | (S)-2-(3-(3,5-dimethyl-1H-pyrazol-1-yl)benzamido)-4-((S)-3-(2-(5,6,7,8-tetrahydro-1,8-naphthyridin-2-yl)ethyl)pyrrolidin-1-yl)butanoic acid |
| 13c | | (R)-2-(3-(3,5-dimethyl-1H-pyrazol-1-yl)benzamido)-4-((R)-3-(2-(5,6,7,8-tetrahydro-1,8-naphthyridin-2-yl)ethyl)pyrrolidin-1-yl)butanoic acid |
| 13d | | (R)-2-(3-(3,5-dimethyl-1H-pyrazol-1-yl)benzamido)-4-((S)-3-(2-(5,6,7,8-tetrahydro-1,8-naphthyridin-2-yl)ethyl)pyrrolidin-1-yl)butanoic acid |
| 14 | *[structure image]* | 2-(2-morpholinobenzamido)-4-(3-(2-(5,6,7,8-tetrahydro-1,8-naphthyridin-2-yl)ethyl)pyrrolidin-1-yl)butanoic acid |
| 14a | | (S)-2-(2-morpholinobenzamido)-4-((R)-3-(2-(5,6,7,8-tetrahydro-1,8-naphthyridin-2-yl)ethyl)pyrrolidin-1-yl)butanoic acid |
| 14b | | (S)-2-(2-morpholinobenzamido)-4-((S)-3-(2-(5,6,7,8-tetrahydro-1,8-naphthyridin-2-yl)ethyl)pyrrolidin-1-yl)butanoic acid |
| 14c | | (S)-(2-morpholinobenzamido)-4-((R)-3-(2-(5,6,7,8-tetrahydro-1,8-naphthyridin-2-yl)ethyl)pyrrolidin-1-yl)butanoic acid |
| 14d | | (R)-2-(2-morpholinobenzamido)-4-((S)-3-(2-(5,6,7,8-tetrahydro-1,8-naphthyridin-2-yl)ethyl)pyrrolidin-1-yl)butanoic acid |
| 15 | *[structure image]* | 2-(3-morpholinobenzamido)-4-(3-(2-(5,6,7,8-tetrahydro-1,8-naphthyridin-2-yl)ethyl)pyrrolidin-1-yl)butanoic acid |
| 15a | | (S)-2-(3-morpholinobenzamido)-4-((R)-3-(2-(5,6,7,8-tetrahydro-1,8-naphthyridin-2-yl)ethyl)pyrrolidin-1-yl)butanoic acid |
| 15b | | S)-2-(3-morpholinobenzamido)-4-((S)-3-(2-(5,6,7,8-tetrahydro-1,8-naphthyridin-2-yl)ethyl)pyrrolidin-1-yl)butanoic acid |
| 15c | | (R)-2-(3-morpholinobenzamido)-4-((R)-3-(2-(5,6,7,8-tetrahydro-1,8- |

TABLE 1-continued

| Compound No. | Structure | Chemical Name [1] |
|---|---|---|
| | | naphthyridin-2-yl)ethyl)pyrrolidin-1-yl)butanoic acid |
| 15d | | (R)-2-(3-morpholinobenzamido)-4-((S)-3-(2-(5,6,7,8-tetrahydro-1,8-naphthyridin-2-yl)ethyl)pyrrolidin-1-yl)butanoic acid |
| 16 | [structure] | 2-(4-morpholinobenzamido)-4-(3-(2-(5,6,7,8-tetrahydro-1,8-naphthyridin-2-yl)ethyl)pyrrolidinal-yl)butanoic acid |
| 16a | | (S)-2-(4-morpholinobenzamido)-4-((R)-3-(2-(5,6,7,8-tetrahydro-1,8-naphthyridin-2-yl)ethyl)pyrrolidin-1-yl)butanoic acid |
| 16b | | (S)-2-(4-morpholinobenzamido)-4-((S)-3-(2-(5,6,7,8-tetrahydro-1,8-naphthyridin-2-yl)ethyl)pyrrolidin-1-yl)butanoic acid |
| 16c | | (R)-2-(4-morpholinobenzamido)-4-((R)-3-(2-(5,6,7,8-tetrahydro-1,8-naphthyridin-2-yl)ethyl)pyrrolidin-1-yl)butanoic acid |
| 16d | | (R)-2-(4-morpholinobenzamido)-4-((S)-3-(2-(5,6,7,8-tetrahydro-1,8-naphthyridin-2-yl)ethyl)pyrrolidin-1-yl)butanoic acid |
| 17 | [structure] | 2-(picolinamido)-4-(3-(2-(5,6,7,8-tetrahydro-1,8-naphthyridin-2-yl)ethyl)pyrrolidin-1-yl)butanoic acid |
| 17a | | (S)-2-(picolinamido)-4-((R)-3-(2-(5,6,7,8-tetrahydro-1,8-naphthyridin-2-yl)ethyl)pyrrolidin-1-yl)butanoic acid |
| 17b | | (S)-2-(picolinamido)-4-((S)-3-(2-(5,6,7,8-tetrahydro-1,8-naphthyridin-2-yl)ethyl)pyrrolidin-1-yl)butanoic acid |
| 17c | | (R)-2-(picolinamido)-4-((R)-3-(2-(5,6,7,8-tetrahydro-1,8-naphthyridin-2-yl)ethyl)pyrrolidin-1-yl)butanoic acid |
| 17d | | (R)-2-(picolinamido)-4-((S)-3-(2-(5,6,7,8-tetrahydro-1,8-naphthyridin-2-yl)ethyl)pyrrolidin-1-yl)butanoic acid |
| 18 | [structure] | 2-(isonicotinamido)-4-(3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name [1] |
|---|---|---|
| 18a | | (S)-2-(isonicotinamido)-4-((R)-3-(2-(5,6,7,8-tetrahydro-1,8-naphthyridin-2-yl)ethyl)pyrrolidin-1-yl)butanoic acid |
| 18b | | (S)-2-(isonicotinamido)-4-((S)-3-(2-(5,6,7,8-tetrahydro-1,8-naphthyridin-2-yl)ethyl)pyrrolidin-1-yl)butanoic acid |
| 18c | | (R)-2-isonicotinamido)-4-((R)-3-(2-(5,6,7,8-tetrahydro-1,8-naphthyridin-2-yl)ethyl)pyrrolidin-1-yl)butanoic acid |
| 18d | | (R)-2-(isonicotinamido)-4-((S)-3-(2-(5,6,7,8-tetrahydro-1,8-naphthyridin-2-yl)ethyl)pyrrolidin-1-yl)butanoic acid |
| 19 | 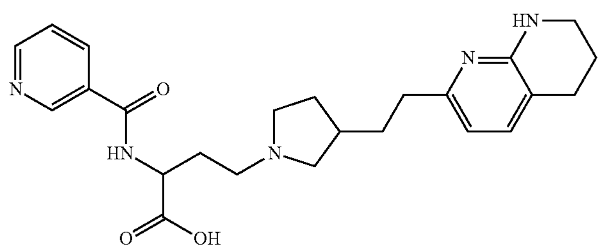 [SMILES: O=C(NC(CCN1CCC(CCc2ccc3c(n2)NCCC3)C1)C(=O)O)c1cccnc1] | 2-(nicotinamido)-4-(3-(2-(5,6,7,8-tetrahydro-1,8-naphthyridin-2-yl)ethyl)pyrrolidin-1-yl)butanoic acid |
| 19a | | (S)-2-(nicotinamido)-4-((R)-3-(2-(5,6,7,8-tetrahydro-1,8-naphthyridin-2-yl)ethyl)pyrrolidin-1-yl)butanoic acid |
| 19b | | (S)-2-(nicotinamido)-4-((S)-3-(2-(5,6,7,8-tetrahydro-1,8-naphthyridin-2-yl)ethyl)pyrrolidin-1-yl)butanoic acid |
| 19c | | (R)-2-(nicotinamido)-4-(R)-3-(2-(5,6,7,8-tetrahydro-1,8-naphthyridin-2-yl)ethyl)pyrrolidin-1-yl)butanoic acid |
| 19d | | (R)-2-(nicotinamido)-4-((S)-3-(2-(5,6,7,8-tetrahydro-1,8-naphthyridin-2-yl)ethyl)pyrrolidin-1-yl)butanoic acid |
| 20 | 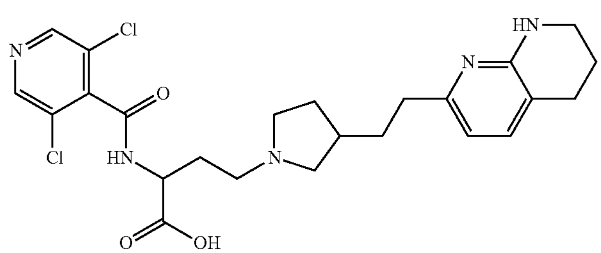 [SMILES: O=C(NC(CCN1CCC(CCc2ccc3c(n2)NCCC3)C1)C(=O)O)c1c(Cl)cncc1Cl] | 2-(3,5-dichloroisonicotinamido)-4-(3-(2-(5,6,7,8-tetrahydro-1,8-naphthyridin-2-yl)ethyl)pyrrolidin-1-yl)butanoic acid |
| 20a | | (S)-2-(3,5-dichloroisonicotinamido)-4-((R)-3-(2-(5,6,7,8-tetrahydro-1,8-naphthyridin-2-yl)ethyl)pyrrolidin-1-yl)butanoic acid |
| 20b | | (S)-2-(3,5-dichloroisonicotinamido)-4-((S)-3-(2-(5,6,7,8-tetrahydro-1,8-naphthyridin-2-yl)ethyl)pyrrolidin-1-yl)butanoic acid |
| 20c | | (R)-2-(3,5-dichloroisonicotinamido)-4-((R)-3-(2-(5,6,7,8-tetrahydro-1,8-naphthyridin-2-yl)ethyl)pyrrolidin-1-yl)butanoic acid |
| 20d | | (R)-2-(3,5-dichloroisonicotinamido)-4-((S)-3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name [1] |
|---|---|---|
| 21 | 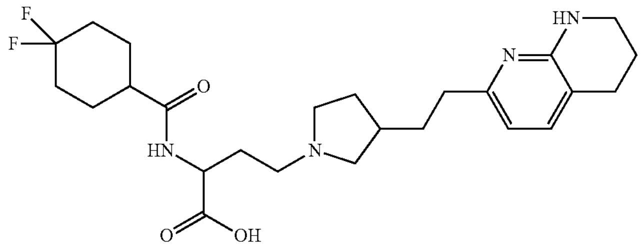 [SMILES: O=C(NC(CCN1CCC(CCc2ccc3c(n2)NCCC3)C1)C(=O)O)C1CCC(F)(F)CC1] | 2-(4,4-difluorocyclohexane-1-carboxamido)-4-(3-(2-(5,6,7,8-tetrahydro-1,8-naphthyridin-2-yl)ethyl)pyrrolidin-1-yl)butanoic acid |
| 21a | | (S)-2-(4,4-difluorocyclohexane-1-carboxamido)-4-((R)-3-(2-(5,6,7,8-tetrahydro-1,8-naphthyridin-2-yl)ethyl)pyrrolidin-1-yl)butanoic acid |
| 21b | | (S)-2-(4,4-difluorocyclohexane-1-carboxamido)-4-((S)-3-(2-(5,6,7,8-tetrahydro-1,8-naphthyridin-2-yl)ethyl)pyrrolidin-1-yl)butanoic acid |
| 21c | | (R)-2-(4,4-difluorocyclohexane-1-carboxamido)-4-((R)-3-(2-(5,6,7,8-tetrahydro-1,8-naphthyridin-2-yl)ethyl)pyrrolidin-1-yl)butanoic acid |
| 21d | | (R)-2-(4,4-difluorocyclohexane-1-carboxamido)-4-((S)-3-(2-(5,6,7,8-tetrahydro-1,8-naphthyridin-2-yl)ethyl)pyrrolidin-1-yl)butanoic acid |
| 22 | 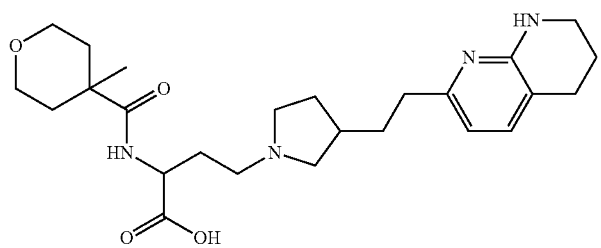 [SMILES: CC1(C(=O)NC(CCN2CCC(CCc3ccc4c(n3)NCCC4)C2)C(=O)O)CCOCC1] | 2-(4-methyltetrahydro-2H-pyran-4-carboxamido)-4-(3-(2-(5,6,7,8-tetrahydro-1,8-naphthyridin-2-yl)ethyl)pyrrolidin-1-yl)butanoic acid |
| 22a | | (S)-2-(4-methyltetrahydro-2H-pyran-4-carboxamido)-4-((R)-3-(2-(5,6,7,8-tetrahydro-1,8-naphthyridin-2-yl)ethyl)pyrrolidin-1-yl)butanoic acid |
| 22b | | (S)-2-(4-methyltetrahydro-2H-pyran-4-carboxamido)-4-((S)-3-(2-(5,6,7,8-tetrahydro-1,8-naphthyridin-2-yl)ethyl)pyrrolidin-1-yl)butanoic acid |
| 22c | | (R)-2-(4-methyltetrahydro-2H-pyran-4-carboxamido)-4-((R)-3-(2-(5,6,7,8-tetrahydro-1,8-naphthyridin-2-yl)ethyl)pyrrolidin-1-yl)butanoic acid |
| 22d | | (R)-2-(4-methyltetrahydro-2H-pyran-4-carboxamido)-4-((S)-3-(2-(5,6,7,8-tetrahydro-1,8-naphthyridin-2-yl)ethyl)pyrrolidin-1-yl)butanoic acid |
| 23 | 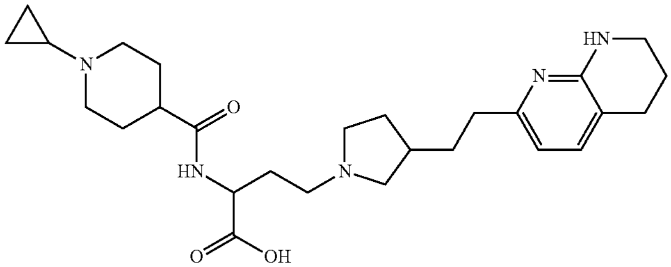 [SMILES: O=C(NC(CCN1CCC(CCc2ccc3c(n2)NCCC3)C1)C(=O)O)C1CCN(C2CC2)CC1] | 2-(1-cyclopropylpiperidine-4-carboxamido)-4-(3-(2-(5,6,7,8-tetrahydro-1,8-naphthyridin-2-yl)ethyl)pyrrolidin-1-yl)butanoic acid |
| 23a | | (S)-2-(1-cyclopropylpiperidine-4-carboxamido)-4-((R)-3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name [1] |
|---|---|---|
| 23b | | (S)-2-(1-cyclopropylpiperidine-4-carboxamido)-4-((S)-3-(2-(5,6,7,8-tetrahydro-1,8-naphthyridin-2-yl)ethyl)pyrrolidin-1-yl)butanoic acid |
| 23c | | (R)-2-(1-cyclopropylpiperidine-4-carboxamido)-4-((R)-3-(2-(5,6,7,8-tetrahydro-1,8-naphthyridin-2-yl)ethyl)pyrrolidin-1-yl)butanoic acid |
| 23d | | (R)-2-(1-cyclopropylpiperidine-4-carboxamido)-4-((S)-3-(2-(5,6,7,8-tetrahydro-1,8-naphthyridin-2-yl)ethyl)pyrrolidin-1-yl)butanoic acid |
| 24 | (structure) | 2-(1-methyl-1H-indazole-6-carboxamido)-4-(3-(2-(5,6,7,8-tetrahydro-1,8-naphthyridin-2-yl)ethyl)pyrrolidin-1-yl)butanoic acid |
| 24a | | (S)-2-(1-methyl-1H-indazole-6-carboxamido)-4-((R)-3-(2-(5,6,7,8-tetrahydro-1,8-naphthyridin-2-yl)ethyl)pyrrolidin-1-yl)butanoic acid |
| 24b | | (S)-2-(1-methyl-1H-indazole-6-carboxamido)-4-((s)-3-(2-(5,6,7,8-tetrahydro-1,8-naphthyridin-2-yl)ethyl)pyrrolidin-1-yl)butanoic acid |
| 24c | | (r)-2-(1-methyl-1H-indazole-6-carboxamido)-4-((R)-3-(2-(5,6,7,8-tetrahydro-1,8-naphthyridin-2-yl)ethyl)pyrrolidin-1-yl)butanoic acid |
| 24d | | (r)-2-(1-methyl-1H-indazole-6-carboxamido)-4-((s)-3-(2-(5,6,7,8-tetrahydro-1,8-naphthyridin-2-yl)ethyl)pyrrolidin-1-yl)butanoic acid |
| 25 | (structure) | 2-(1-methyl-1H-indazole-5-carboxamido)-4-(3-(2-(5,6,7,8-tetrahydro-1,8-naphthyridin-2-yl)ethyl)pyrrolidin-1-yl)butanoic acid |
| 25a | | (S)-2-(1-methyl-1H-indazole-5-carboxamido)-4-((R)-3-(2-(5,6,7,8-tetrahydro-1,8-naphthyridin-2-yl)ethyl)pyrrolidin-1-yl)butanoic acid |
| 25b | | (S)-2-(1-methyl-1H-indazole-5-carboxamido)-4-((S)-3-(2-(5,6,7,8-tetrahydro-1,8-naphthyridin-2-yl)ethyl)pyrrolidin-1-yl)butanoic acid |
| 25c | | (R)-2-(1-methyl-1H-indazole-5-carboxamido)-4-((R)-3-(2-(5,6,7,8-tetrahydro-1,8-naphthyridin-2-yl)ethyl)pyrrolidin-1-yl)butanoic acid |
| 25d | | (R)-2-(1-methyl-1H-indazole-5-carboxamido)-4-((S)-3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name[1] |
|---|---|---|
| 26 | 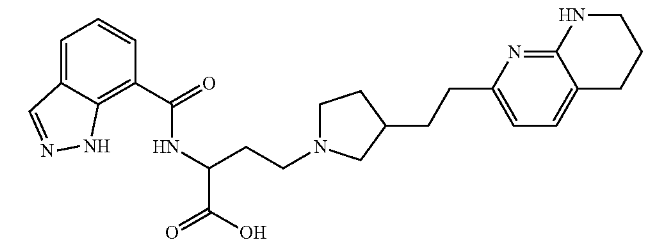 [SMILES: O=C(NC(CCN1CCC(CCc2ccc3c(n2)NCCC3)C1)C(=O)O)c1cccc2cn[nH]c12] | 2-(1H-indazole-7-carboxamido)-4-(3-(2-(5,6,7,8-tetrahydro-1,8-naphthyridin-2-yl)ethyl)pyrrolidin-1-yl)butanoic acid |
| 26a | | (S)-2-(1H-indazole-7-carboxamido)-4-((R)-3-(2-(5,6,7,8-tetrahydro-1,8-naphthyridin-2-yl)ethyl)pyrrolidin-1-yl)butanoic acid |
| 26b | | (S)-2-(1H-indazole-7-carboxamido)-4-((S)-3-(2-(5,6,7,8-tetrahydro-1,8-naphthyridin-2-yl)ethyl)pyrrolidin-1-yl)butanoic acid |
| 26c | | (R)-2-(1H-indazole-7-carboxamido)-4-((R)-3-(2-(5,6,7,8-tetrahydro-1,8-naphthyridin-2-yl)ethyl)pyrrolidin-1-yl)butanoic acid |
| 26d | | (R)-2-(1H-indazole-7-carboxamido)-4-((S)-3-(2-(5,6,7,8-tetrahydro-1,8-naphthyridin-2-yl)ethyl)pyrrolidin-1-yl)butanoic acid |
| 27 | 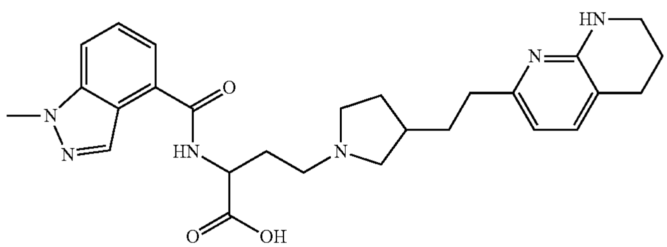 [SMILES: Cn1ncc2c(C(=O)NC(CCN3CCC(CCc4ccc5c(n4)NCCC5)C3)C(=O)O)cccc21] | 2-(1-methyl-1H-indazole-4-carboxamido)-4-(3-(2-(5,6,7,8-tetrahydro-1,8-naphthyridin-2-yl)ethyl)pyrrolidin-1-yl)butanoic acid |
| 27a | | (S)-2-(1-methyl-1H-indazole-4-carboxamido)-4-((R)-3-(2-(5,6,7,8-tetrahydro-1,8-naphthyridin-2-yl)ethyl)pyrrolidin-1-yl)butanoic acid |
| 27b | | (S)-2-(1-methyl-1H-indazole-4-carboxamido)-4-((S)-3-(2-(5,6,7,8-tetrahydro-1,8-naphthyridin-2-yl)ethyl)pyrrolidin-1-yl)butanoic acid |
| 27c | | (R)-2-(1-methyl-1H-indazole-4-carboxamido)-4-((R)-3-(2-(5,6,7,8-tetrahydro-1,8-naphthyridin-2-yl)ethyl)pyrrolidin-1-yl)butanoic acid |
| 27d | | (R)-2-(1-methyl-1H-indazole-4-carboxamido)-4-((S)-3-(2-(5,6,7,8-tetrahydro-1,8-naphthyridin-2-yl)ethyl)pyrrolidin-1-yl)butanoic acid |
| 28 | 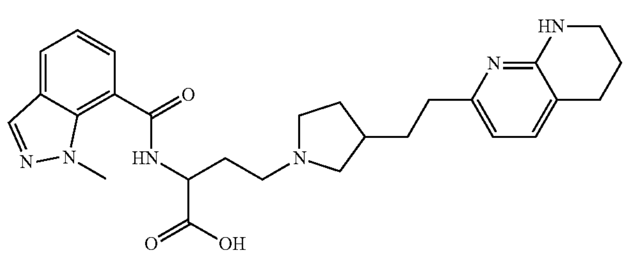 [SMILES: Cn1ncc2cccc(C(=O)NC(CCN3CCC(CCc4ccc5c(n4)NCCC5)C3)C(=O)O)c21] | 2-(1-methyl-1H-indazole-7-carboxamido)-4-(3-(2,5,6,7,8-tetrahydro-1,8-naphthyridin-2-yl)ethyl)pyrrolidin-1-yl)butanoic acid |
| 28a | | (S)-2-(1-methyl-1H-indazole-7-carboxamido)-4-((R)-3-(2-(5,6,7,8-tetrahydro-1,8-naphthyridin-2-yl)ethyl)pyrrolidin-1-yl)butanoic acid |
| 28b | | (S)-2-(1-methyl-1H-indazole-7-carboxamido)-4-((S)-3-(2-(5,6,7,8- |

TABLE 1-continued

| Compound No. | Structure | Chemical Name [1] |
|---|---|---|
| | | tetrahydro-1,8-naphthyridin-2-yl)ethyl)pyrrolidin-1-yl)butanoic acid |
| 28c | | (R)-2-(1-methyl-1H-indazole-7-carboxamido)-4-((R)-3-(2-(5,6,7,8-tetrahydro-1,8-naphthyridin-2-yl)ethyl)pyrrolidin-1-yl)butanoic acid |
| 28d | | (R)-2-(1-methyl-1H-indazole-7-carboxamido)-4-((S)-3-(2-(5,6,7,8-tetrahydro-1,8-naphthyridin-2-yl)ethyl)pyrrolidin-1-yl)butanoic acid |
| 29 | 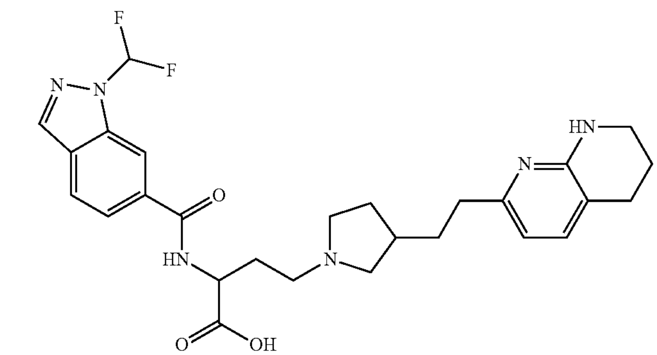 [SMILES: O=C(NC(CCN1CCC(CCc2ccc3c(n2)NCCC3)C1)C(=O)O)c1ccc2cnn(C(F)F)c2c1] | 2-(1-(difluoromethyl)-1H-indazole-6-carboxamido-4-(3-(2-(5,6,7,8-tetrahydro-1,8-naphthyridin-2-yl)ethyl)pyrrolidin-1-yl)butanoic acid |
| 29a | | (S)-2-(1-(difluoromethyl)-1H-indazole-6-carboxamido)-4-((R)-3-(2-(5,6,7,8-tetrahydro-1,8-naphthyridin-2-yl)ethyl)pyrrolidin-1-yl)butanoic acid |
| 29b | | (S)-2-(1-(difluoromethyl)-1H-indazole-6-carboxamido)-4-((S)-3-(2-(5,6,7,8-tetrahydro-1,8-naphthyridin-2-yl)ethyl)pyrrolidin-1-yl)butanoic acid |
| 29c | | (R)-2-(1-(difluoromethyl)-1H-indazole-6-carboxamido)-4-((R)-3-(2-(5,6,7,8-tetrahydro-1,8-naphthyridin-2-yl)ethyl)pyrrolidin-1-yl)butanoic acid |
| 29d | | (R)-2-(1-(difluoromethyl)-1H-indazole-6-carboxamido)-4-((S)-3-(2-(5,6,7,8-tetrahydro-1,8-naphthyridin-2-yl)ethyl)pyrrolidin-1-yl)butanoic acid |
| 30 | 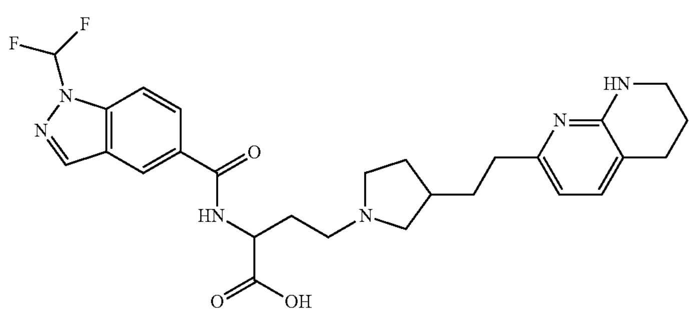 [SMILES: O=C(NC(CCN1CCC(CCc2ccc3c(n2)NCCC3)C1)C(=O)O)c1ccc2c(cnn2C(F)F)c1] | 2-(1-(difluoromethyl)-1H-indazole-5-carboxamido)-4-(3-(2,5,6,7,8-tetrahydro-1,8-naphthyridin-2-yl)ethyl)pyrrolidin-1-yl)butanoic acid |
| 30a | | (S)-2-(1-(difluoromethyl)-1H-indazole-5-carboxamido)-4-((R)-3-(2-(5,6,7,8-tetrahydro-1,8-naphthyridin-2-yl)ethyl)pyrrolidin-1-yl)butanoic acid |
| 30b | | (S)-2-(1-(difluoromethyl)-1H-indazole-5-carboxamido)-4-((S)-3-(2-(5,6,7,8-tetrahydro-1,8-naphthyridin-2-yl)ethyl)pyrrolidin-1-yl)butanoic acid |
| 30c | | (R)-2-(1-(difluoromethyl)-1H-indazole-5-carboxamido)-4-((R)-3-(2-(5,6,7,8-tetrahydro-1,8-naphthyridin-2-yl)ethyl)pyrrolidin-1-yl)butanoic acid |
| 30d | | (R)-2-(1-(difluoromethyl)-1H-indazole-5-carboxamido)-4-((S)-3-(2-(5,6,7,8-tetrahydro-1,8-naphthyridin-2-yl)ethyl)pyrrolidin-1-yl)butanoic acid |

TABLE 1-continued

| Compound No. | Structure | Chemical Name [1] |
|---|---|---|
| 31 | 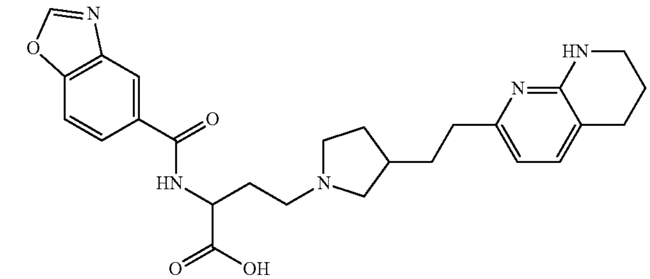 [SMILES: O=C(NC(CCN1CCC(CCc2ccc3c(n2)NCCC3)C1)C(=O)O)c1ccc2ocnc2c1] | 2-(benzo[d]oxazole-5-carboxamido)-4-(3-(2-(5,6,7,8-tetrahydro-1,8-naphthyridin-2-yl)ethyl)pyrrolidin-1-yl)butanoic acid |
| 31a | | (S)-2-(benzo[d]oxazole-5-carboxamido)-4-((R)-3-(2-(5,6,7,8-tetrahydro-1,8-naphthyridin-2-yl)ethyl)pyrrolidin-1-yl)butanoic acid |
| 31b | | (S)-2-(benzo[d]oxazole-5-carboxamido)-4-((S)-3-(2-(5,6,7,8-tetrahydro-1,8-naphthyridin-2-yl)ethyl)pyrrolidin-1-yl)butanoic acid |
| 31c | | (R)-2-(benzo[d]oxazole-5-carboxamido)-4-((R)-3-(2-(5,6,7,8-tetrahydro-1,8-naphthyridin-2-yl)ethyl)pyrrolidin-1-yl)butanoic acid |
| 31d | | (R)-2-(benzo[d]oxazole-5-carboxamido)-4-((S)-3-(2-(5,6,7,8-tetrahydro-1,8-naphthyridin-2-yl)ethyl)pyrrolidin-1-yl)butanoic acid |

[1] Chemical names are generated using the ChemBioDraw® Ultra version 14.0.0.117 software.

Additional representative compounds are listed in Table 1-A.

| Compound No. | Structure |
|---|---|
| 32 | 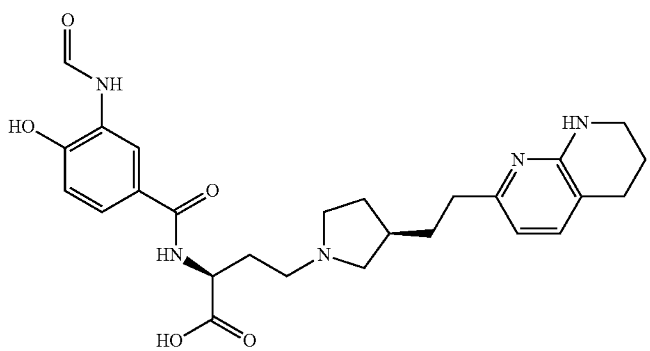 [SMILES: O=CNc1cc(C(=O)N[C@@H](CCN2CC[C@@H](CCc3ccc4c(n3)NCCC4)C2)C(=O)O)ccc1O] |
| 33 | 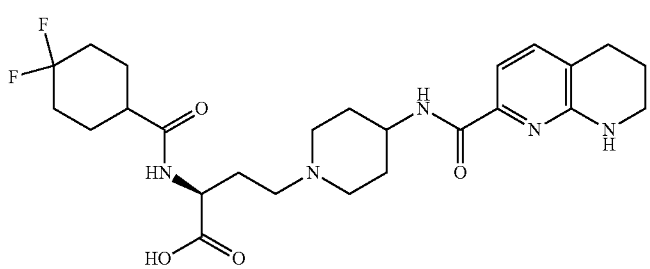 [SMILES: O=C(NC1CCN(CC[C@H](NC(=O)C2CCC(F)(F)CC2)C(=O)O)CC1)c1ccc2c(n1)NCCC2] |

-continued
| Compound No. | Structure |
|---|---|
| 34 | 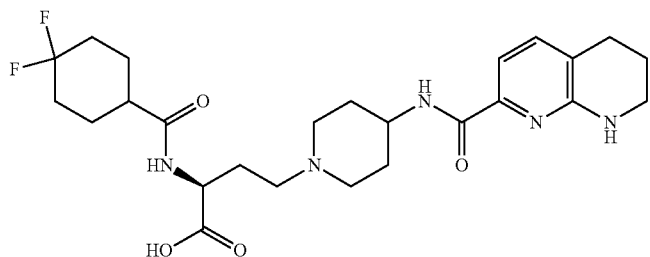 |
| 35 | 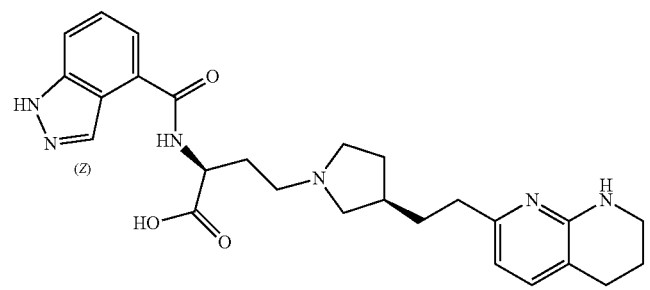 [SMILES: O=C(N[C@@H](CCN1CC[C@@H](CCc2ccc3c(n2)NCCC3)C1)C(=O)O)c1cccc2[nH]ncc12] |
| 36 | 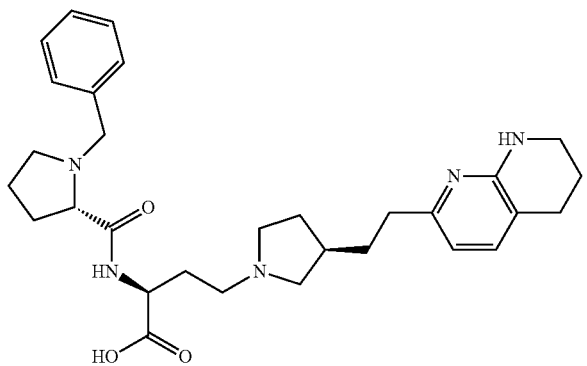 [SMILES: O=C(O)[C@H](CCN1CC[C@@H](CCc2ccc3c(n2)NCCC3)C1)NC(=O)[C@@H]1CCCN1Cc1ccccc1] |
| 37 | 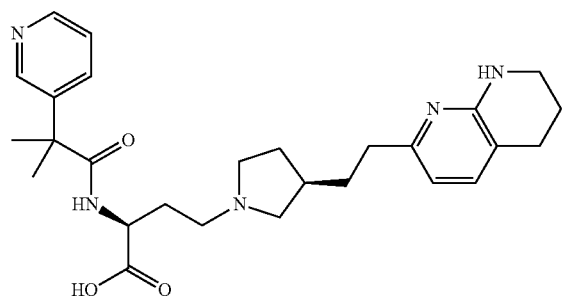 |
| 38 | 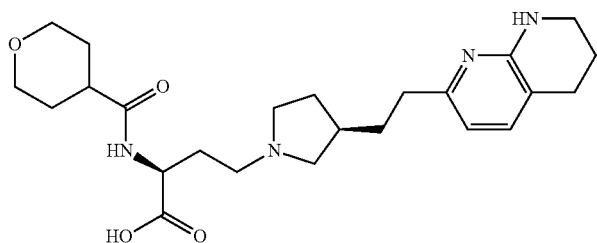 [SMILES: O=C(N[C@@H](CCN1CC[C@@H](CCc2ccc3c(n2)NCCC3)C1)C(=O)O)C1CCOCC1] |

| Compound No. | Structure |
|---|---|
| 39 | 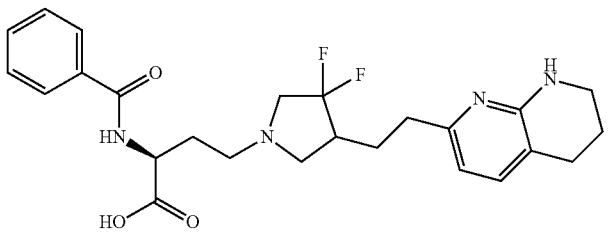 [SMILES: O=C(N[C@@H](CCN1CC(CCc2ccc3c(n2)NCCC3)C(F)(F)C1)C(=O)O)c1ccccc1] |
| 40 | 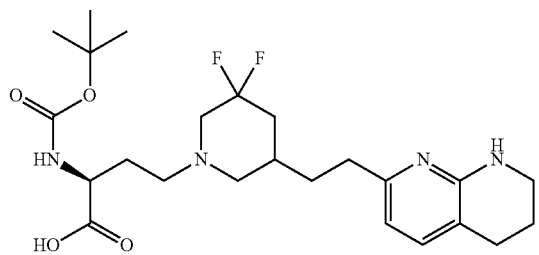 [SMILES: CC(C)(C)OC(=O)N[C@@H](CCN1CC(CCc2ccc3c(n2)NCCC3)CC(F)(F)C1)C(=O)O] |
| 41 | 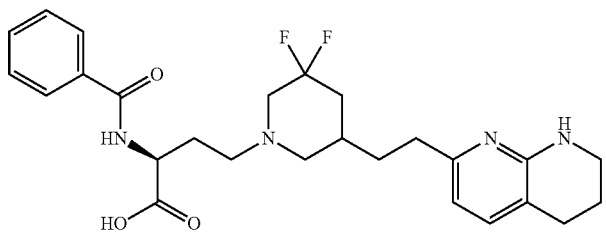 [SMILES: O=C(N[C@@H](CCN1CC(CCc2ccc3c(n2)NCCC3)CC(F)(F)C1)C(=O)O)c1ccccc1] |
| 42 | 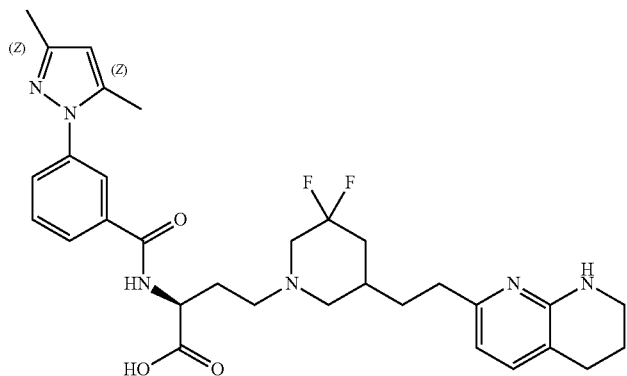 [SMILES: Cc1cc(C)n(-c2cccc(C(=O)N[C@@H](CCN3CC(CCc4ccc5c(n4)NCCC5)CC(F)(F)C3)C(=O)O)c2)n1] |
| 43 | 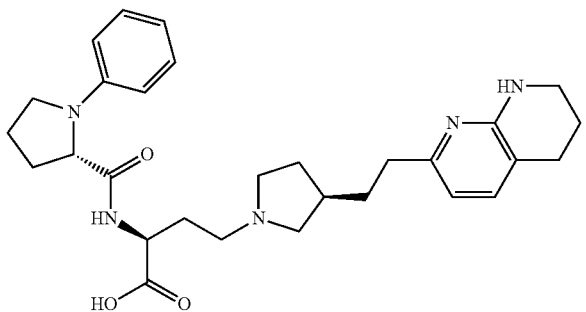 [SMILES: O=C(O)[C@H](CCN1CC[C@@H](CCc2ccc3c(n2)NCCC3)C1)NC(=O)[C@@H]1CCCN1c1ccccc1] |

| Compound No. | Structure |
|---|---|
| 44 | 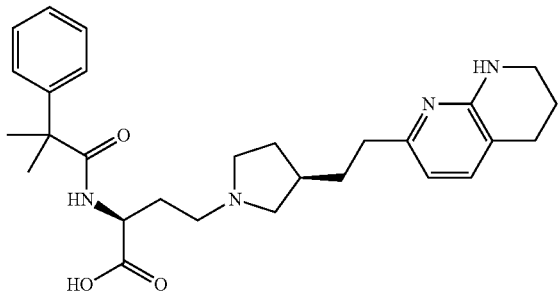 [SMILES: CC(C)(C(=O)N[C@@H](CCN1CC[C@@H](CCc2ccc3c(n2)NCCC3)C1)C(=O)O)c1ccccc1] |
| 45 | 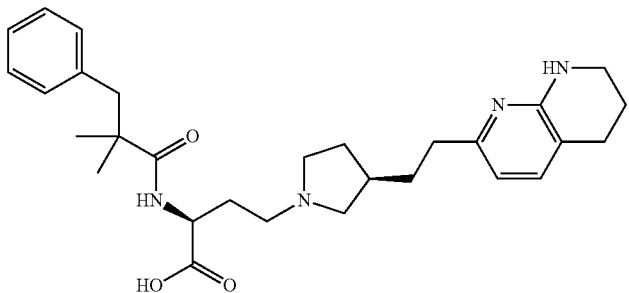 [SMILES: CC(C)(Cc1ccccc1)C(=O)N[C@@H](CCN1CC[C@@H](CCc2ccc3c(n2)NCCC3)C1)C(=O)O] |
| 46 | 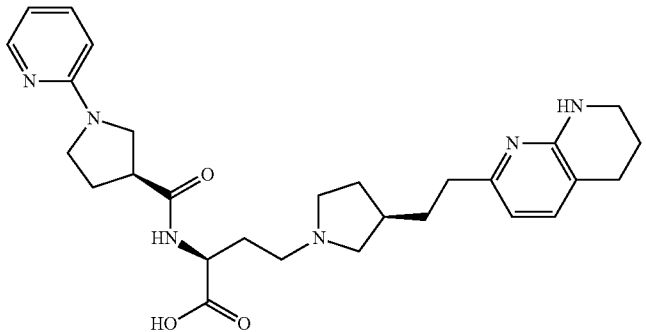 [SMILES: O=C(N[C@@H](CCN1CC[C@@H](CCc2ccc3c(n2)NCCC3)C1)C(=O)O)[C@H]1CCN(c2ccccn2)C1] |
| 47 | 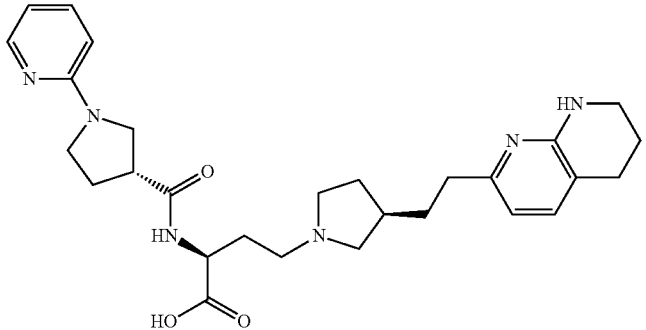 [SMILES: O=C(N[C@@H](CCN1CC[C@@H](CCc2ccc3c(n2)NCCC3)C1)C(=O)O)[C@@H]1CCN(c2ccccn2)C1] |

-continued
| Compound No. | Structure |
|---|---|
| 48 | 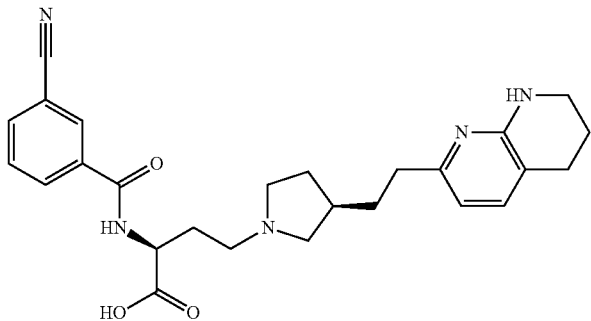 [SMILES: N#Cc1cccc(C(=O)N[C@@H](CCN2CC[C@@H](CCc3ccc4c(n3)NCCC4)C2)C(=O)O)c1] |
| 49 | 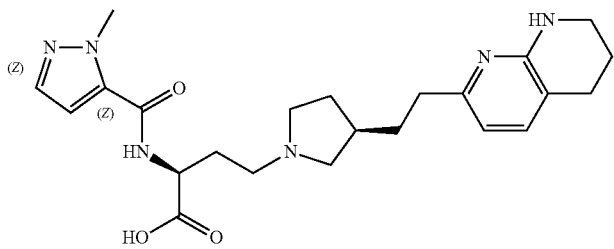 [SMILES: Cn1nccc1C(=O)N[C@@H](CCN1CC[C@@H](CCc2ccc3c(n2)NCCC3)C1)C(=O)O] |
| 50 | 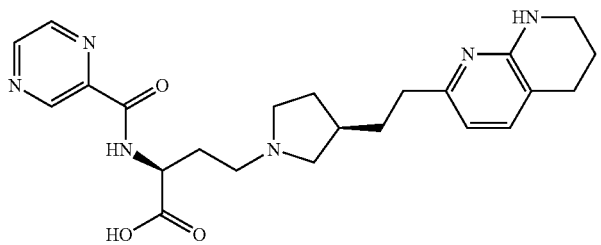 [SMILES: O=C(N[C@@H](CCN1CC[C@@H](CCc2ccc3c(n2)NCCC3)C1)C(=O)O)c1cnccn1] |
| 51 | 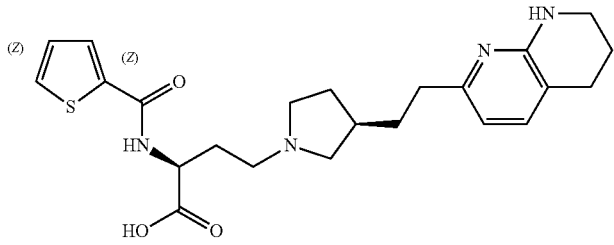 [SMILES: O=C(N[C@@H](CCN1CC[C@@H](CCc2ccc3c(n2)NCCC3)C1)C(=O)O)c1cccs1] |
| 52 | 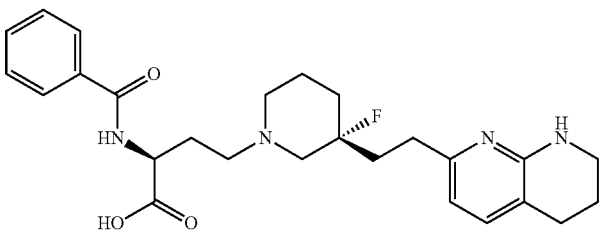 [SMILES: O=C(N[C@@H](CCN1CCC[C@@](F)(CCc2ccc3c(n2)NCCC3)C1)C(=O)O)c1ccccc1] |

-continued
| Compound No. | Structure |
|---|---|
| 53 | 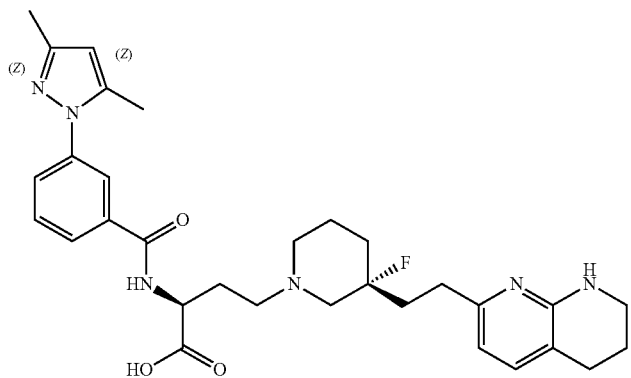 [SMILES: Cc1cc(C)n(-c2cccc(C(=O)N[C@@H](CCN3CCC[C@@](F)(CCc4ccc5c(n4)NCCC5)C3)C(=O)O)c2)n1] |
| 54 | 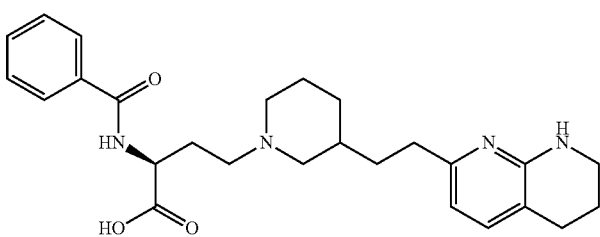 [SMILES: O=C(N[C@@H](CCN1CCCC(CCc2ccc3c(n2)NCCC3)C1)C(=O)O)c1ccccc1] |
| 55 | 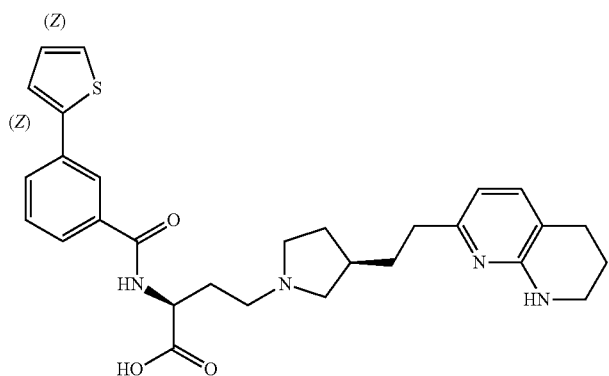 [SMILES: O=C(N[C@@H](CCN1CC[C@@H](CCc2ccc3c(n2)NCCC3)C1)C(=O)O)c1cccc(-c2cccs2)c1] |
| 56 | 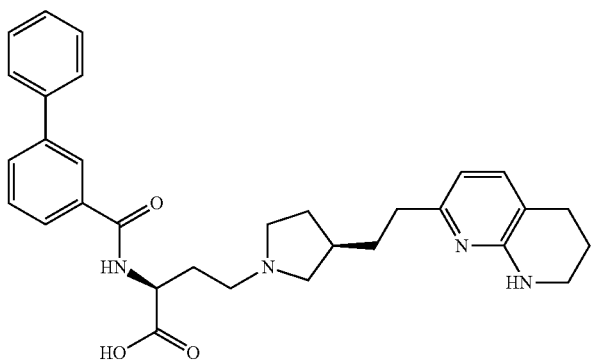 [SMILES: O=C(N[C@@H](CCN1CC[C@@H](CCc2ccc3c(n2)NCCC3)C1)C(=O)O)c1cccc(-c2ccccc2)c1] |

| Compound No. | Structure |
|---|---|
| 57 | 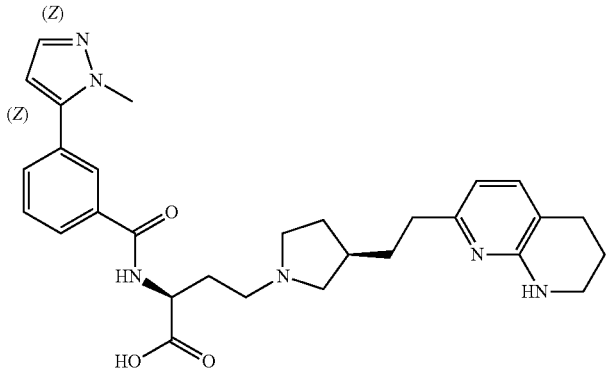 [SMILES: Cn1nccc1-c1cccc(C(=O)N[C@@H](CCN2CC[C@@H](CCc3ccc4c(n3)NCCC4)C2)C(=O)O)c1] |
| 58 | 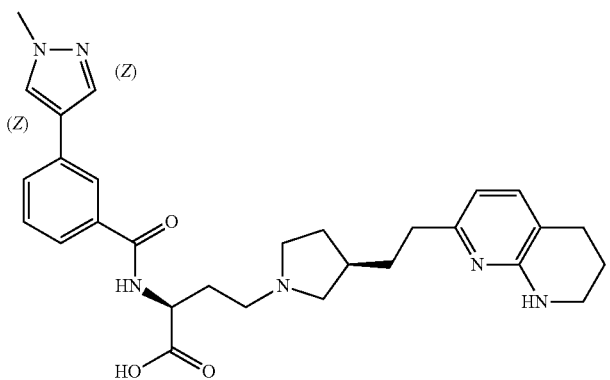 [SMILES: Cn1cc(-c2cccc(C(=O)N[C@@H](CCN3CC[C@@H](CCc4ccc5c(n4)NCCC5)C3)C(=O)O)c2)cn1] |
| 59 | 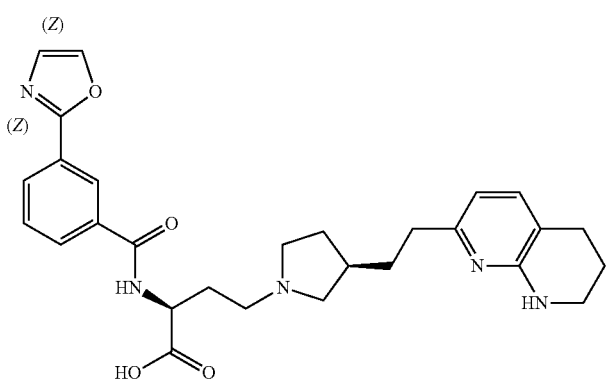 |
| 60 | 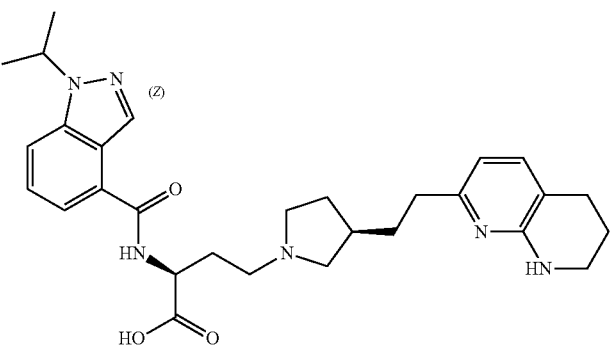 [SMILES: CC(C)n1ncc2c(C(=O)N[C@@H](CCN3CC[C@@H](CCc4ccc5c(n4)NCCC5)C3)C(=O)O)cccc21] |

-continued

| Compound No. | Structure |
|---|---|
| 61 | *(structure of compound 61)* |
| 62 | *(structure of compound 62)* |
| 63 | *(structure of compound 63)* |
| 64 | *(structure of compound 64)* |
| 65 | *(structure of compound 65)* |

-continued

| Compound No. | Structure |
|---|---|
| 66 | *(structure: 3-(thiazol-5-yl)benzamide linked via HN to a chiral carbon bearing COOH and a CH2CH2 chain to a pyrrolidine substituted with ethyl-(5,6,7,8-tetrahydro-1,8-naphthyridin-2-yl))* |
| 67 | *(structure: 2,3-difluorobenzamide linked via HN to a chiral carbon bearing COOH and ethylene chain to pyrrolidine substituted with ethyl-(5,6,7,8-tetrahydro-1,8-naphthyridin-2-yl))* |
| 68 | *(structure: 3-tert-butylbenzamide linked via HN to a chiral carbon bearing COOH and ethylene chain to pyrrolidine substituted with ethyl-(5,6,7,8-tetrahydro-1,8-naphthyridin-2-yl))* |
| 69 | *(structure: 1-methyl-1H-pyrazole-4-carboxamide linked via HN to a chiral carbon bearing COOH and ethylene chain to pyrrolidine substituted with ethyl-(5,6,7,8-tetrahydro-1,8-naphthyridin-2-yl))* |
| 70 | *(structure: pyrimidine-4-carboxamide linked via HN to a chiral carbon bearing COOH and ethylene chain to pyrrolidine substituted with ethyl-(5,6,7,8-tetrahydro-1,8-naphthyridin-2-yl))* |

| Compound No. | Structure |
|---|---|
| 71 | 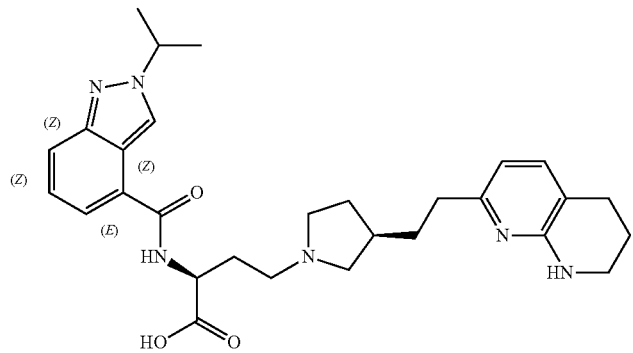 [SMILES: CC(C)n1cc2c(C(=O)N[C@@H](CCN3CC[C@@H](CCc4ccc5c(n4)NCCC5)C3)C(=O)O)cccc2n1] |
| 72 | 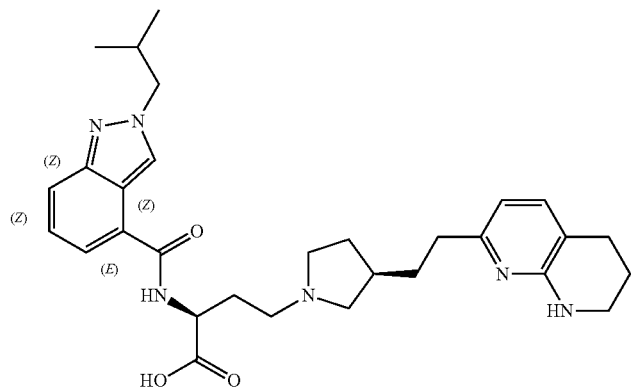 [SMILES: CC(C)Cn1cc2c(C(=O)N[C@@H](CCN3CC[C@@H](CCc4ccc5c(n4)NCCC5)C3)C(=O)O)cccc2n1] |
| 73 | 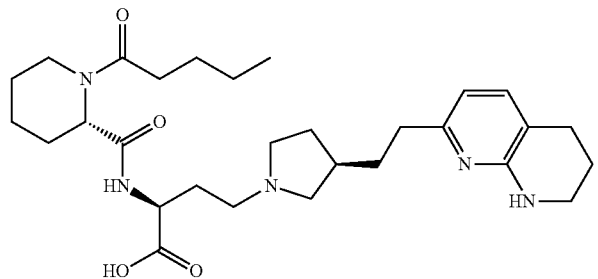 [SMILES: CCCCC(=O)N1CCCC[C@H]1C(=O)N[C@@H](CCN1CC[C@@H](CCc2ccc3c(n2)NCCC3)C1)C(=O)O] |
| 74 | 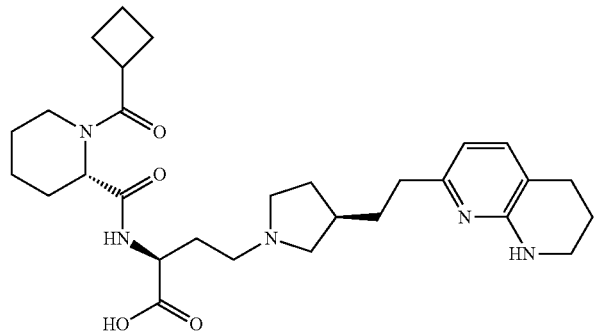 [SMILES: O=C(O)[C@H](CCN1CC[C@@H](CCc2ccc3c(n2)NCCC3)C1)NC(=O)[C@@H]1CCCCN1C(=O)C1CCC1] |

| Compound No. | Structure |
|---|---|
| 75 | 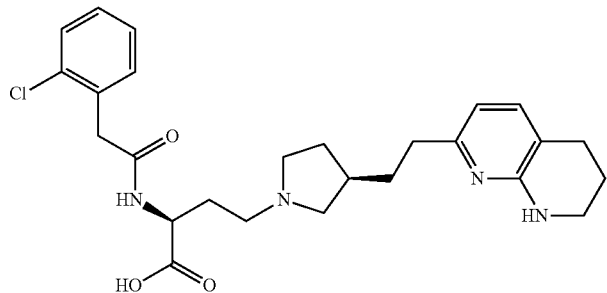 [SMILES: O=C(Cc1ccccc1Cl)N[C@@H](CCN1CC[C@@H](CCc2ccc3c(n2)NCCC3)C1)C(=O)O] |
| 76 | 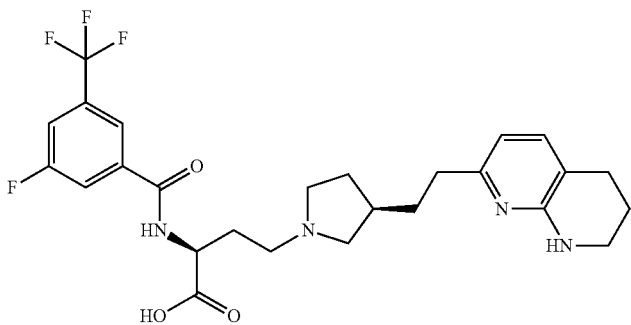 [SMILES: O=C(N[C@@H](CCN1CC[C@@H](CCc2ccc3c(n2)NCCC3)C1)C(=O)O)c1cc(F)cc(C(F)(F)F)c1] |
| 77 | 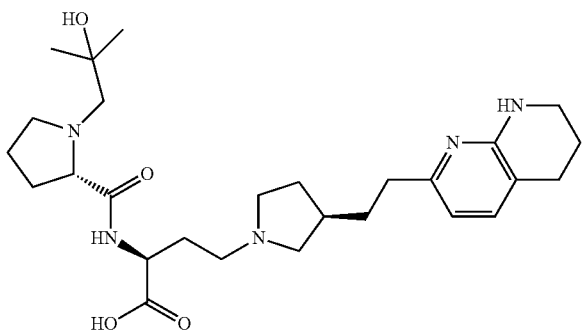 [SMILES: CC(C)(O)CN1CCC[C@H]1C(=O)N[C@@H](CCN1CC[C@@H](CCc2ccc3c(n2)NCCC3)C1)C(=O)O] |
| 78 | 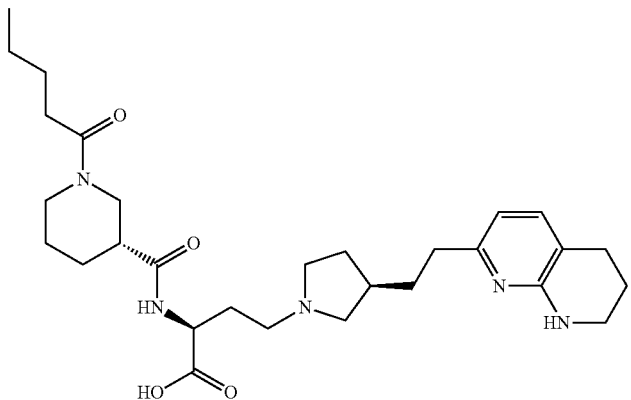 [SMILES: CCCCC(=O)N1CCC[C@@H](C(=O)N[C@@H](CCN2CC[C@@H](CCc3ccc4c(n3)NCCC4)C2)C(=O)O)C1] |

| Compound No. | Structure |
|---|---|
| 79 | 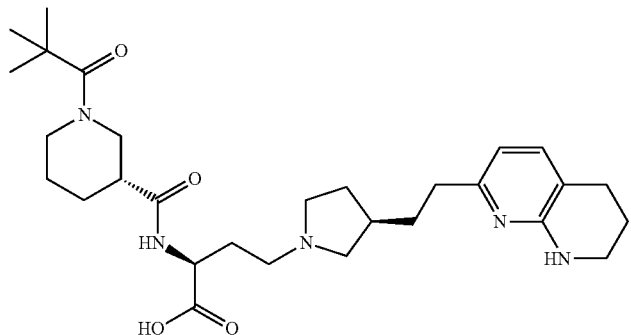 [SMILES: CC(C)(C)C(=O)N1CCC[C@@H](C(=O)N[C@@H](CCN2CC[C@@H](CCc3ccc4c(n3)NCCC4)C2)C(=O)O)C1] |
| 80 | 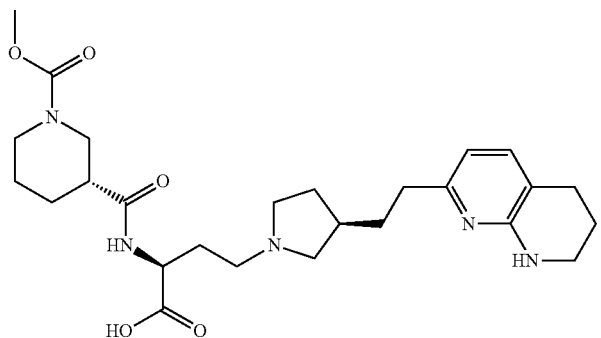 [SMILES: COC(=O)N1CCC[C@@H](C(=O)N[C@@H](CCN2CC[C@@H](CCc3ccc4c(n3)NCCC4)C2)C(=O)O)C1] |
| 81 | 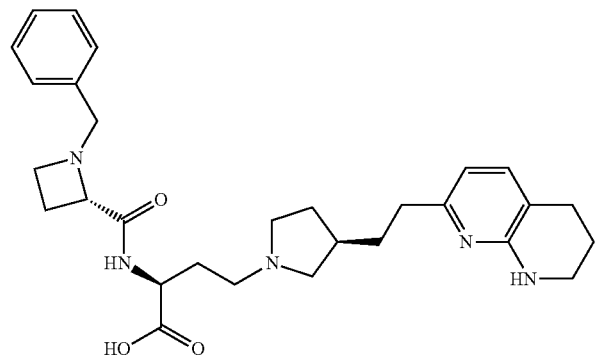 [SMILES: O=C(O)[C@H](CCN1CC[C@@H](CCc2ccc3c(n2)NCCC3)C1)NC(=O)[C@@H]1CCN1Cc1ccccc1] |
| 82 | 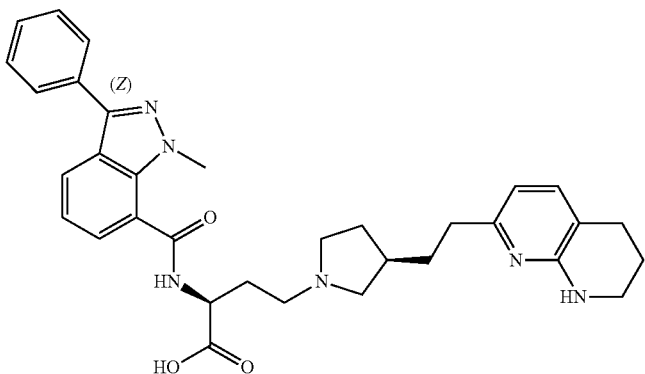 [SMILES: Cn1nc(-c2ccccc2)c2cccc(C(=O)N[C@@H](CCN3CC[C@@H](CCc4ccc5c(n4)NCCC5)C3)C(=O)O)c21] |

| Compound No. | Structure |
|---|---|
| 83 | 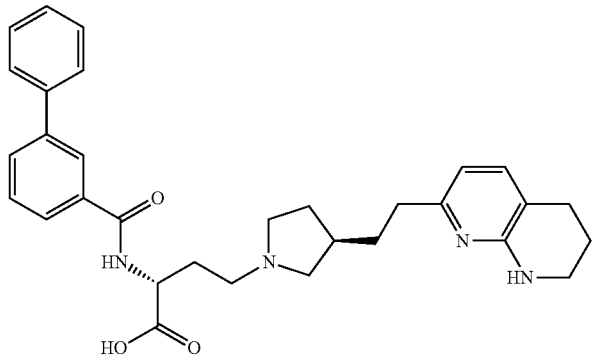 [SMILES: O=C(N[C@H](CCN1CC[C@@H](CCc2ccc3c(n2)NCCC3)C1)C(=O)O)c1cccc(-c2ccccc2)c1] |
| 84 | 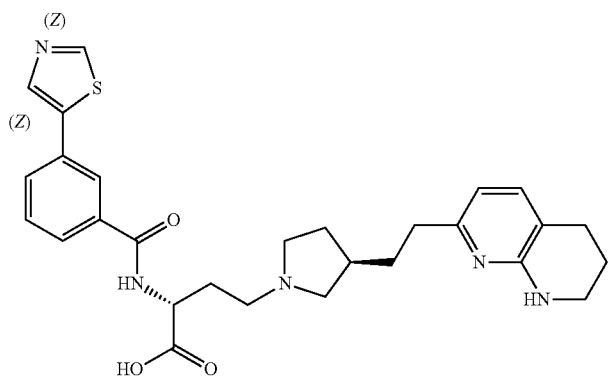 [SMILES: O=C(N[C@H](CCN1CC[C@@H](CCc2ccc3c(n2)NCCC3)C1)C(=O)O)c1cccc(-c2cncs2)c1] |
| 85 | 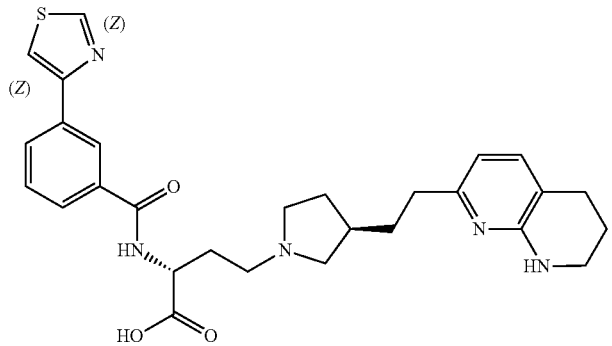 [SMILES: O=C(N[C@H](CCN1CC[C@@H](CCc2ccc3c(n2)NCCC3)C1)C(=O)O)c1cccc(-c2cscn2)c1] |
| 86 | 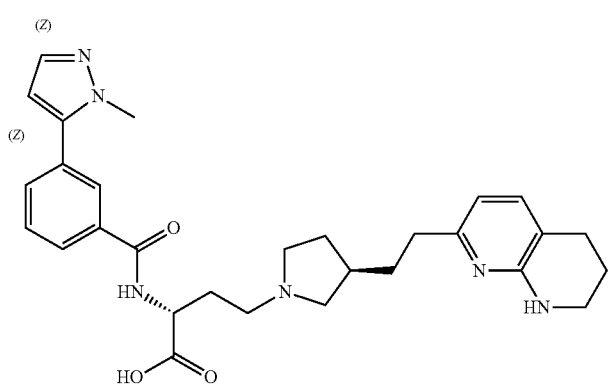 [SMILES: Cn1nccc1-c1cccc(C(=O)N[C@H](CCN2CC[C@@H](CCc3ccc4c(n3)NCCC4)C2)C(=O)O)c1] |

-continued

| Compound No. | Structure |
|---|---|
| 87 | 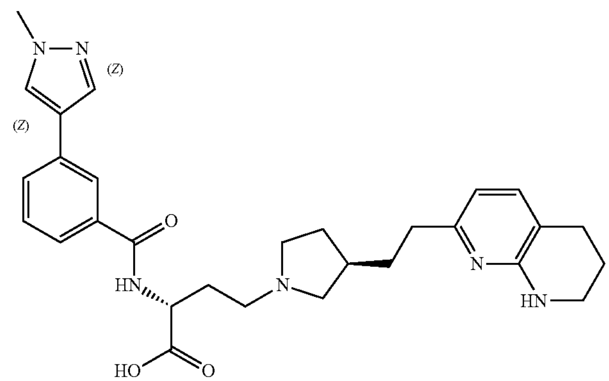 [SMILES: Cn1cc(-c2cccc(C(=O)N[C@H](CCN3CC[C@@H](CCc4ccc5c(n4)NCCC5)C3)C(=O)O)c2)cn1] |
| 88 | 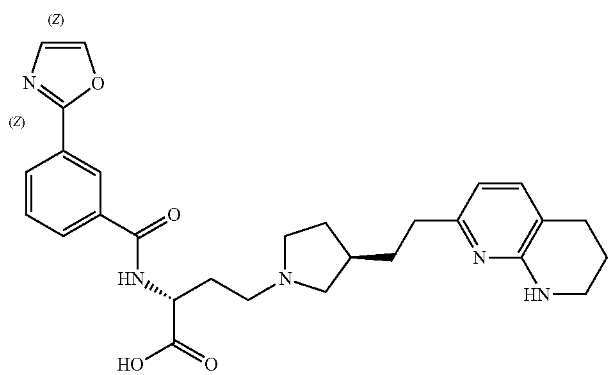 [SMILES: O=C(N[C@H](CCN1CC[C@@H](CCc2ccc3c(n2)NCCC3)C1)C(=O)O)c1cccc(-c2ncco2)c1] |
| 89 | 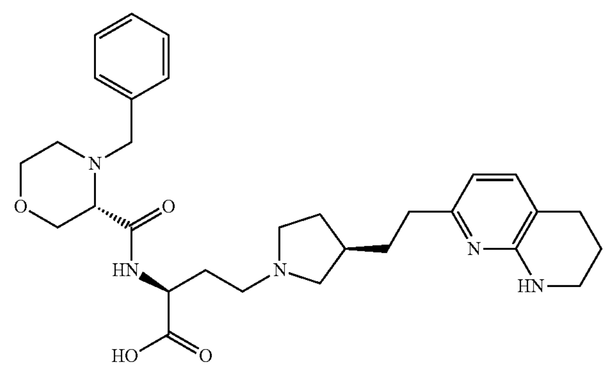 [SMILES: O=C(O)[C@H](CCN1CC[C@@H](CCc2ccc3c(n2)NCCC3)C1)NC(=O)[C@@H]1COCCN1Cc1ccccc1] |
| 90 | 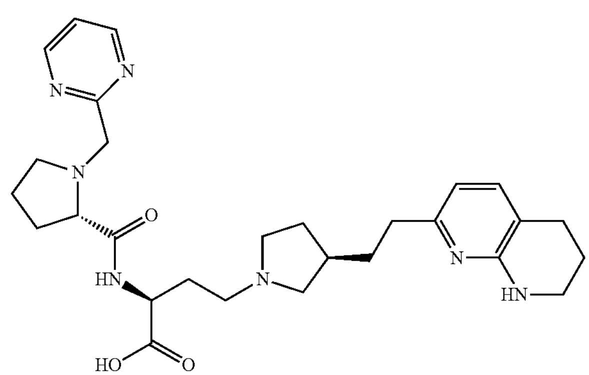 [SMILES: O=C(O)[C@H](CCN1CC[C@@H](CCc2ccc3c(n2)NCCC3)C1)NC(=O)[C@@H]1CCCN1Cc1ncccn1] |

| Compound No. | Structure |
|---|---|
| 91 | 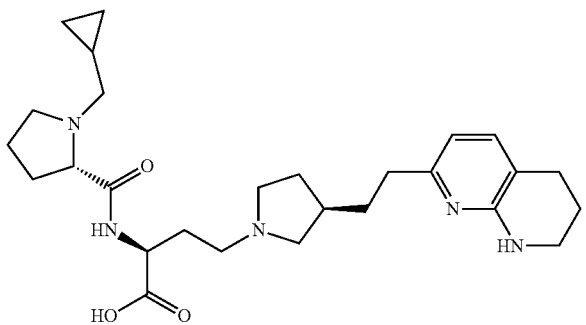 [SMILES: O=C(O)[C@H](CCN1CC[C@@H](CCc2ccc3c(n2)NCCC3)C1)NC(=O)[C@@H]1CCCN1CC1CC1] |
| 92 | 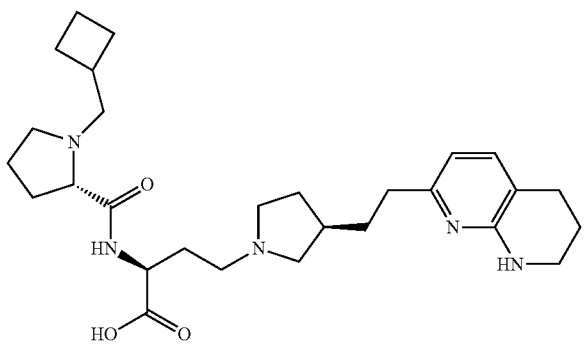 [SMILES: O=C(O)[C@H](CCN1CC[C@@H](CCc2ccc3c(n2)NCCC3)C1)NC(=O)[C@@H]1CCCN1CC1CCC1] |
| 93 | 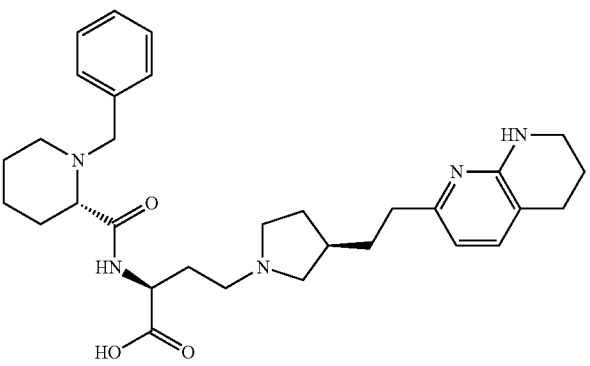 [SMILES: O=C(O)[C@H](CCN1CC[C@@H](CCc2ccc3c(n2)NCCC3)C1)NC(=O)[C@@H]1CCCCN1Cc1ccccc1] |
| 94 | 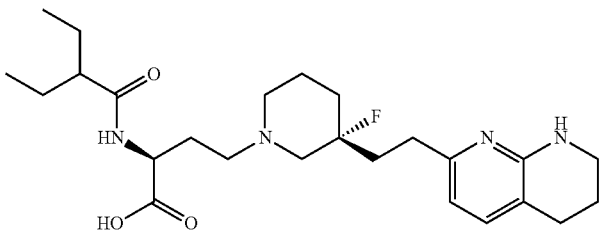 [SMILES: CCC(CC)C(=O)N[C@@H](CCN1CCC[C@@](F)(CCc2ccc3c(n2)NCCC3)C1)C(=O)O] |
| 95 | 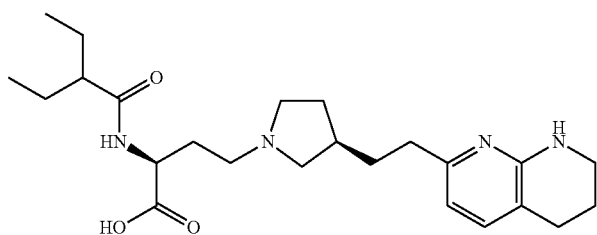 [SMILES: CCC(CC)C(=O)N[C@@H](CCN1CC[C@@H](CCc2ccc3c(n2)NCCC3)C1)C(=O)O] |

| Compound No. | Structure |
|---|---|
| 96 | 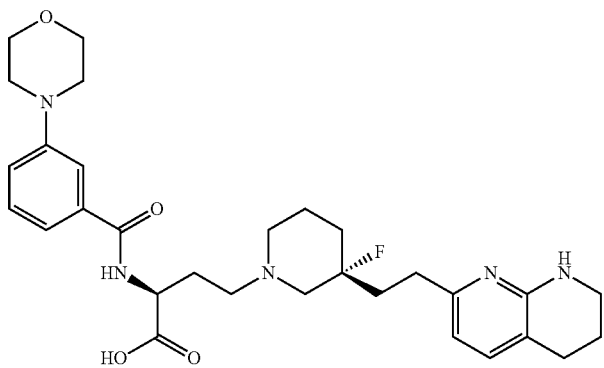 [SMILES: O=C(N[C@@H](CCN1CCC[C@@](F)(CCc2ccc3c(n2)NCCC3)C1)C(=O)O)c1cccc(N2CCOCC2)c1] |
| 97 | 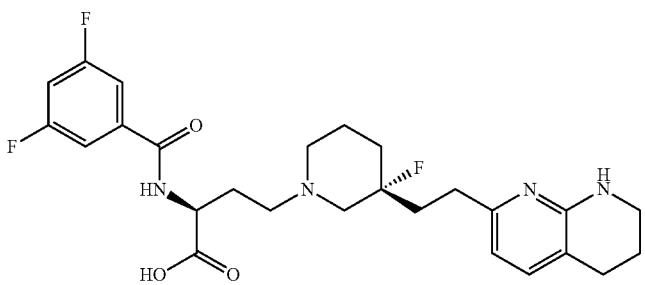 [SMILES: O=C(N[C@@H](CCN1CCC[C@@](F)(CCc2ccc3c(n2)NCCC3)C1)C(=O)O)c1cc(F)cc(F)c1] |
| 98 | 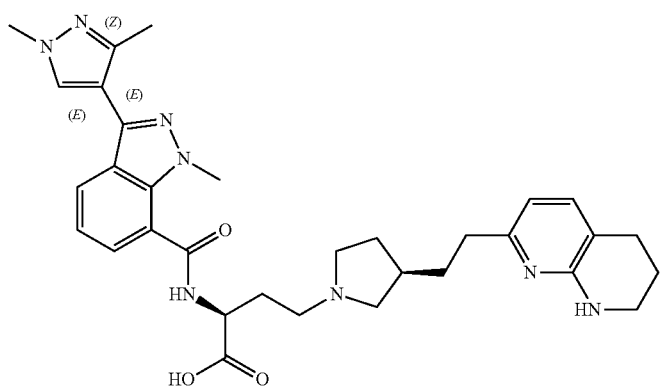 [SMILES: Cc1nn(C)cc1-c1nn(C)c2c(C(=O)N[C@@H](CCN3CC[C@@H](CCc4ccc5c(n4)NCCC5)C3)C(=O)O)cccc12] |
| 99 | 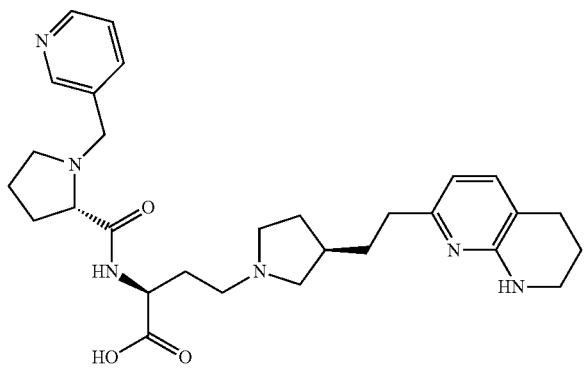 [SMILES: O=C(O)[C@H](CCN1CC[C@@H](CCc2ccc3c(n2)NCCC3)C1)NC(=O)[C@@H]1CCCN1Cc1cccnc1] |

| Compound No. | Structure |
|---|---|
| 100 | 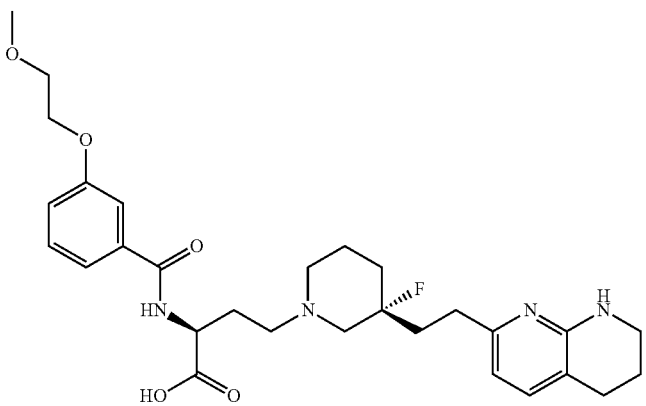 [SMILES: COCCOc1cccc(C(=O)N[C@@H](CCN2CCC[C@@](F)(CCc3ccc4c(n3)NCCC4)C2)C(=O)O)c1] |
| 101 | 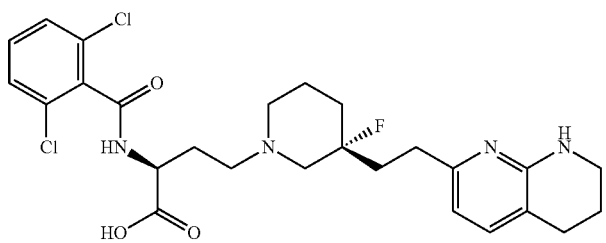 [SMILES: O=C(N[C@@H](CCN1CCC[C@@](F)(CCc2ccc3c(n2)NCCC3)C1)C(=O)O)c1c(Cl)cccc1Cl] |
| 102 | 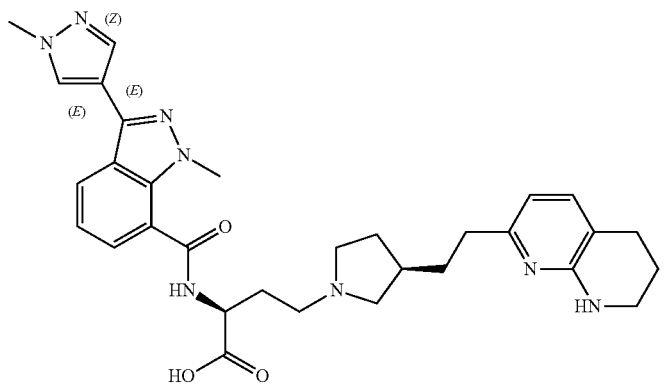 [SMILES: Cn1cc(-c2nn(C)c3c(C(=O)N[C@@H](CCN4CC[C@@H](CCc5ccc6c(n5)NCCC6)C4)C(=O)O)cccc23)cn1] |
| 103 | 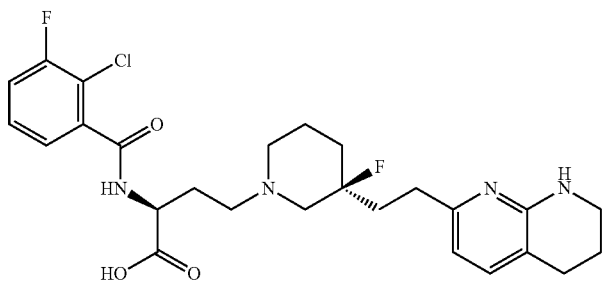 [SMILES: O=C(N[C@@H](CCN1CCC[C@](F)(CCc2ccc3c(n2)NCCC3)C1)C(=O)O)c1cccc(F)c1Cl] |

| Compound No. | Structure |
|---|---|
| 104 | 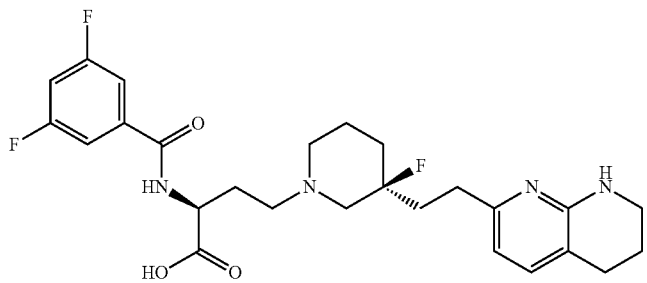 [SMILES: O=C(N[C@@H](CCN1CCC[C@](F)(CCc2ccc3c(n2)NCCC3)C1)C(=O)O)c1cc(F)cc(F)c1] |
| 105 | 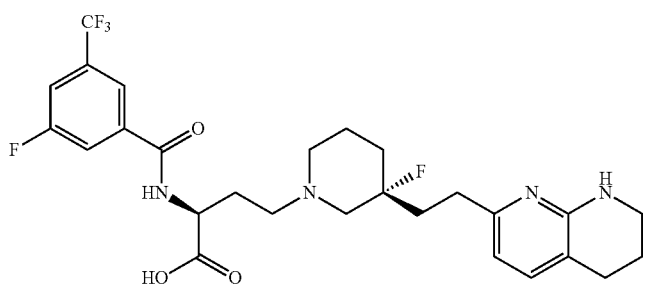 [SMILES: O=C(N[C@@H](CCN1CCC[C@@](F)(CCc2ccc3c(n2)NCCC3)C1)C(=O)O)c1cc(F)cc(C(F)(F)F)c1] |
| 106 | 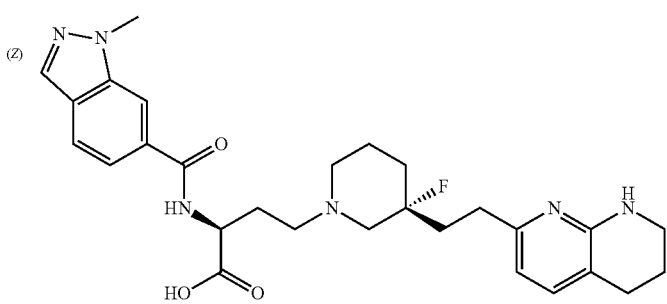 [SMILES: Cn1ncc2ccc(C(=O)N[C@@H](CCN3CCC[C@@](F)(CCc4ccc5c(n4)NCCC5)C3)C(=O)O)cc21] |
| 107 | 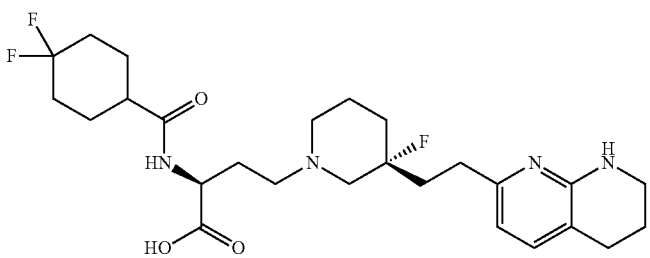 [SMILES: O=C(N[C@@H](CCN1CCC[C@@](F)(CCc2ccc3c(n2)NCCC3)C1)C(=O)O)C1CCC(F)(F)CC1] |
| 108 | 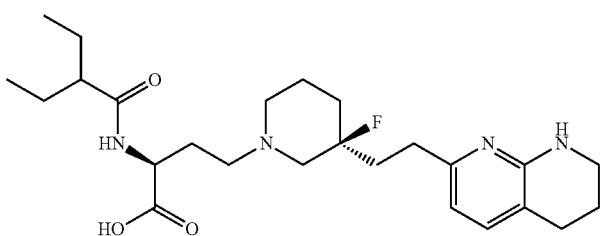 [SMILES: CCC(CC)C(=O)N[C@@H](CCN1CCC[C@](F)(CCc2ccc3c(n2)NCCC3)C1)C(=O)O] |

-continued
| Compound No. | Structure |
|---|---|
| 109 | 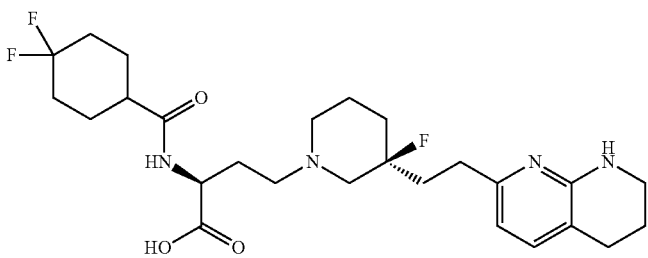 [SMILES: O=C(N[C@@H](CCN1CCC[C@](F)(CCc2ccc3c(n2)NCCC3)C1)C(=O)O)C1CCC(F)(F)CC1] |
| 110 | 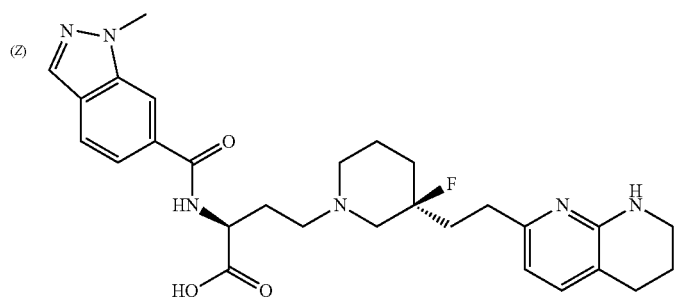 [SMILES: Cn1ncc2ccc(C(=O)N[C@@H](CCN3CCC[C@](F)(CCc4ccc5c(n4)NCCC5)C3)C(=O)O)cc21] |
| 111 | 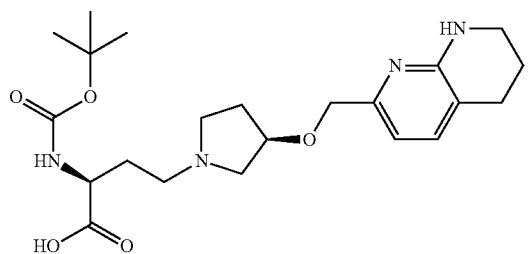 [SMILES: CC(C)(C)OC(=O)N[C@@H](CCN1CC[C@@H](OCc2ccc3c(n2)NCCC3)C1)C(=O)O] |
| 112 | 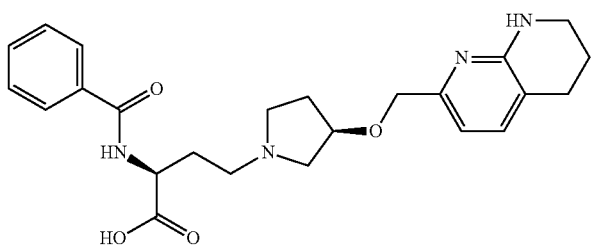 [SMILES: O=C(N[C@@H](CCN1CC[C@@H](OCc2ccc3c(n2)NCCC3)C1)C(=O)O)c1ccccc1] |
| 113 | 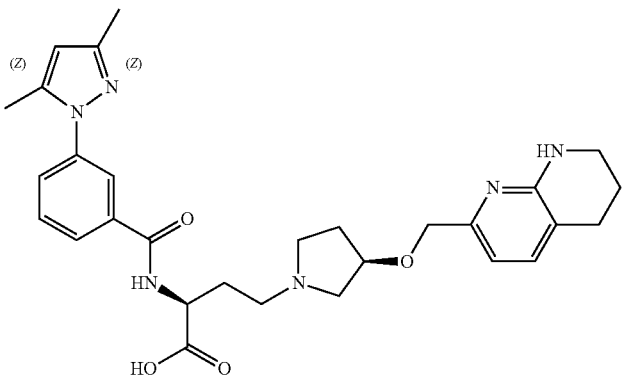 [SMILES: Cc1cc(C)n(-c2cccc(C(=O)N[C@@H](CCN3CC[C@@H](OCc4ccc5c(n4)NCCC5)C3)C(=O)O)c2)n1] |

-continued
| Compound No. | Structure |
|---|---|
| 114 | 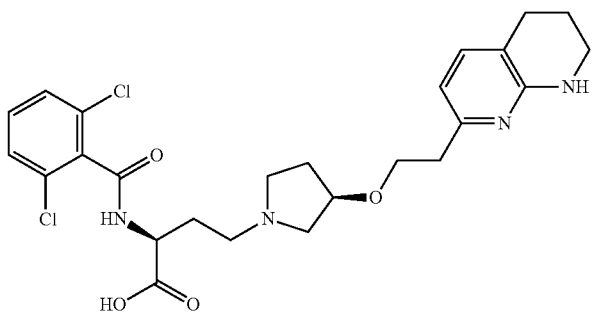 [SMILES: O=C(N[C@@H](CCN1CC[C@@H](OCCc2ccc3c(n2)NCCC3)C1)C(=O)O)c1c(Cl)cccc1Cl] |
| 115 | 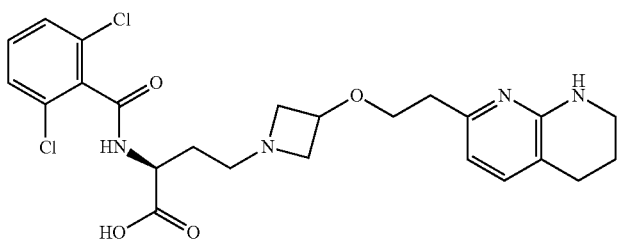 [SMILES: O=C(N[C@@H](CCN1CC(OCCc2ccc3c(n2)NCCC3)C1)C(=O)O)c1c(Cl)cccc1Cl] |
| 116 | 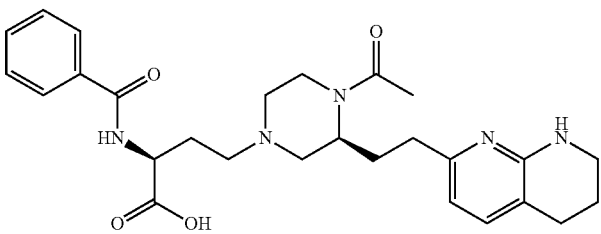 [SMILES: CC(=O)N1CCN(CC[C@H](NC(=O)c2ccccc2)C(=O)O)C[C@@H]1CCc1ccc2c(n1)NCCC2] |
| 117 | 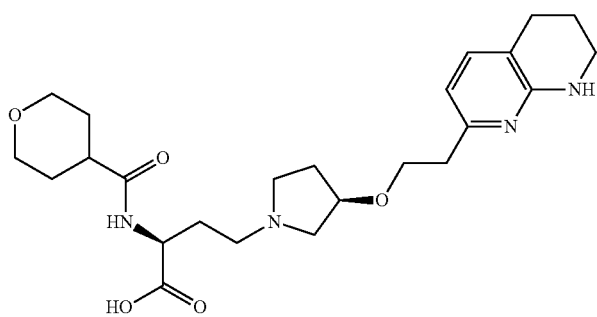 [SMILES: O=C(N[C@@H](CCN1CC[C@@H](OCCc2ccc3c(n2)NCCC3)C1)C(=O)O)C1CCOCC1] |
| 118 | 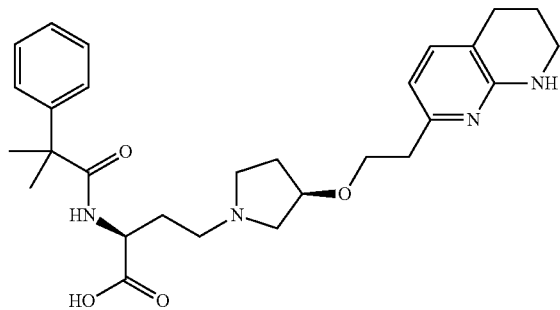 [SMILES: CC(C)(C(=O)N[C@@H](CCN1CC[C@@H](OCCc2ccc3c(n2)NCCC3)C1)C(=O)O)c1ccccc1] |

-continued
| Compound No. | Structure |
|---|---|
| 119 | 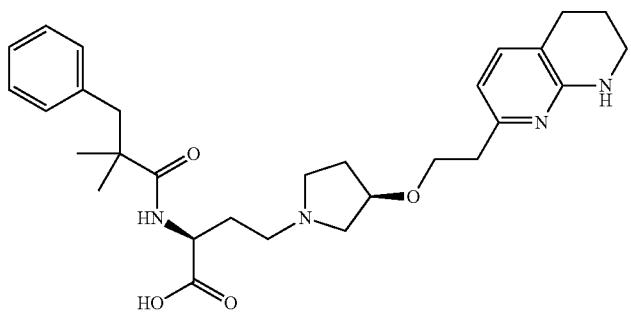 [SMILES: CC(C)(Cc1ccccc1)C(=O)N[C@@H](CCN1CC[C@@H](OCCc2ccc3c(n2)NCCC3)C1)C(=O)O] |
| 120 | 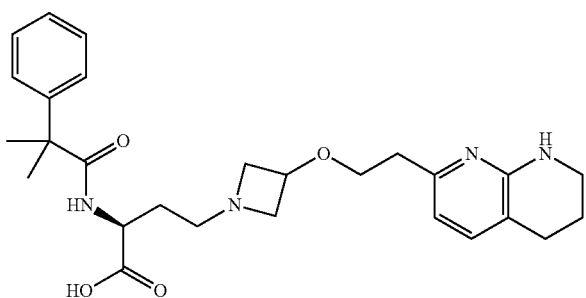 [SMILES: CC(C)(C(=O)N[C@@H](CCN1CC(OCCc2ccc3c(n2)NCCC3)C1)C(=O)O)c1ccccc1] |
| 121 | 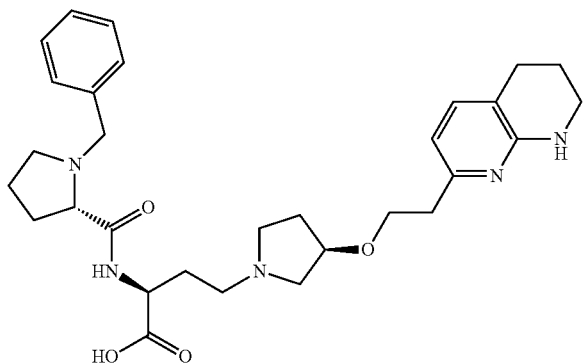 [SMILES: O=C(O)[C@H](CCN1CC[C@@H](OCCc2ccc3c(n2)NCCC3)C1)NC(=O)[C@@H]1CCCN1Cc1ccccc1] |
| 122 | 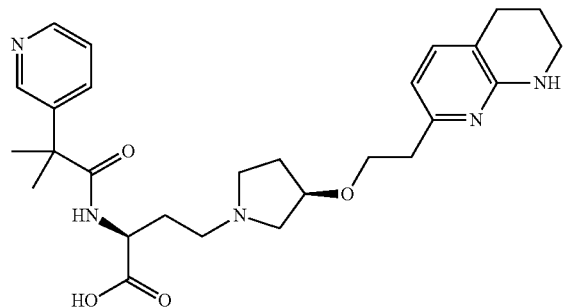 [SMILES: CC(C)(C(=O)N[C@@H](CCN1CC[C@@H](OCCc2ccc3c(n2)NCCC3)C1)C(=O)O)c1cccnc1] |

| Compound No. | Structure |
|---|---|
| 123 | 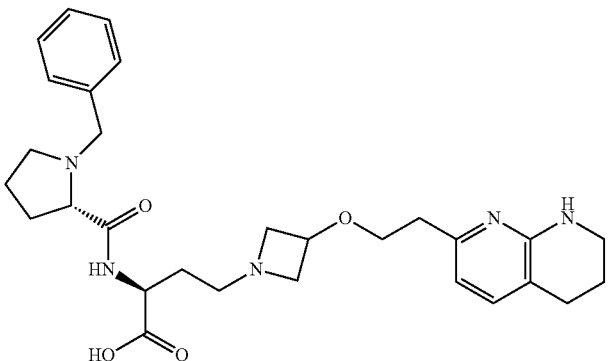 [SMILES: O=C(O)[C@H](CCN1CC(OCCc2ccc3c(n2)NCCC3)C1)NC(=O)[C@@H]1CCCN1Cc1ccccc1] |
| 124 | 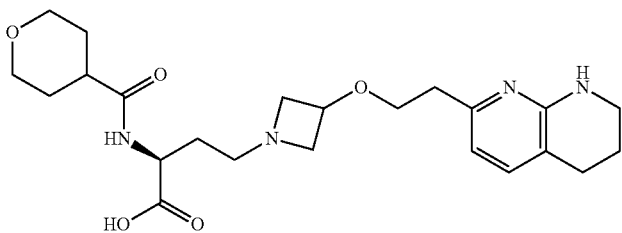 [SMILES: O=C(N[C@@H](CCN1CC(OCCc2ccc3c(n2)NCCC3)C1)C(=O)O)C1CCOCC1] |
| 125 | 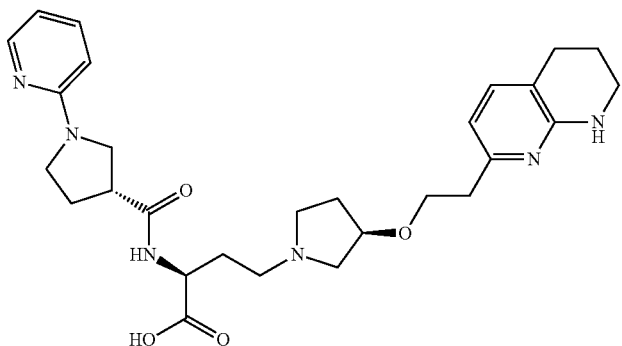 [SMILES: O=C(N[C@@H](CCN1CC[C@@H](OCCc2ccc3c(n2)NCCC3)C1)C(=O)O)[C@@H]1CCN(c2ccccn2)C1] |
| 126 | 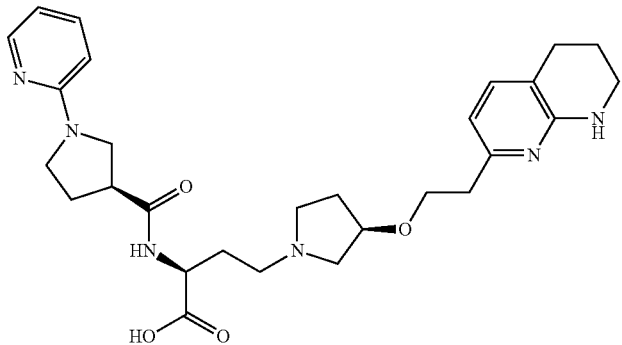 [SMILES: O=C(N[C@@H](CCN1CC[C@@H](OCCc2ccc3c(n2)NCCC3)C1)C(=O)O)[C@H]1CCN(c2ccccn2)C1] |

| Compound No. | Structure |
|---|---|
| 127 | 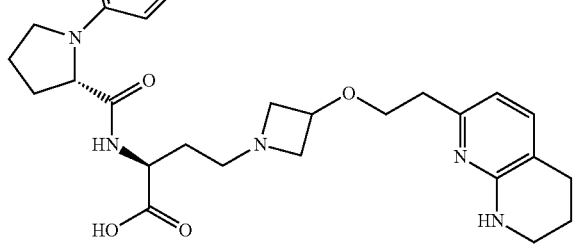 |
| 128 | 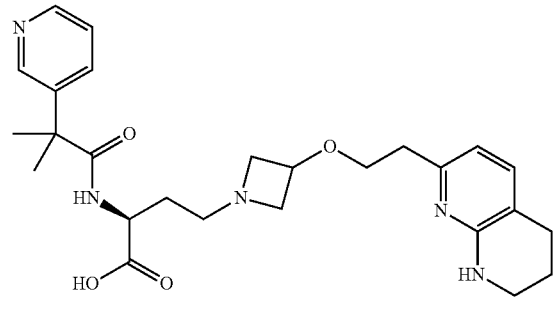 [SMILES: CC(C)(C(=O)N[C@@H](CCN1CC(OCCc2ccc3c(n2)NCCC3)C1)C(=O)O)c1cccnc1] |
| 129 | 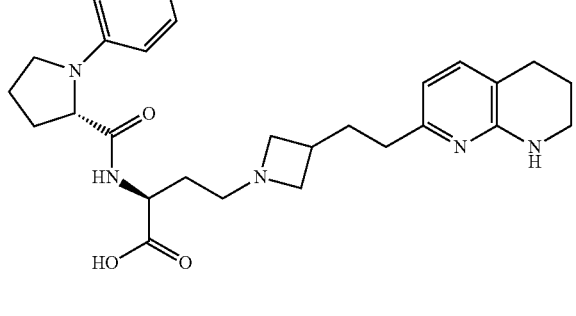 |
| 130 | 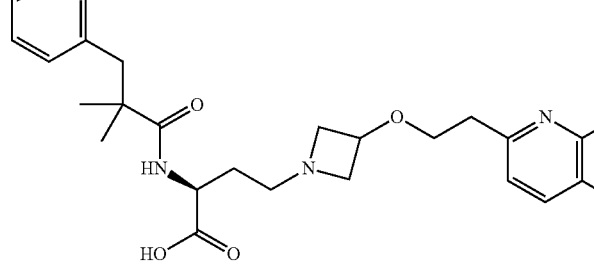 |

-continued
| Compound No. | Structure |
|---|---|
| 131 | 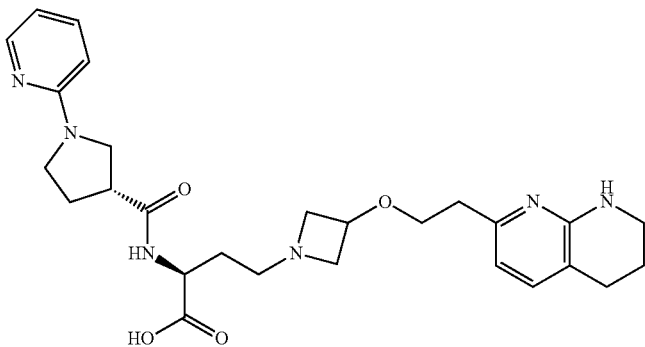 [SMILES: O=C(N[C@@H](CCN1CC(OCCc2ccc3c(n2)NCCC3)C1)C(=O)O)[C@@H]1CCN(c2ccccn2)C1] |
| 132 | 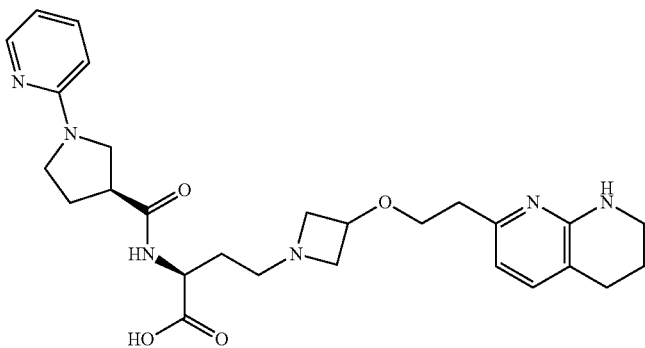 [SMILES: O=C(N[C@@H](CCN1CC(OCCc2ccc3c(n2)NCCC3)C1)C(=O)O)[C@H]1CCN(c2ccccn2)C1] |
| 133 | 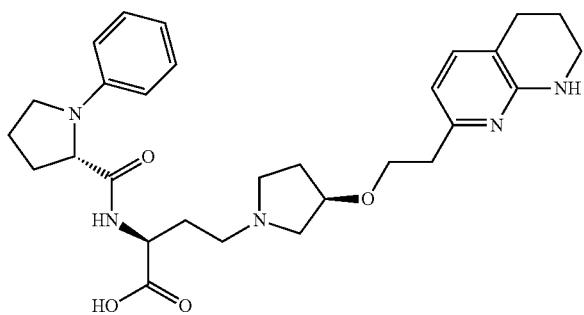 [SMILES: O=C(O)[C@H](CCN1CC[C@@H](OCCc2ccc3c(n2)NCCC3)C1)NC(=O)[C@@H]1CCCN1c1ccccc1] |
| 134 | 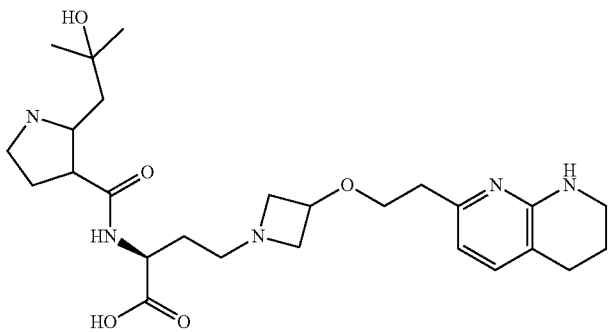 [SMILES: CC(C)(O)CC1NCCC1C(=O)N[C@@H](CCN1CC(OCCc2ccc3c(n2)NCCC3)C1)C(=O)O] |

-continued
| Compound No. | Structure |
|---|---|
| 135 | 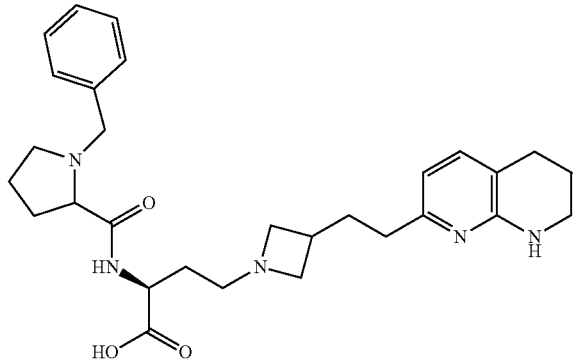 [SMILES: O=C(N[C@@H](CCN1CC(CCc2ccc3c(n2)NCCC3)C1)C(=O)O)C1CCCN1Cc1ccccc1] |
| 136 | 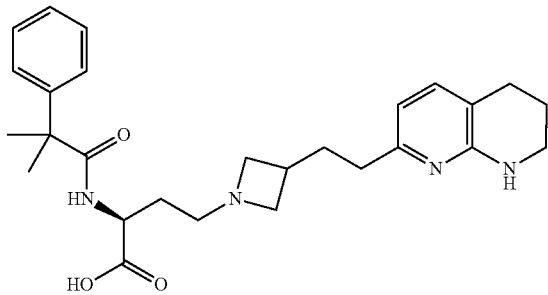 |
| 137 | 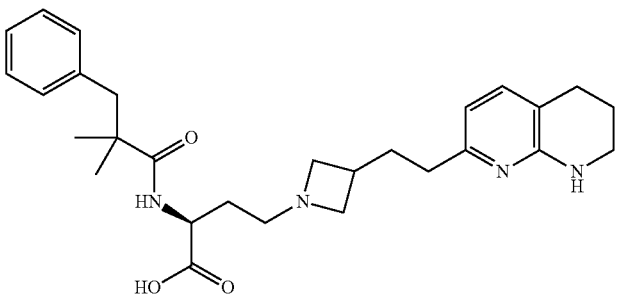 [SMILES: CC(C)(Cc1ccccc1)C(=O)N[C@@H](CCN1CC(CCc2ccc3c(n2)NCCC3)C1)C(=O)O] |
| 138 | 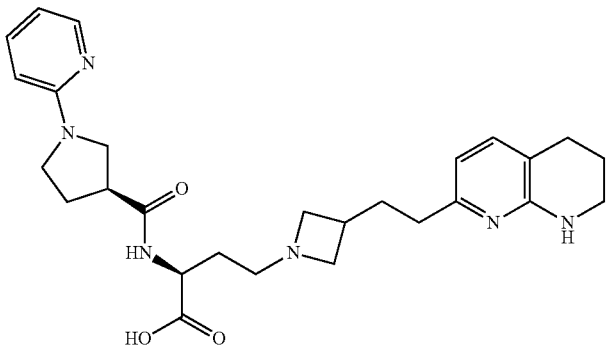 [SMILES: O=C(N[C@@H](CCN1CC(CCc2ccc3c(n2)NCCC3)C1)C(=O)O)[C@H]1CCN(c2ccccn2)C1] |
| 139 | 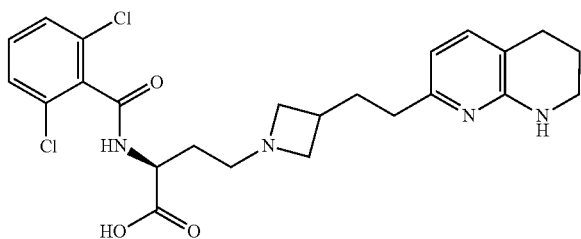 [SMILES: O=C(N[C@@H](CCN1CC(CCc2ccc3c(n2)NCCC3)C1)C(=O)O)c1c(Cl)cccc1Cl] |

-continued

| Compound No. | Structure |
|---|---|
| 140 | 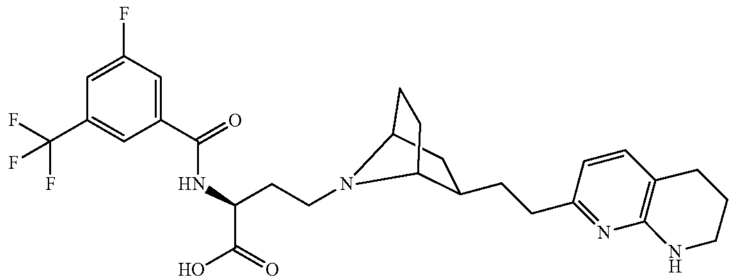 [SMILES: O=C(N[C@@H](CCN1C2CCC1C(CCc1ccc3c(n1)NCCC3)C2)C(=O)O)c1cc(F)cc(C(F)(F)F)c1] |
| 141 | 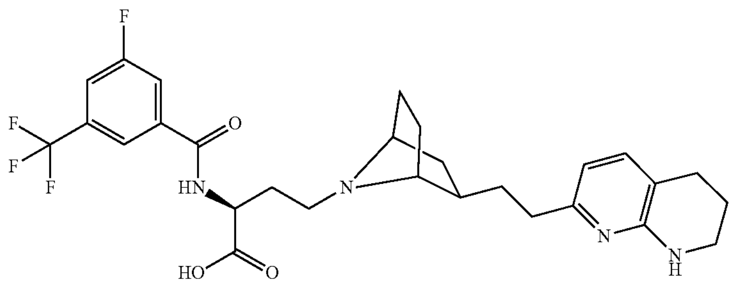 [SMILES: O=C(N[C@@H](CCN1C2CCC1C(CCc1ccc3c(n1)NCCC3)C2)C(=O)O)c1cc(F)cc(C(F)(F)F)c1] |
| 142 | 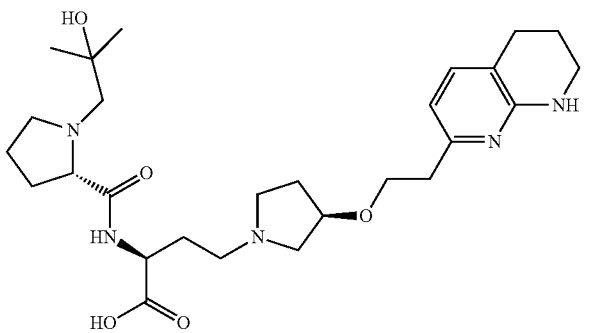 [SMILES: CC(C)(O)CN1CCC[C@H]1C(=O)N[C@@H](CCN1CC[C@@H](OCCc2ccc3c(n2)NCCC3)C1)C(=O)O] |
| 143 | 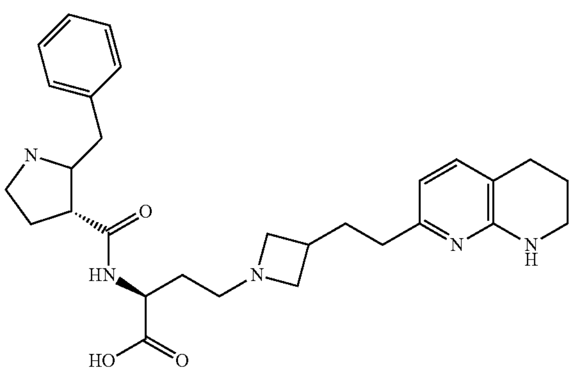 [SMILES: O=C(O)[C@H](CCN1CC(CCc2ccc3c(n2)NCCC3)C1)NC(=O)[C@@H]1CCNC1Cc1ccccc1] |
| 144 | 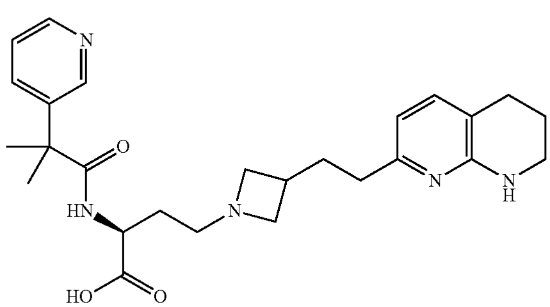 [SMILES: CC(C)(C(=O)N[C@@H](CCN1CC(CCc2ccc3c(n2)NCCC3)C1)C(=O)O)c1cccnc1] |

-continued

| Compound No. | Structure |
|---|---|
| 145 | 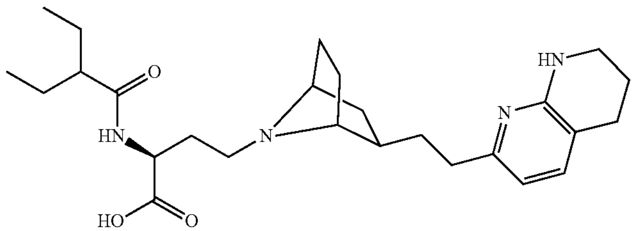 [SMILES: CCC(CC)C(=O)N[C@@H](CCN1C2CCC1C(CCc1ccc3c(n1)NCCC3)C2)C(=O)O] |
| 146 | 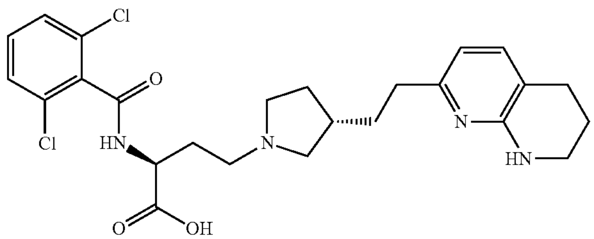 [SMILES: O=C(N[C@@H](CCN1CC[C@H](CCc2ccc3c(n2)NCCC3)C1)C(=O)O)c1c(Cl)cccc1Cl] |
| 147 | 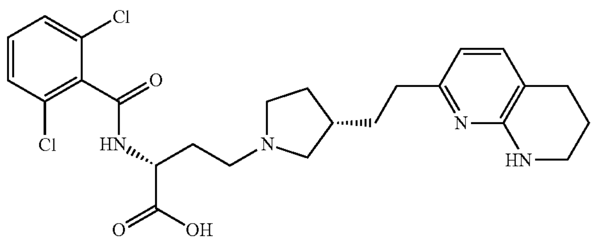 [SMILES: O=C(N[C@H](CCN1CC[C@H](CCc2ccc3c(n2)NCCC3)C1)C(=O)O)c1c(Cl)cccc1Cl] |

In some embodiments, provided is a compound selected from Compound Nos. 1-31 in Table 1, or a stereoisomer thereof (including a mixture of two or more stereoisomers thereof), or a salt thereof. In some embodiments, provided is a compound selected from Compound Nos. 1-147, or a stereoisomer thereof (including a mixture of two or more stereoisomers thereof), or a salt thereof. In some embodiments, the compound is selected from the group consisting of Compound Nos 1a, 1b, 1c, 1d, 2a, 2b, 2c, 2d, 3a, 3b, 3c, 3d, 4a, 4b, 4c, 4d, 5a, 5b, 5c, 5d, 6a, 6b, 6c, 6d, 7a, 7b, 7c, 7d, 8a, 8b, 8c, 8d, 9a, 9b, 9c, 9d, 10a, 10b, 10c, 10d, 11a, 11b, 11c, 11d, 12a, 12b, 13a, 13b, 13c, 13d, 14a, 14b, 14c, 14d, 15a, 15b, 15c, 15d, 16a, 16b, 16c, 16d, 17a, 17b, 17c, 17d, 18a, 18b, 18c, 18d, 19a, 19b, 19c, 19d, 20a, 20b, 20c, 20d, 21a, 21b, 21c, 21d, 22a, 22b, 22c, 22d, 23a, 23b, 23c, 23d, 24a, 24b, 24c, 24d, 25a, 25b, 25c, 25d, 26a, 26b, 26c, 26d, 27a, 27b, 27c, 27d, 28a, 28b, 28c, 28d, 29a, 29b, 29c, 29d, 30a, 30b, 30c, 30d, 31a, 3 b, 31c and 31d, or a salt thereof.

In some embodiments, the compound is selected from the group consisting of one or more of Compound Nos. 1-31 in Table 1, or a stereoisomer thereof (including a mixture of two or more stereoisomers thereof), or a salt thereof. In some embodiments, the compound is selected from the group consisting of one or more of Compound Nos 1a, 1b, 1c, 1d, 2a, 2b, 2c, 2d, 3a, 3b, 3c, 3d, 4a, 4b, 4c, 4d, 5a, 5b, 5c, 5d, 6a, 6b, 6c, 6d, 7a, 7b, 7c, 7d, 8a, 8b, 8c, 8d, 9a, 9b, 9c, 9d, 10a, 10b, 10c, 10d, 11a, 11b, 11c, 11d, 12a, 12b, 13a, 13b, 13c, 13d, 14a, 14b, 14c, 14d, 15a, 15b, 15c, 15d, 16a, 16b, 16c, 16d, 17a, 17b, 17c, 17d, 18a, 18b, 18c, 18d, 19a, 19b, 19c, 19d, 20a, 20b, 20c, 20d, 21a, 21b, 21c, 21d, 22a, 22b, 22c, 22d, 23a, 23b, 23c, 23d, 24a, 24b, 24c, 24d, 25a, 25b, 25c, 25d, 26a, 26b, 26c, 26d, 27a, 27b, 27c, 27d, 28a, 28b, 28c, 28d, 29a, 29b, 29c, 29d, 30a, 30b, 30c, 30d, 31a, 31b, 31c and 31d, or a salt thereof.

In some embodiments, provided is a compound selected from Compound Nos. 32-147 in Table 1-A, or a stereoisomer thereof (including a mixture of two or more stereoisomers thereof), or a salt thereof.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

Compounds described herein are αvβ6 integrin inhibitors. In some instances, it is desirable for the compound to inhibit other integrins in addition to αvβ6 integrin. In some embodiments, the compound inhibits αvβ6 integrin and one or more of αvβ1, αvβ3, αvβ5, α2β1, α3β1, α6β1 integrin, α7β1 and α11β1. In some embodiments, the compound inhibits αvβ6 integrin and αvβ1 integrin. In some embodiments, the compound inhibits αvβ6 integrin, αvβ3 integrin and αvβ5 integrin. In some embodiments, the compound inhibits αvβ6 integrin and α2β1 integrin. In some embodiments, the compound inhibits αvβ6 integrin, α2β1 integrin and α3β1 integrin. In some embodiments, the compound inhibits αvβ6 integrin and α6β1 integrin. In some embodiments, the compound inhibits αvβ6 integrin and α7β1 integrin. In some embodiments, the compound inhibits αvβ6 integrin and α11β1 integrin.

In some instances, it is desirable to avoid inhibition of other integrins. In some embodiments, the compound is a selective αvβ6 integrin inhibitor. In some embodiments, the compound does not inhibit substantially α4β1, αvβ8 and/or α2β3 integrin. In some embodiments, the compound inhibits αvβ6 integrin but does not inhibit substantially α4β1 integrin. In some embodiments, the compound inhibits αvβ6 integrin but does not inhibit substantially αvβ8 integrin. In some embodiments, the compound inhibits αvβ6 integrin but does not inhibit substantially α2β3 integrin. In some embodiments, the compound inhibits αvβ6 integrin but does not inhibit substantially the αvβ8 integrin and the α4β1 integrin.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound.

Articles of manufacture comprising a compound of the invention, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms.

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds of the formula (I) can be prepared according to Scheme 1, wherein $R^1$, $R^5$, $R^7$, $R^8$, X, m, n, p and q are as defined for formula (I), or any applicable variations detailed herein; $P^0$ and $P^1$ are independently an amine protecting group, (e.g., t-butoxycarbonyl (Boc)); $P^2$ is a carboxylic acid protecting group (e.g., ethyl); and Lv is a leaving group (e.g., OH, O-acyl, OAt, OBt, Cl, 1-imidazolyl, and the like).

Scheme 1

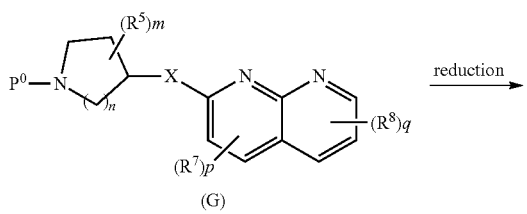

(G)

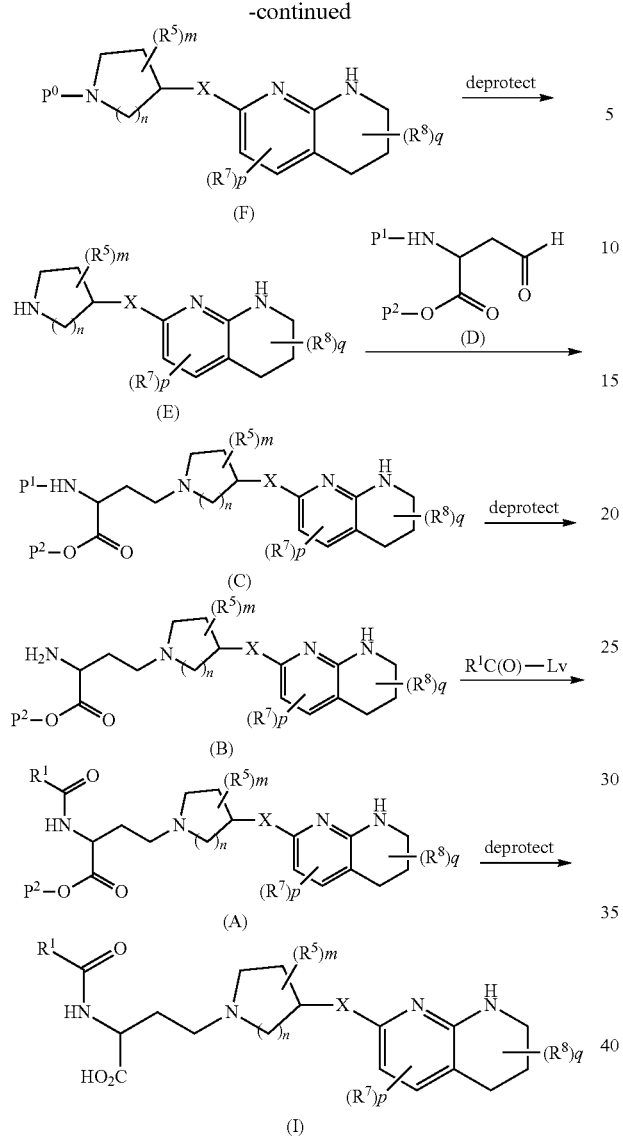

(F)

(E)

(C)

(B)

(A)

(I)

Reduction (e.g., catalytic hydrogenation) of 1,8-naphthyridine compound (G), for example, using $H_2$ over palladium hydroxide in methanol, gives tetrahydro-1,8-naphthyridine compound (F), which is deprotected to give compound (E). Reductive alkylation of compound (E) with aldehyde (D) (a protected 2-amino-4-oxobutanoic acid) produces intermediate compound (C), which is deprotected to give amine compound (B). Coupling of amine compound (B) with activated carbonyl compound $R^1C(O)$-Lv gives intermediate compound (A). Deprotection of the carboxylic acid (e.g., hydrolysis) provides a compound of formula (I).

It is understood that the schemes above may be modified to arrive at various compounds of the invention by selection of appropriate reagents and starting materials. It is also understood that where protection of certain active or incompatible groups (e.g., an amine or a carboxylic acid) is required, the formulae in Scheme 1 intend and include compounds where such active or incompatible groups are in appropriate protected forms. For a general description of protecting groups and their use, see P. G. M. Wuts and T. W. Greene, Greene's Protective Groups in Organic Synthesis 4$^{th}$ edition, Wiley-Interscience, New York, 2006.

An exemplary embodiment of the preparative method in Scheme 1 is shown in Scheme 1a. In some embodiments, $R^1$ is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of $R^1$ are independently optionally substituted by $R^{10}$.

Scheme 1a

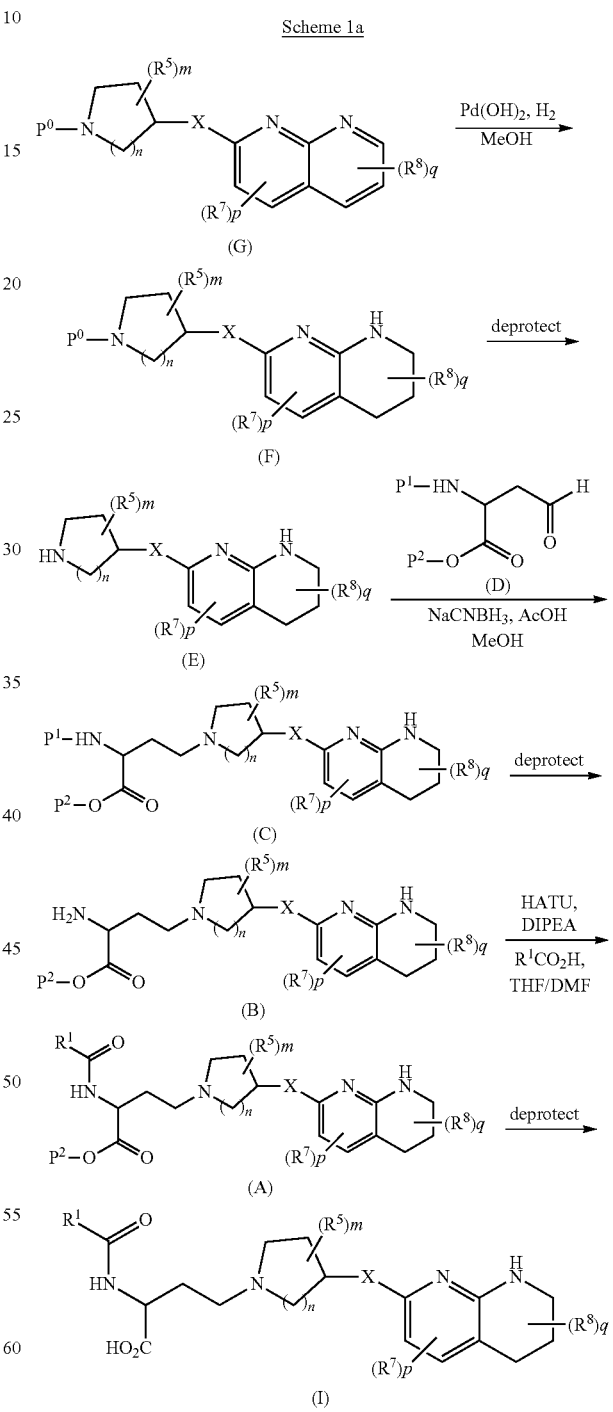

Provided is a method for preparing a compound of formula (I), or a salt thereof, comprising performing one or more steps of Scheme 1 or Scheme 1a.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1%/0 of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, $21^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof. In one aspect, the individual is a human. The individual, such as human, may be in need of treatment, such as a human who has or is suspected of having a fibrotic disease.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is a pulmonary fibrosis, e.g., idiopathic pulmonary fibrosis (IPF).

In some embodiments, the fibrotic disease is a primary sclerosing cholangitis, or biliary fibrosis.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic steatosis induced liver fibrosis, and cirrhosis.

In some embodiments, the fibrotic disease is biliary tract fibrosis.

In some embodiments, the fibrotic disease is kidney fibrosis, e.g., diabetic nephrosclerosis, hypertensive nephrosclerosis, focal segmental glomerulosclerosis ("FSGS"), and acute kidney injury from contrast induced nephropathy.

In some embodiments, the fibrotic disease is systemic and local sclerosis or scleroderma, keloids and hypertrophic scars, or post surgical adhesions.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In one aspect, provided is a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof, for use in the treatment of a fibrotic disease.

Also provided is use of a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof, in the manufacture of a medicament for the treatment of a fibrotic disease.

In another aspect, provided is a method of inhibiting αvβ6 integrin in an individual comprising administering a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof.

Also provided is a method of inhibiting TGFβ activation in a cell comprising administering to the cell a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof.

Also provided is a method of inhibiting αvβ6 integrin in an individual in need thereof, comprising administering to the individual a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof. In one such method, the compound is a selective αvβ6 integrin inhibitor. In another such method, the compound does not inhibit substantially α4β1, αvβ8 and/or α2β3 integrin. In yet another such method, the compound inhibits αvβ6 integrin but does not inhibit substantially α4β1 integrin. In still another such method, the compound inhibits αvβ6 integrin but does not inhibit substantially αvβ8 integrin. In a further such method, the compound inhibits αvβ6 integrin but does not inhibit substantially α2β3 integrin. In one embodiment is provided a method of inhibiting αvβ6 integrin and one or more of αvβ1, αvβ3, αvβ5, α2β1, α3β1, α6β1 integrin, α7β1 and α11β1 in an individual in need thereof. In another embodiment is provided a method of inhibiting αvβ6 integrin and αvβ1 integrin. In another embodiment is provided a method of inhibiting αvβ6 integrin, αvβ3 integrin and αvβ5 integrin. In another embodiment is provided a method of inhibiting αvβ6 integrin and α2β1 integrin. In another embodiment is provided a method of inhibiting αvβ6 integrin, α2β1 integrin and α3β1 integrin. In another embodiment is provided a method of inhibiting αvβ6 integrin and α6β1 integrin. In another embodiment is provided a method of inhibiting αvβ6 integrin and α7β1 integrin. In another embodiment is provided a method of inhibiting αvβ6 integrin and α11β1 integrin. In all such embodiments, in one aspect the method of inhibition is for an individual in need thereof, such as an individual who has or is suspected of having a fibrotic disease, and wherein the method comprises administering to the individual a compound of formula (I), or any variation thereof, e.g., a compound of formula (Ia), (Ib), (II), (IIa), (IIb), (III), (IIIa), (IIIb), (IV), (IVa), (IVb), (IVc), (IVd), (V), (Va) or (Vb), a compound selected from Compound Nos. 1-31 in Table 1, or a pharmaceutically acceptable salt thereof.

In any of the described methods, in one aspect the individual is a human, such as a human in need of the method. The individual may be a human who has been diagnosed with or is suspected of having a fibrotic disease.

The individual may be a human who does not have detectable disease but who has one or more risk factors for developing a fibrotic disease.

Kits

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention.

Example 1

Synthesis of Tert-Butyl (R)-3-(2-(5,6,7,8-tetrahydro-1,8-naphthyridin-2-yl)ethyl)pyrrolidine-1-carboxylate

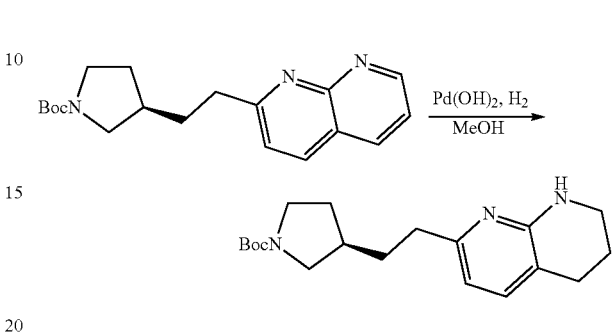

A flask equipped with a magnetic stir bar was charged with tert-butyl (R)-3-(2-(1,8-naphthyridin-2-yl)ethyl)pyrrolidine-1-carboxylate (3.10 g, 9.47 mmol, 1.0 equiv) and 20 wt % Pd(OH)$_2$/C (310 mg) and then diluted in MeOH (31 mL). The flask was then evacuated and then backfilled with H$_2$ for three cycles and then stirred under an H$_2$ atmosphere for 18 h, at which time, LC/MS had indicated complete conversion to the desired product. The mixture was filtered through a pad of Celite and concentrated in vacuo to give a crude residue that was purified by normal phase silica gel chromatography (MeOH/EtOAc 0-20% gradient) to give tert-butyl (R)-3-(2-(5,6,7,8-tetrahydro-1,8-naphthyridin-2-yl)ethyl)pyrrolidine-1-carboxylate. MS (ESI+, m/e) 332 (M+1).

Example 2

Synthesis of (R)-7-(2-(pyrrolidin-3-yl)ethyl)-1,2,3,4-tetrahydro-1,8-naphthyridine Dihydrochloride

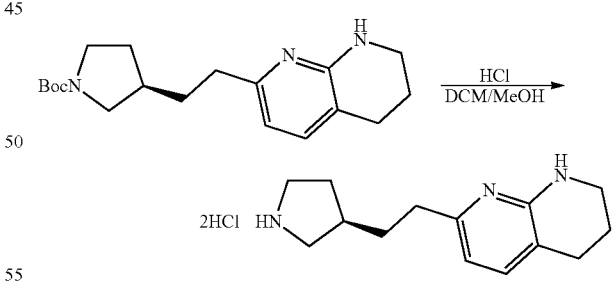

A flask containing tert-butyl (R)-3-(2-(5,6,7,8-tetrahydro-1,8-naphthyridin-2-yl)ethyl)pyrrolidine-1-carboxylate (909 mg, 2.74 mmol, 1.0 equiv) was equipped with a stir bar then diluted in 10:1 DCM/MeOH (9 mL). To this was then slowly added 4M HCl in dioxane (2.8 mL, 11.2 mmol, 4.1 equiv) and the mixture was allowed to stir at room temperature for 4 hr and then concentrated in vacuo to give (R)-7-(2-(pyrrolidin-3-yl)ethyl)-1,2,3,4-tetrahydro-1,8-naphthyridine dihydrochloride that was used without further purification. MS (ESI+, m/e) 232 (M+1).

Example 3

Synthesis of Ethyl (S)-2-((tert-butoxycarbonyl)amino)-4-((R)-3-(2-(5,6,7,8-tetrahydro-1,8-naphthyridin-2-yl)ethyl)pyrrolidin-1-yl)butanoate

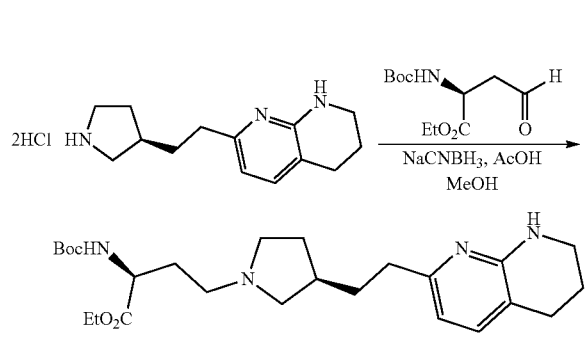

To a solution of (R)-7-(2-(pyrrolidin-3-yl)ethyl)-1,2,3,4-tetrahydro-1,8-naphthyridine dihydrochloride (446 mg, 1.47 mmol, 1.0 equiv) in MeOH (5 mL) was added AcOH (84 µL, 1.47 mmol, 1.0 equiv) then NaCNBH$_3$ (184 mg, 2.93 mmol, 2.0 equiv) at room temperature. To this was then added ethyl (S)-2-((tert-butoxycarbonyl)amino)-4-oxobutanoate (607 mg, 2.48 mmol, 1.7 equiv) and the resulting mixture was stirred for 1.5 hr at room temperature and then concentrated in vacuo. The crude residue was purified by normal phase silica gel chromatography (2.0 M NH$_3$ in MeOH/EtOAc 0-30%) to give ethyl (S)-2-((tert-butoxycarbonyl)amino)-4-((R)-3-(2-(5,6,7,8-tetrahydro-1,8-naphthyridin-2-yl)ethyl)pyrrolidin-1-yl)butanoate. MS (ESI+, m/e) 461 (M+1).

Example 4

Synthesis of Ethyl (S)-2-amino-4-((R)-3-(2-(5,6,7,8-tetrahydro-1,8-naphthyridin-2-yl)ethyl)pyrrolidin-1-yl)butanoate Trihydrochloride

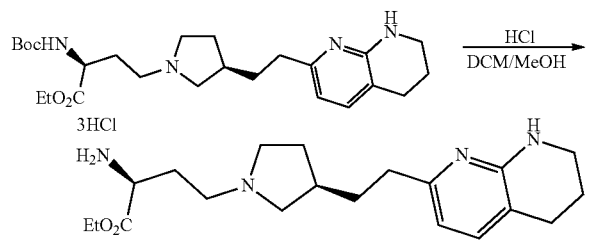

A flask containing ethyl (S)-2-((tert-butoxycarbonyl)amino)-4-((R)-3-(2-(5,6,7,8-tetrahydro-1,8-naphthyridin-2-yl)ethyl)pyrrolidin-1-yl)butanoate (605 mg, 1.31 mmol, 1.0 equiv) was equipped with a stir bar then diluted in 10:1 DCM/MeOH (6 mL). To this was then slowly added 4M HCl in dioxane (1.3 mL, 5.2 mmol, 4.0 equiv) and the mixture was allowed to stir at room temperature for 4 hr and then concentrated in vacuo to give ethyl (S)-2-amino-4-((R)-3-(2-(5,6,7,8-tetrahydro-1,8-naphthyridin-2-yl)ethyl)pyrrolidin-1-yl)butanoate trihydrochloride that was used without further purification. MS (ESI+, m/e) 361 (M+1).

Example 5

General Procedure for Amide Coupling

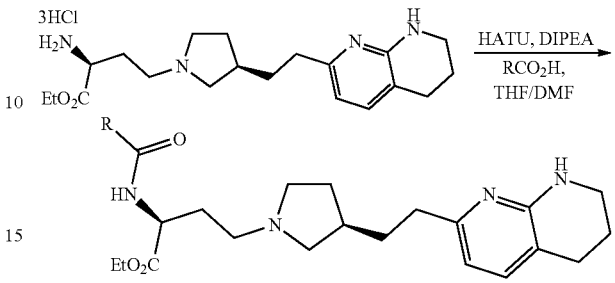

A flask containing ethyl (S)-2-amino-4-((R)-3-(2-(5,6,7,8-tetrahydro-1,8-naphthyridin-2-yl)ethyl)pyrrolidin-1-yl)butanoate trihydrochloride (50 mg, 0.1 mmol, 1.0 equiv) was diluted with 10:1 THF/DMF (2 mL) and to this was added DIPEA (93 µL, 0.5 mmol, 5.0 equiv) followed by the appropriate carboxylic acid (1.5 equiv) and then HATU (57 mg, 0.15 mmol, 1.5 equiv) at room temperature. The resulting mixture was stirred for 1 hr and then concentrated in vacuo to provide a crude residue that was purified by normal phase silica gel chromatography (2.0 M NH$_3$ in MeOH/EtOAc 0-30%) to give the desired product.

Example 6

General Procedure for Hydrolysis

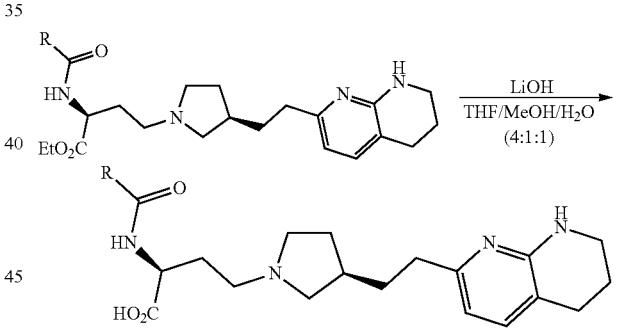

A flask containing the appropriate ester (50 mg, 1.0 equiv) was diluted with THF/MeOH/H$_2$O (1.0 mL) and to this was added LiOH (3.0 equiv) at room temperature. The resulting mixture was stirred until LC/MS indicated complete hydrolysis of the ester to the desired carboxylic acid. The mixture was neutralized by the addition of AcOH (3.0 equiv) and then filtered through a 0.2 micron filter and purified by preparative reverse phase HPLC (MeCN/H$_2$O containing 0.1% TFA, 5-95% gradient) to give the desired carboxylic acid as the trifluoroacetic acid salt.

Example 7

Synthesis of Exemplary Compounds

Certain exemplary compounds were synthesized using general procedures described herein, for example, procedures in Examples 5 and 6. The structures of the compounds and mass spectroscopy data (m/z) are listed below.

| Compound No. | Structure | m/z |
|---|---|---|
| 1a and 1c | 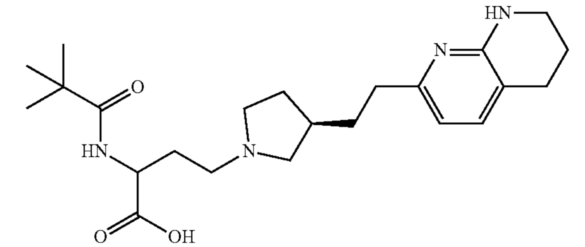 [SMILES: CC(C)(C)C(=O)NC(CCN1CC[C@@H](CCc2ccc3c(n2)NCCC3)C1)C(=O)O] | 417.2 |
| 2a | 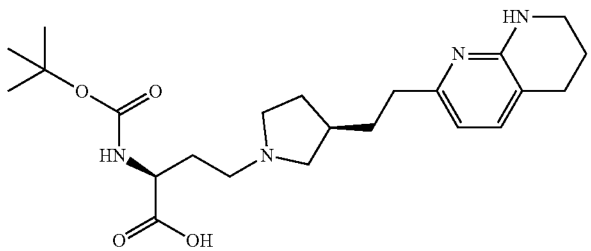 [SMILES: CC(C)(C)OC(=O)N[C@@H](CCN1CC[C@@H](CCc2ccc3c(n2)NCCC3)C1)C(=O)O] | 433.3 |
| 3a and 3c | 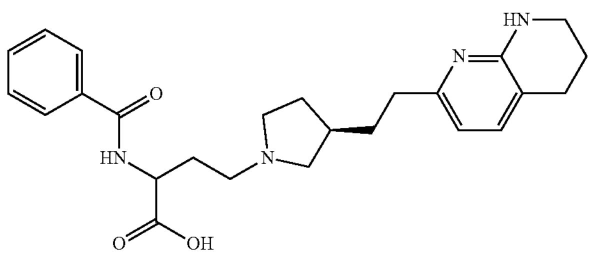 [SMILES: O=C(NC(CCN1CC[C@@H](CCc2ccc3c(n2)NCCC3)C1)C(=O)O)c1ccccc1] | 437.2 |
| 4a and 4c | 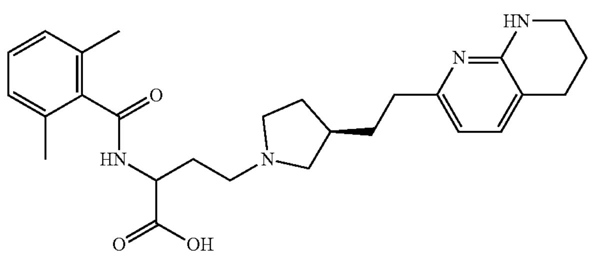 [SMILES: Cc1cccc(C)c1C(=O)NC(CCN1CC[C@@H](CCc2ccc3c(n2)NCCC3)C1)C(=O)O] | 465.2 |
| 5a | 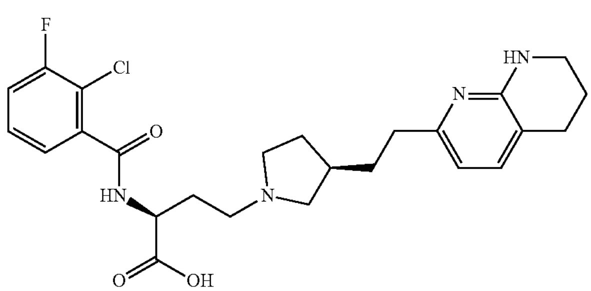 [SMILES: O=C(N[C@@H](CCN1CC[C@@H](CCc2ccc3c(n2)NCCC3)C1)C(=O)O)c1cccc(F)c1Cl] | 489.2 |
| 6a | 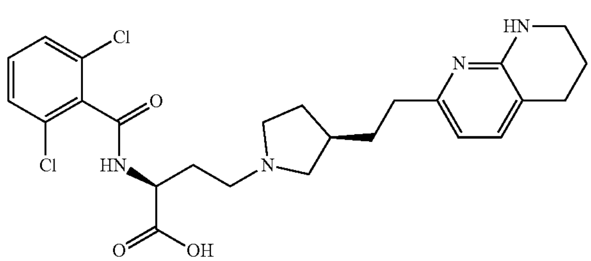 [SMILES: O=C(N[C@@H](CCN1CC[C@@H](CCc2ccc3c(n2)NCCC3)C1)C(=O)O)c1c(Cl)cccc1Cl] | 505.2 |

-continued
| Compound No. | Structure | m/z |
|---|---|---|
| 6c | 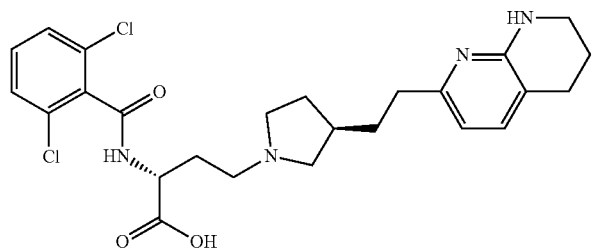 [SMILES: O=C(N[C@H](CCN1CC[C@@H](CCc2ccc3c(n2)NCCC3)C1)C(=O)O)c1c(Cl)cccc1Cl] | 505.1 |
| 7a and 7c | 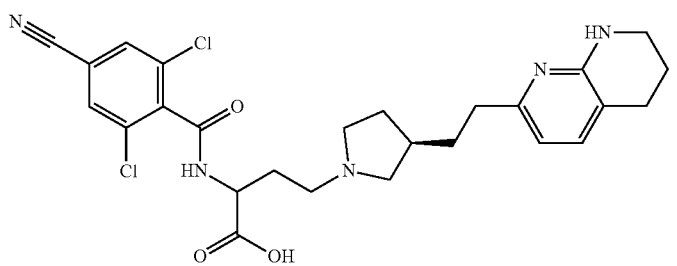 [SMILES: N#Cc1cc(Cl)c(C(=O)NC(CCN2CC[C@@H](CCc3ccc4c(n3)NCCC4)C2)C(=O)O)c(Cl)c1] | 530.1 |
| 8a | 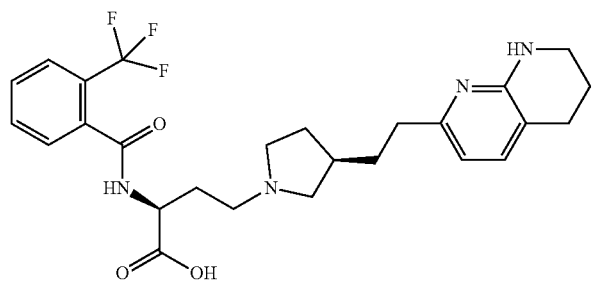 [SMILES: O=C(N[C@@H](CCN1CC[C@@H](CCc2ccc3c(n2)NCCC3)C1)C(=O)O)c1ccccc1C(F)(F)F] | 505.2 |
| 9a | 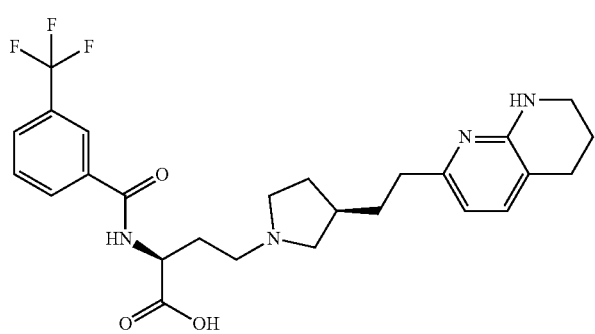 [SMILES: O=C(N[C@@H](CCN1CC[C@@H](CCc2ccc3c(n2)NCCC3)C1)C(=O)O)c1cccc(C(F)(F)F)c1] | 505.2 |
| 10a | 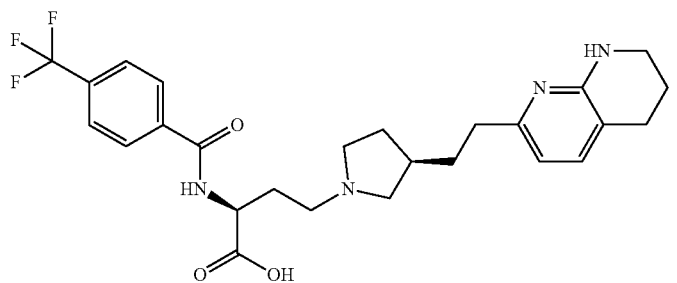 [SMILES: O=C(N[C@@H](CCN1CC[C@@H](CCc2ccc3c(n2)NCCC3)C1)C(=O)O)c1ccc(C(F)(F)F)cc1] | 505.2 |

-continued

| Compound No. | Structure | m/z |
|---|---|---|
| 11a | 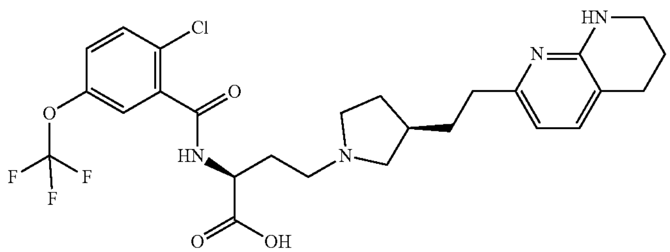 [SMILES: O=C(N[C@@H](CCN1CC[C@@H](CCc2ccc3c(n2)NCCC3)C1)C(=O)O)c1cc(OC(F)(F)F)ccc1Cl] | 555.2 |
| 12a | 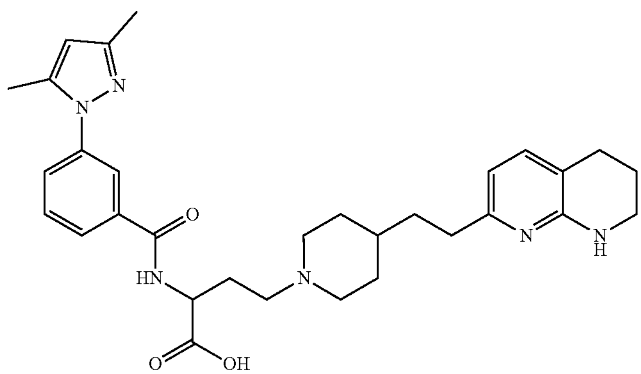 [SMILES: Cc1cc(C)n(-c2cccc(C(=O)NC(CCN3CCC(CCc4ccc5c(n4)NCCC5)CC3)C(=O)O)c2)n1] | 545.3 |
| 13a and 13c | 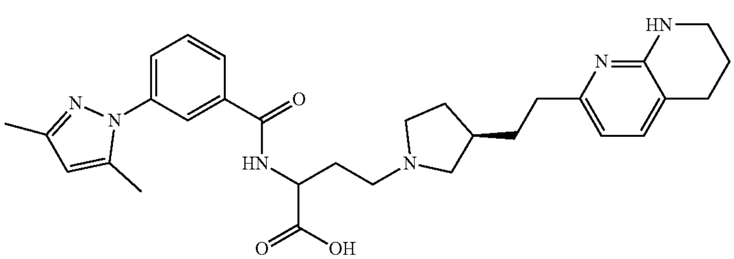 [SMILES: Cc1cc(C)n(-c2cccc(C(=O)NC(CCN3CC[C@@H](CCc4ccc5c(n4)NCCC5)C3)C(=O)O)c2)n1] | 531.3 |
| 13a | 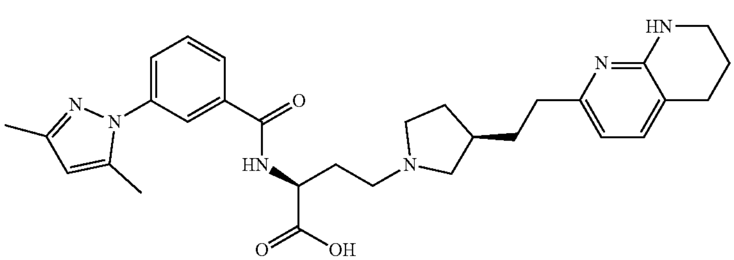 [SMILES: Cc1cc(C)n(-c2cccc(C(=O)N[C@@H](CCN3CC[C@@H](CCc4ccc5c(n4)NCCC5)C3)C(=O)O)c2)n1] | 531.3 |
| 13c | 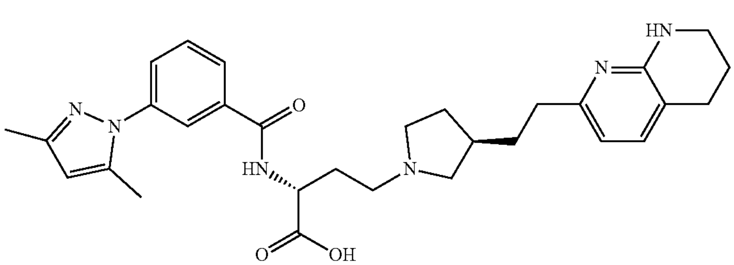 [SMILES: Cc1cc(C)n(-c2cccc(C(=O)N[C@H](CCN3CC[C@@H](CCc4ccc5c(n4)NCCC5)C3)C(=O)O)c2)n1] | 531.3 |

-continued

| Compound No. | Structure | m/z |
| --- | --- | --- |
| 14a | 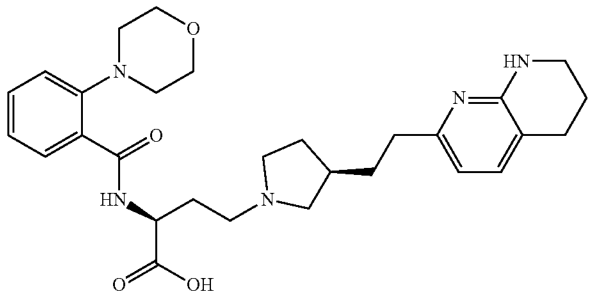 [SMILES: O=C(N[C@@H](CCN1CC[C@@H](CCc2ccc3c(n2)NCCC3)C1)C(=O)O)c1ccccc1N1CCOCC1] | 522.3 |
| 15a | 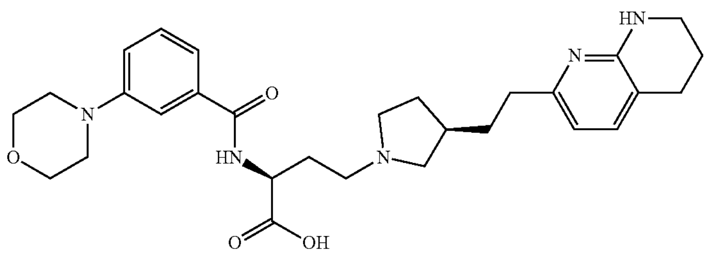 [SMILES: O=C(N[C@@H](CCN1CC[C@@H](CCc2ccc3c(n2)NCCC3)C1)C(=O)O)c1cccc(N2CCOCC2)c1] | 522.3 |
| 16a | 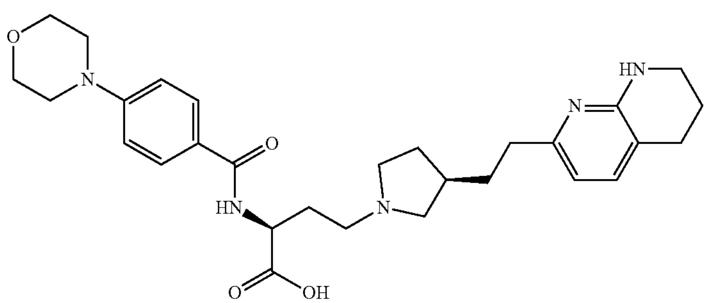 [SMILES: O=C(N[C@@H](CCN1CC[C@@H](CCc2ccc3c(n2)NCCC3)C1)C(=O)O)c1ccc(N2CCOCC2)cc1] | 522.3 |
| 17a | 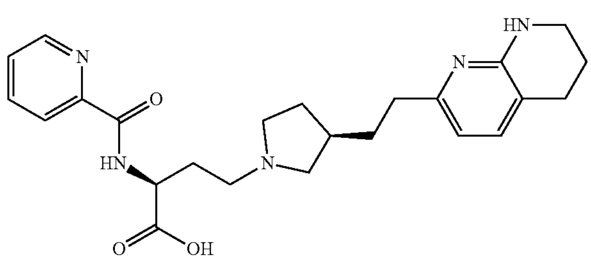 [SMILES: O=C(N[C@@H](CCN1CC[C@@H](CCc2ccc3c(n2)NCCC3)C1)C(=O)O)c1ccccn1] | 438.2 |
| 18a | 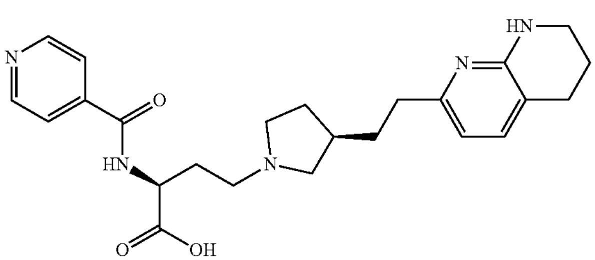 [SMILES: O=C(N[C@@H](CCN1CC[C@@H](CCc2ccc3c(n2)NCCC3)C1)C(=O)O)c1ccncc1] | 438.2 |

-continued

| Compound No. | Structure | m/z |
|---|---|---|
| 19a | 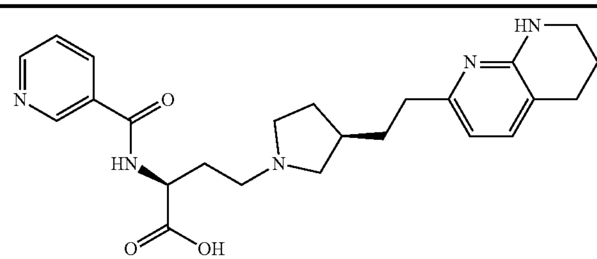 | 438.2 |
| 20a and 20c | 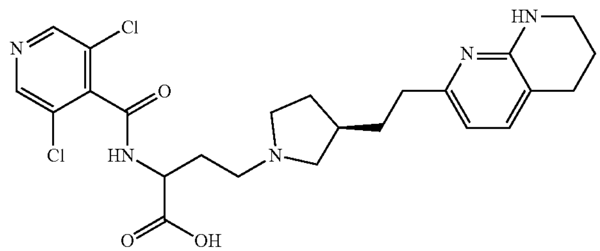 [SMILES: O=C(NC(CCN1CC[C@@H](CCc2ccc3c(n2)NCCC3)C1)C(=O)O)c1c(Cl)cncc1Cl] | 506.1 |
| 21a | 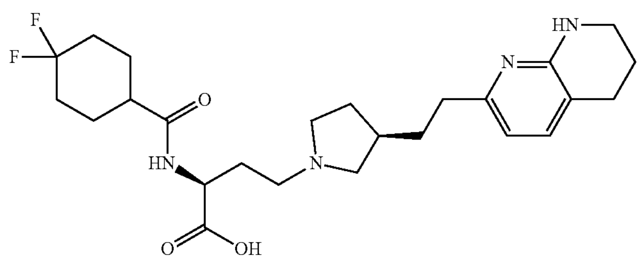 [SMILES: O=C(N[C@@H](CCN1CC[C@@H](CCc2ccc3c(n2)NCCC3)C1)C(=O)O)C1CCC(F)(F)CC1] | 479.3 |
| 21c | 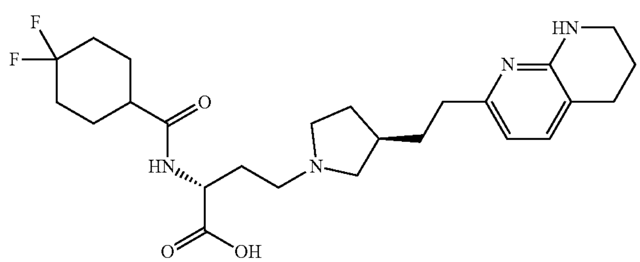 [SMILES: O=C(N[C@H](CCN1CC[C@@H](CCc2ccc3c(n2)NCCC3)C1)C(=O)O)C1CCC(F)(F)CC1] | 479.3 |
| 22a | 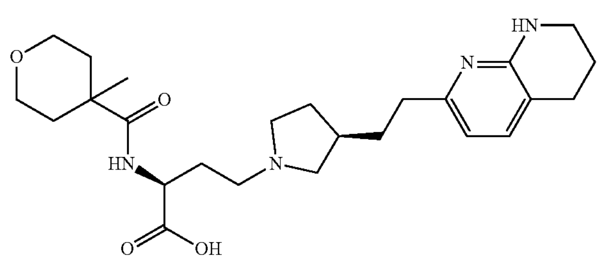 [SMILES: CC1(C(=O)N[C@@H](CCN2CC[C@@H](CCc3ccc4c(n3)NCCC4)C2)C(=O)O)CCOCC1] | 459.3 |
| 23a and 23c | 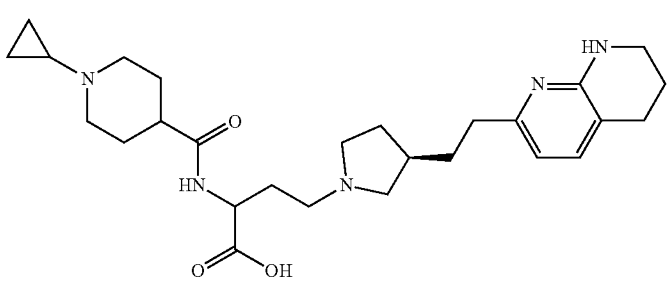 [SMILES: O=C(NC(CCN1CC[C@@H](CCc2ccc3c(n2)NCCC3)C1)C(=O)O)C1CCN(C2CC2)CC1] | 484.3 |

-continued

| Compound No. | Structure | m/z |
|---|---|---|
| 24a | 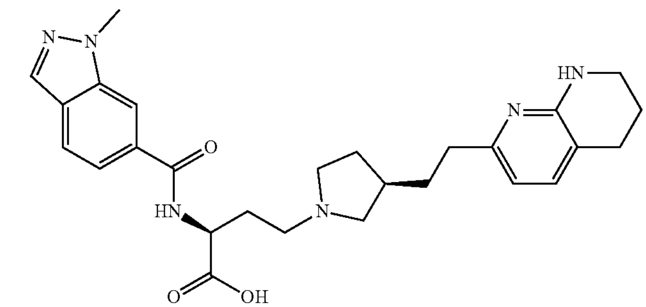 [SMILES: Cn1ncc2ccc(C(=O)N[C@@H](CCN3CC[C@@H](CCc4ccc5c(n4)NCCC5)C3)C(=O)O)cc21] | 491.3 |
| 25a | 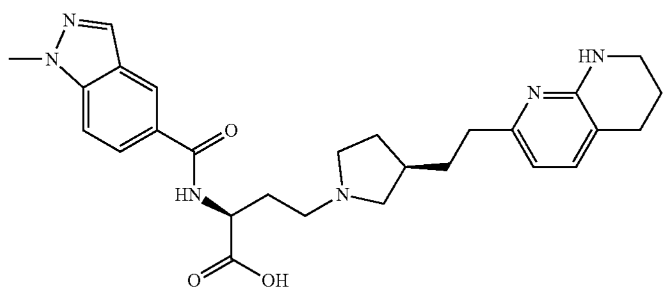 [SMILES: Cn1ncc2cc(C(=O)N[C@@H](CCN3CC[C@@H](CCc4ccc5c(n4)NCCC5)C3)C(=O)O)ccc21] | 491.3 |
| 26a | 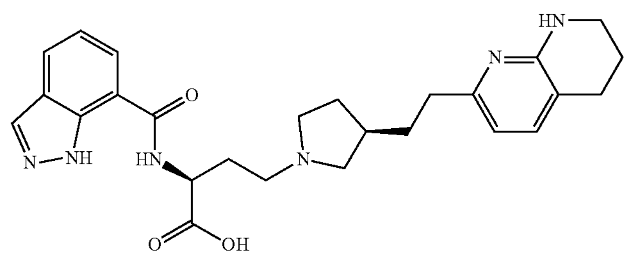 [SMILES: O=C(N[C@@H](CCN1CC[C@@H](CCc2ccc3c(n2)NCCC3)C1)C(=O)O)c1cccc2cn[nH]c12] | 477.3 |
| 27a | 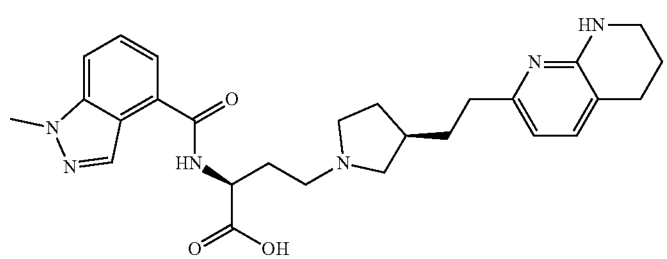 [SMILES: Cn1ncc2c(C(=O)N[C@@H](CCN3CC[C@@H](CCc4ccc5c(n4)NCCC5)C3)C(=O)O)cccc21] | 491.3 |
| 28a | 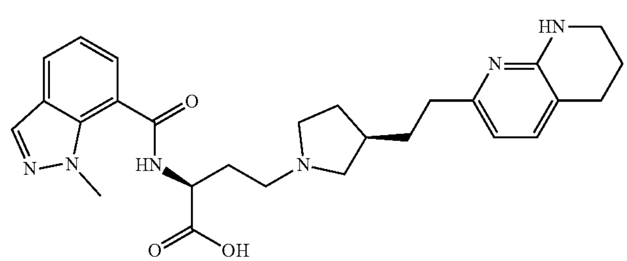 [SMILES: Cn1ncc2cccc(C(=O)N[C@@H](CCN3CC[C@@H](CCc4ccc5c(n4)NCCC5)C3)C(=O)O)c21] | 491.3 |

| Compound No. | Structure | m/z |
|---|---|---|
| 29a | (structure) | 527.2 |
| 30a | (structure) | 527.3 |
| 31a and 31c | (structure) | 478.2 |

BIOLOGICAL EXAMPLES

Example B1—Solid Phase Integrin αvβ6 Binding Assay

Microplates were coated with recombinant human integrin αvβ6 (2 ug/ml) in PBS (100 ul/well 25° C., overnight). The coating solution was removed, washed with wash buffer (0.05% Tween 20; 0.5 mM MnCl2; in 1×TBS). Plate was blocked with 200 ul/well of Block Buffer (1% BSA; 5% sucrose; 0.5 mM MnCl2; in 1×TBS) at 37° C. for 2 h. Dilutions of testing compounds and recombinant TGFβ1 LAP (0.67 ug/ml) in binding buffer (0.05% BSA; 2.5% sucrose; 0.5 mM MnCl2; in 1×TBS) were added. The plate was incubated for 2 hours at 25° C., washed, and incubated for 1 hour with Biotin-Anti-hLAP. Bound antibody was detected by peroxidase-conjugated streptavidin. The $IC_{50}$ values for testing compounds were calculated by a four-parameter logistic regression.

The $IC_{50}$ values obtained for αvβ6 integrin inhibition for exemplary compounds are shown in Table B-1. The compounds tested were compound samples prepared according to procedures described in the Synthetic Examples section, with the stereochemical purity as indicated in the Examples indicated.

TABLE B-1

| Compound No. | αvβ6 Inhibition $IC_{50}$ (nM) - range |
|---|---|
| 1c | <50 |
| 2a | <50 |
| 3a and 3c | <50 |
| 4a and 4c | <50 |
| 5a | <50 |
| 6a | <50 |
| 6c | 250-1000 |
| 7a and 7c | <50 |
| 8a | <50 |
| 9a | <50 |
| 10a | <50 |
| 11a | <50 |
| 12a | >1000 |
| 13a and 13c | <50 |
| 13a | <50 |
| 13c | <50 |
| 14a | 50-250 |
| 15a | <50 |
| 16a | >1000 |
| 17a | 50-250 |
| 18a | <50 |
| 19a | 50-250 |
| 20a and 20c | <50 |
| 21a | <50 |
| 21c | <50 |
| 22a | 50-250 |
| 23a and 23c | 50-250 |
| 24a | <50 |
| 25a | 50-250 |

TABLE B-1-continued

| Compound No. | αvβ6 Inhibition IC$_{50}$ (nM) - range |
|---|---|
| 26a | <50 |
| 27a | <50 |
| 28a | <50 |
| 29a | <50 |
| 30a | <50 |
| 31a and 31c | <50 |
| 33 | >1000 |
| 34 | >1000 |
| 35 | <50 |
| 36 | <50 |
| 37 | <50 |
| 38 | <50 |
| 39 | 50-250 |
| 40 | 250-1000 |
| 41 | 50-250 |
| 42 | 250-1000 |
| 43 | <50 |
| 44 | <50 |
| 45 | <50 |
| 46 | <50 |
| 47 | <50 |
| 48 | <50 |
| 49 | <50 |
| 50 | <50 |
| 51 | <50 |
| 52 | 50-250 |
| 53 | <50 |
| 54 | <50 |
| 55 | <50 |
| 56 | <50 |
| 57 | <50 |
| 58 | <50 |
| 59 | <50 |
| 60 | <50 |
| 61 | <50 |
| 62 | 50-250 |
| 63 | 50-250 |
| 64 | 50-250 |
| 65 | 50-250 |
| 66 | <50 |
| 67 | <50 |
| 68 | <50 |
| 69 | 50-250 |
| 70 | <50 |
| 71 | <50 |
| 72 | <50 |
| 73 | <50 |
| 74 | <50 |
| 75 | <50 |
| 76 | <50 |
| 77 | <50 |
| 78 | <50 |
| 79 | <50 |
| 80 | <50 |
| 81 | 50-250 |
| 82 | <50 |
| 83 | <50 |
| 84 | <50 |
| 85 | <50 |
| 86 | <50 |
| 87 | <50 |
| 88 | <50 |
| 89 | <50 |
| 90 | <50 |
| 91 | 50-250 |
| 92 | <50 |
| 93 | 50-250 |
| 94 | 50-250 |
| 95 | <50 |
| 96 | 50-250 |
| 97 | 50-250 |
| 98 | 250-1000 |
| 99 | <50 |
| 100 | 50-250 |
| 101 | 250-1000 |
| 102 | 250-1000 |
| 103 | <50 |
| 104 | <50 |
| 105 | 50-250 |
| 106 | 50-250 |
| 107 | 50-250 |
| 108 | 250-1000 |
| 109 | 50-250 |
| 110 | <50 |
| 111 | >1000 |
| 112 | >1000 |
| 113 | >1000 |
| 114 | 250-1000 |
| 115 | <50 |
| 116 | >1000 |
| 117 | 250-1000 |
| 118 | 250-1000 |
| 119 | 250-1000 |
| 120 | 50-250 |
| 121 | 250-1000 |
| 122 | 250-1000 |
| 123 | <50 |
| 124 | 50-250 |
| 125 | 250-1000 |
| 126 | >1000 |
| 127 | <50 |
| 128 | 250-1000 |
| 129 | 250-1000 |
| 130 | 250-1000 |
| 131 | 50-250 |
| 132 | 50-250 |
| 133 | 250-1000 |
| 134 | 250-1000 |
| 135 | >1000 |
| 136 | >1000 |
| 137 | >1000 |
| 138 | 250-1000 |
| 139 | 250-1000 |
| 140 | >1000 |
| 141 | <50 |
| 142 | >1000 |
| 143 | >1000 |
| 144 | >1000 |
| 145 | >1000 |
| 146 | <50 |
| 147 | >1000 |

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

The invention claimed is:

1. A compound of formula (I):

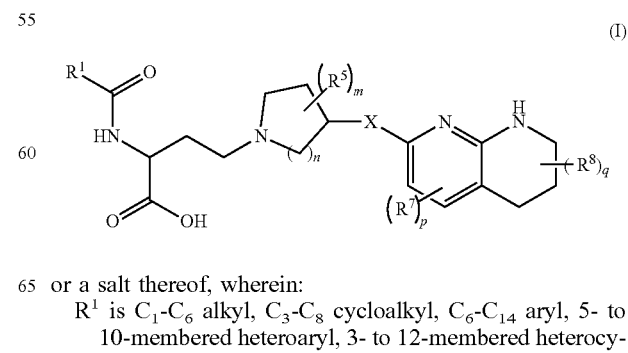

or a salt thereof, wherein:

$R^1$ is $C_1$-$C_6$ alkyl, $C_3$-$C_8$ cycloalkyl, $C_6$-$C_{14}$ aryl, 5- to 10-membered heteroaryl, 3- to 12-membered heterocyclyl, —OR² or —NR³ᵃR³ᵇ, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R¹ are independently optionally substituted by R¹⁰;

R² is $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R² are independently optionally substituted by R¹⁰;

R³ᵃ and R³ᵇ are independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R³ᵃ and R³ᵇ are independently optionally substituted by R¹⁰;

or R³ᵃ and R³ᵇ are taken together with the nitrogen to which they are attached to form a 4- to 8-membered heterocyclyl optionally substituted by R¹⁰;

n is 1 or 2;

m is 0 to 6;

each R⁵, where present, is independently $C_1$-$C_6$ alkyl, $C_3$-$C_6$ cycloalkyl, halogen, —CN, —OR⁵ᵃ, —C(O)OR⁵ᵃ, —NR⁵ᵃC(O)R⁵ᵇ; —NR⁵ᶜR⁵ᵈ, —C(O)NR⁵ᶜR⁵ᵈ, —SO₂R⁵ᵉ, or —SO₂NR⁵ᶜR⁵ᵈ, wherein the $C_1$-$C_6$ alkyl and $C_3$-$C_6$ cycloalkyl are independently optionally substituted by R¹⁰;

each R⁵ᵃ and R⁵ᵇ is independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R⁵ᵃ and R⁵ᵇ are independently optionally substituted by R¹⁰;

each R⁵ᶜ and R⁵ᵈ is independently hydrogen, $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R⁵ᶜ and R⁵ᵈ are independently optionally substituted by R¹⁰;

or R⁵ᶜ and R⁵ᵈ are taken together with the nitrogen to which they are attached to form a 4- to 8-membered heterocyclyl optionally substituted by R¹⁰;

each R⁵ᵉ is independently $C_1$-$C_6$ alkyl, $C_3$-$C_8$ cycloalkyl, $C_6$-$C_{14}$ aryl, 5- to 10-membered heteroaryl, or 3- to 12-membered heterocyclyl, wherein the $C_1$-$C_6$ alkyl, $C_3$-$C_8$ cycloalkyl, $C_6$-$C_{14}$ aryl, 5- to 10-membered heteroaryl, and 3- to 12-membered heterocyclyl of R⁵ᵉ are independently optionally substituted by R¹⁰;

X is $C_1$-$C_3$ alkylene optionally substituted by R¹⁰;

p is 0 to 2;

q is 0 to 6;

each R⁷, where present, is independently $C_1$-$C_6$ alkyl optionally substituted by halogen or —OH, $C_3$-$C_6$ cycloalkyl, halogen, —CN, —NO₂, —OR⁷ᵃ, or —NR⁷ᵇR⁷ᶜ;

each R⁷ᵃ, R⁷ᵇ and R⁷ᶜ is independently hydrogen or $C_1$-$C_3$ alkyl;

each R⁸, where present, is independently $C_1$-$C_6$ alkyl, $C_3$-$C_6$ cycloalkyl; halogen, oxo or —OR⁸ᵃ, wherein the $C_1$-$C_6$ alkyl and $C_3$-$C_6$ cycloalkyl are independently optionally substituted by R¹⁰;

R⁸ᵃ is hydrogen or $C_1$-$C_6$ alkyl;

each R⁹ is independently $C_1$-$C_6$ alkyl, $C_2$-$C_6$ alkenyl, $C_2$-$C_6$ alkynyl, halogen, —CN, —OR¹¹, —SR¹¹, —NR¹²R¹³, —NO₂, —C=NH(OR¹¹), —C(O)R¹¹, —OC(O)R¹¹, —C(O)OR¹¹, —C(O)NR¹²R¹³, —NR¹¹C(O)R¹², NR¹¹C(O)OR¹², —NR¹¹C(O)NR¹²R¹³, —S(O)R¹¹, —S(O)₂R¹¹, —NR¹¹S(O)R¹², —NR¹¹S(O)₂R¹², —S(O)NR¹²R¹³, —S(O)₂NR¹²R¹³, —P(O)(OR¹²)(OR¹³), $C_3$-$C_8$ cycloalkyl, 3- to 12-membered heterocyclyl, 5- to 10-membered heteroaryl, $C_6$-$C_{14}$ aryl, wherein each R⁹ is independently optionally substituted by halogen, oxo, —OR¹⁴—NR¹⁴R¹⁵, —C(O)R¹⁴, —CN, —S(O)R¹⁴, —S(O)₂R¹⁴, —P(O)(OR¹⁴)(OR¹⁵), $C_3$-$C_8$ cycloalkyl, 3- to 12-membered heterocyclyl, 5- to 10-membered heteroaryl, $C_6$-$C_{14}$ aryl, or $C_1$-$C_6$ alkyl optionally substituted by oxo, —OH or halogen;

each R¹⁰ is independently oxo or R⁹;

R¹¹ is independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR¹⁶, —NR¹⁶R¹⁷, P(O)(OR¹⁶)(OR¹⁷), or $C_1$-$C_6$ alkyl optionally substituted by halogen, —OH or oxo;

R¹² and R¹³ are each independently hydrogen, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 6-membered heteroaryl and 3- to 6-membered heterocyclyl are independently optionally substituted by halogen, oxo, —CN, —OR¹⁶, —NR¹⁶R¹⁷ or $C_1$-$C_6$ alkyl optionally substituted by halogen, —OH or oxo;

or R¹² and R¹³ are taken together with the atom to which they attached to form a 3- to 6-membered heterocyclyl optionally substituted by halogen, oxo, —OR¹⁶, —NR¹⁶R¹⁷ or $C_1$-$C_6$ alkyl optionally substituted by halogen, oxo or —OH;

R¹⁴ and R¹⁵ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R¹⁴ and R¹⁵ are taken together with the atom to which they attached to form a 3- to 6-membered heterocyclyl optionally substituted by halogen, oxo or $C_1$-$C_6$ alkyl optionally substituted by halogen or oxo; and R¹⁶ and R¹⁷ are each independently hydrogen, $C_1$-$C_6$ alkyl optionally substituted by halogen or oxo, $C_2$-$C_6$ alkenyl optionally substituted by halogen or oxo, or $C_2$-$C_6$ alkynyl optionally substituted by halogen or oxo;

or R¹⁶ and R¹⁷ are taken together with the atom to which they attached to form a 3-6 membered heterocyclyl optionally substituted by halogen, oxo or $C_1$-$C_6$ alkyl optionally substituted by oxo or halogen.

2. The compound of claim 1, wherein the compound is of the formula (Ia):

(Ia)

or a salt thereof.

3. The compound of claim 1, or a salt thereof, wherein n is 1.
4. The compound of claim 1, or a salt thereof, wherein n is 2.
5. The compound of claim 1, or a salt thereof, wherein X is $C_1$-$C_3$ alkylene.
6. The compound of claim 1, or a salt thereof, wherein X is $C_1$-$C_2$ alkylene optionally substituted by $R^{10}$.
7. The compound of claim 1, or a salt thereof, wherein X is ethylene.
8. The compound of claim 1, wherein the compound is of the formula (IVa):

(IVa)

or a salt thereof.

9. The compound of claim 1, or a salt thereof, wherein $R^1$ is a $C_1$-$C_6$ alkyl optionally substituted by $R^{10}$.
10. The compound of claim 9, wherein $R^1$ is t-butyl.
11. The compound of claim 1, or a salt thereof, wherein $R^1$ is —$OR^2$ or —$NR^{3a}R^{3b}$.
12. The compound of claim 11, or a salt thereof, wherein $R^1$ is —$OR^2$.
13. The compound of claim 12, or a salt thereof, wherein $R^2$ is $C_1$-$C_6$ alkyl.
14. The compound of claim 13, wherein $R^2$ is t-butyl.
15. The compound of claim 1, or a salt thereof, wherein $R^1$ is $C_3$-$C_8$ cycloalkyl optionally substituted by $R^{10}$.
16. The compound of claim 1, or a salt thereof, wherein $R^1$ is $C_6$-$C_{14}$ aryl optionally substituted by $R^{10}$.
17. The compound of claim 1, or a salt thereof, wherein $R^1$ is phenyl optionally substituted by $R^{10}$.
18. The compound of claim 1, or a salt thereof, wherein $R^1$ is 5- to 10-membered heteroaryl optionally substituted by $R^{10}$.
19. The compound of claim 18, or a salt thereof, wherein $R^1$ is pyridyl optionally substituted by $R^{10}$.
20. The compound of claim 18, or a salt thereof, wherein $R^1$ is indazolyl optionally substituted by $R^{10}$.
21. The compound of claim 1, or a salt thereof, wherein $R^1$ is 3- to 12-membered heterocyclyl optionally substituted by $R^{10}$.

22. The compound of claim 21, or a salt thereof, wherein $R^1$ is piperidinyl optionally substituted by $R^{10}$.
23. The compound of claim 21, or a salt thereof, wherein $R^1$ is tetrahydropyranyl optionally substituted by $R^{10}$.
24. The compound of claim 1, or a salt thereof, wherein $R^1$ is $C_3$-$C_8$ cycloalkyl optionally substituted by $R^{10}$.
25. The compound of claim 24, or a salt thereof, wherein $R^1$ is cyclohexyl optionally substituted by $R^{10}$.
26. The compound of claim 1, or a salt thereof, wherein $R^1$ is selected from the group consisting of:

-continued

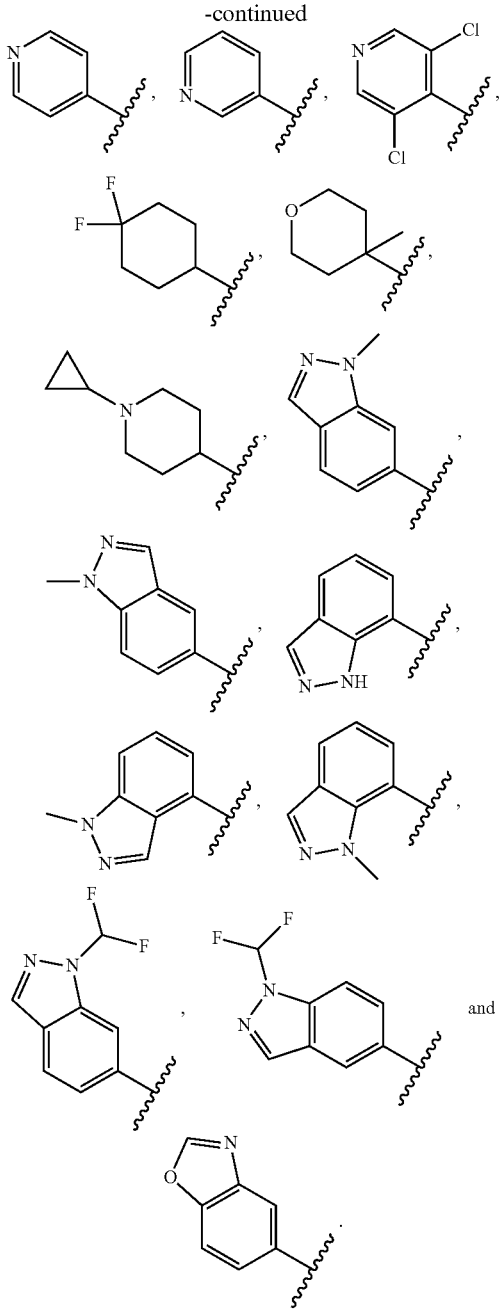

27. The compound of claim 1, wherein the compound is selected from 2-pivalamido-4-(3-(2-(5,6,7,8-tetrahydro-1,8-naphthyridin-2-yl)ethyl)pyrrolidin-1-yl)butanoic acid,
(S)-2-pivalamido-4-((R)-3-(2-(5,6,7,8-tetrahydro-1,8-naphthyridin-2-yl)ethyl)pyrrolidin-1-yl)butanoic acid,
(S)-2-pivalamido-4-((S)-3-(2-(5,6,7,8-tetrahydro-1,8-naphthyridin-2-yl)ethyl)pyrrolidin-1-yl)butanoic acid,
(R)-2-pivalamido-4-((R)-3-(2-(5,6,7,8-tetrahydro-1,8-naphthyridin-2-yl)ethyl)pyrrolidin-1-yl)butanoic acid,
(R)-2-pivalamido-4-((S)-3-(2-(5,6,7,8-tetrahydro-1,8-naphthyridin-2-yl)ethyl)pyrrolidin-1-yl)butanoic acid,
2-((tert-butoxycarbonyl)amino)-4-(3-(2-(5,6,7,8-tetrahydro-1,8-naphthyridin-2-yl)ethyl)pyrrolidin-1-yl)butanoic acid,
(S)-2-((tert-butoxycarbonyl)amino)-4-((R)-3-(2-(5,6,7,8-tetrahydro-1,8-naphthyridin-2-yl)ethyl)pyrrolidin-1-yl)butanoic acid,
(S)-2-((tert-butoxycarbonyl)amino)-4-((S)-3-(2-(5,6,7,8-tetrahydro-1,8-naphthyridin-2-yl)ethyl)pyrrolidin-1-yl)butanoic acid,
(R)-2-((tert-butoxycarbonyl)amino)-4-((R)-3-(2-(5,6,7,8-tetrahydro-1,8-naphthyridin-2-yl)ethyl)pyrrolidin-1-yl)butanoic acid,
(R)-2-((tert-butoxycarbonyl)amino)-4-((S)-3-(2-(5,6,7,8-tetrahydro-1,8-naphthyridin-2-yl)ethyl)pyrrolidin-1-yl)butanoic acid,
2-benzamido-4-(3-(2-(5,6,7,8-tetrahydro-1,8-naphthyridin-2-yl)ethyl)pyrrolidin-1-yl)butanoic acid,
(S)-2-benzamido-4-((R)-3-(2-(5,6,7,8-tetrahydro-1,8-naphthyridin-2-yl)ethyl)pyrrolidin-1-yl)butanoic acid,
(S)-2-benzamido-4-((S)-3-(2-(5,6,7,8-tetrahydro-1,8-naphthyridin-2-yl)ethyl)pyrrolidin-1-yl)butanoic acid,
(R)-2-benzamido-4-((R)-3-(2-(5,6,7,8-tetrahydro-1,8-naphthyridin-2-yl)ethyl)pyrrolidin-1-yl)butanoic acid,
(R)-2-benzamido-4-((S)-3-(2-(5,6,7,8-tetrahydro-1,8-naphthyridin-2-yl)ethyl)pyrrolidin-1-yl)butanoic acid,
2-(2,6-dimethylbenzamido)-4-(3-(2-(5,6,7,8-tetrahydro-1,8-naphthyridin-2-yl)ethyl)pyrrolidin-1-yl)butanoic acid,
(S)-2-(2,6-dimethylbenzamido)-4-((R)-3-(2-(5,6,7,8-tetrahydro-1,8-naphthyridin-2-yl)ethyl)pyrrolidin-1-yl)butanoic acid,
(S)-2-(2,6-dimethylbenzamido)-4-((S)-3-(2-(5,6,7,8-tetrahydro-1,8-naphthyridin-2-yl)ethyl)pyrrolidin-1-yl)butanoic acid,
(R)-2-(2,6-dimethylbenzamido)-4-((R)-3-(2-(5,6,7,8-tetrahydro-1,8-naphthyridin-2-yl)ethyl)pyrrolidin-1-yl)butanoic acid,
(R)-2-(2,6-dimethylbenzamido)-4-((S)-3-(2-(5,6,7,8-tetrahydro-1,8-naphthyridin-2-yl)ethyl)pyrrolidin-1-yl)butanoic acid,
2-(2-chloro-3-fluorobenzamido)-4-(3-(2-(5,6,7,8-tetrahydro-1,8-naphthyridin-2-yl)ethyl)pyrrolidin-1-yl)butanoic acid,
(S)-2-(2-chloro-3-fluorobenzamido)-4-((R)-3-(2-(5,6,7,8-tetrahydro-1,8-naphthyridin-2-yl)ethyl)pyrrolidin-1-yl)butanoic acid,
(S)-2-(2-chloro-3-fluorobenzamido)-4-((S)-3-(2-(5,6,7,8-tetrahydro-1,8-naphthyridin-2-yl)ethyl)pyrrolidin-1-yl)butanoic acid,
(R)-2-(2-chloro-3-fluorobenzamido)-4-((R)-3-(2-(5,6,7,8-tetrahydro-1,8-naphthyridin-2-yl)ethyl)pyrrolidin-1-yl)butanoic acid,
(R)-2-(2-chloro-3-fluorobenzamido)-4-((S)-3-(2-(5,6,7,8-tetrahydro-1,8-naphthyridin-2-yl)ethyl)pyrrolidin-1-yl)butanoic acid,
(S)-2-(2,6-dichlorobenzamido)-4-((R)-3-(2-(5,6,7,8-tetrahydro-1,8-naphthyridin-2-yl)ethyl)pyrrolidin-1-yl)butanoic acid,
(S)-2-(2,6-dichlorobenzamido)-4-((S)-3-(2-(5,6,7,8-tetrahydro-1,8-naphthyridin-2-yl)ethyl)pyrrolidin-1-yl)butanoic acid,
(R)-2-(2,6-dichlorobenzamido)-4-((R)-3-(2-(5,6,7,8-tetrahydro-1,8-naphthyridin-2-yl)ethyl)pyrrolidin-1-yl)butanoic acid,
(R)-2-(2,6-dichlorobenzamido)-4-((S)-3-(2-(5,6,7,8-tetrahydro-1,8-naphthyridin-2-yl)ethyl)pyrrolidin-1-yl)butanoic acid,
2-(2,6-dichloro-4-cyanobenzamido)-4-(3-(2-(5,6,7,8-tetrahydro-1,8-naphthyridin-2-yl)ethyl)pyrrolidin-1-yl)butanoic acid, (S)-2-(2,6-dichloro-4-cyanobenzamido)-4-((R)-3-(2-(5,6,7,8-tetrahydro-1,8-naphthyridin-2-yl)ethyl)pyrrolidin-1-yl)butanoic acid,
(S)-2-(2,6-dichloro-4-cyanobenzamido)-4-((S)-3-(2-(5,6,7,8-tetrahydro-1,8-naphthyridin-2-yl)ethyl)pyrrolidin-1-yl)butanoic acid,
(R)-2-(2,6-dichloro-4-cyanobenzamido)-4-((R)-3-(2-(5,6,7,8-tetrahydro-1,8-naphthyridin-2-yl)ethyl)pyrrolidin-1-yl)butanoic acid,
(R)-2-(2,6-dichloro-4-cyanobenzamido)-4-((S)-3-(2-(5,6,7,8-tetrahydro-1,8-naphthyridin-2-yl)ethyl)pyrrolidin-1-yl)butanoic acid,
4-(3-(2-(5,6,7,8-tetrahydro-1,8-naphthyridin-2-yl)ethyl)pyrrolidin-1-yl)-2-(2-(trifluoromethyl)benzamido)butanoic acid,
(S)-4-((R)-3-(2-(5,6,7,8-tetrahydro-1,8-naphthyridin-2-yl)ethyl)pyrrolidin-1-yl)-2-(2-(trifluoromethyl)benzamido)butanoic acid,
(S)-4-((S)-3-(2-(5,6,7,8-tetrahydro-1,8-naphthyridin-2-yl)ethyl)pyrrolidin-1-yl)-2-(2-(trifluoromethyl)benzamido)butanoic acid,
(R)-4-((R)-3-(2-(5,6,7,8-tetrahydro-1,8-naphthyridin-2-yl)ethyl)pyrrolidin-1-yl)-2-(2-(trifluoromethyl)benzamido)butanoic acid,
(R)-4-((S)-3-(2-(5,6,7,8-tetrahydro-1,8-naphthyridin-2-yl)ethyl)pyrrolidin-1-yl)-2-(2-(trifluoromethyl)benzamido)butanoic acid,
4-(3-(2-(5,6,7,8-tetrahydro-1,8-naphthyridin-2-yl)ethyl)pyrrolidin-1-yl)-2-(3-(trifluoromethyl)benzamido)butanoic acid,
(S)-4-((R)-3-(2-(5,6,7,8-tetrahydro-1,8-naphthyridin-2-yl)ethyl)pyrrolidin-1-yl)-2-(3-(trifluoromethyl)benzamido)butanoic acid,
(S)-4-((S)-3-(2-(5,6,7,8-tetrahydro-1,8-naphthyridin-2-yl)ethyl)pyrrolidin-1-yl)-2-(3-(trifluoromethyl)benzamido)butanoic acid,
(R)-4-((R)-3-(2-(5,6,7,8-tetrahydro-1,8-naphthyridin-2-yl)ethyl)pyrrolidin-1-yl)-2-(3-(trifluoromethyl)benzamido)butanoic acid,
(R)-4-((S)-3-(2-(5,6,7,8-tetrahydro-1,8-naphthyridin-2-yl)ethyl)pyrrolidin-1-yl)-2-(3-(trifluoromethyl)benzamido)butanoic acid,
4-(3-(2-(5,6,7,8-tetrahydro-1,8-naphthyridin-2-yl)ethyl)pyrrolidin-1-yl)-2-(4-(trifluoromethyl)benzamido)butanoic acid,
(S)-4-((R)-3-(2-(5,6,7,8-tetrahydro-1,8-naphthyridin-2-yl)ethyl)pyrrolidin-1-yl)-2-(4-(trifluoromethyl)benzamido)butanoic acid,
(S)-4-((S)-3-(2-(5,6,7,8-tetrahydro-1,8-naphthyridin-2-yl)ethyl)pyrrolidin-1-yl)-2-(4-(trifluoromethyl)benzamido)butanoic acid,
(R)-4-((R)-3-(2-(5,6,7,8-tetrahydro-1,8-naphthyridin-2-yl)ethyl)pyrrolidin-1-yl)-2-(4-(trifluoromethyl)benzamido)butanoic acid,
(R)-4-((S)-3-(2-(5,6,7,8-tetrahydro-1,8-naphthyridin-2-yl)ethyl)pyrrolidin-1-yl)-2-(4-(trifluoromethyl)benzamido)butanoic acid,
2-(2,6-dichlorobenzamido)-4-(3-(2-(5,6,7,8-tetrahydro-1,8-naphthyridin-2-yl)ethyl)pyrrolidin-1-yl)butanoic acid,
(S)-2-(2,6-dichlorobenzamido)-4-((R)-3-(2-(5,6,7,8-tetrahydro-1,8-naphthyridin-2-yl)ethyl)pyrrolidin-1-yl)butanoic acid,
(S)-2-(2,6-dichlorobenzamido)-4-((S)-3-(2-(5,6,7,8-tetrahydro-1,8-naphthyridin-2-yl)ethyl)pyrrolidin-1-yl)butanoic acid,
(R)-2-(2,6-dichlorobenzamido)-4-((R)-3-(2-(5,6,7,8-tetrahydro-1,8-naphthyridin-2-yl)ethyl)pyrrolidin-1-11dyl)butanoic acid,
(R)-2-(2,6-dichlorobenzamido)-4-((S)-3-(2-(5,6,7,8-tetrahydro-1,8-naphthyridin-2-yl)ethyl)pyrrolidin-1-yl)butanoic acid,
2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid,
(S)-2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid,
(R)-2-(3-(3,5-dimethyl-1H-pyrazol-1-yl)benzamido)-4-(4-(2-(5,6,7,8-tetrahydro-1,8-naphthyridin-2-yl)ethyl)piperidin-1-yl)butanoic acid,
2-(3-(3,5-dimethyl-1H-pyrazol-1-yl)benzamido)-4-(3-(2-(5,6,7,8-tetrahydro-1,8-naphthyridin-2-yl)ethyl)pyrrolidin-1-yl)butanoic acid,
(S)-2-(3-(3,5-dimethyl-1H-pyrazol-1-yl)benzamido)-4-((R)-3-(2-(5,6,7,8-tetrahydro-1,8-naphthyridin-2-yl)ethyl)pyrrolidin-1-yl)butanoic acid,
(S)-2-(3-(3,5-dimethyl-1H-pyrazol-1-yl)benzamido)-4-((S)-3-(2-(5,6,7,8-tetrahydro-1,8-naphthyridin-2-yl)ethyl)pyrrolidin-1-yl)butanoic acid,
(R)-2-(3-(3,5-dimethyl-1H-pyrazol-1-yl)benzamido)-4-((R)-3-(2-(5,6,7,8-tetrahydro-1,8-naphthyridin-2-yl)ethyl)pyrrolidin-1-yl)butanoic acid,
(R)-2-(3-(3,5-dimethyl-1H-pyrazol-1-yl)benzamido)-4-((S)-3-(2-(5,6,7,8-tetrahydro-1,8-naphthyridin-2-yl)ethyl)pyrrolidin-1-yl)butanoic acid,
2-(2-morpholinobenzamido)-4-(3-(2-(5,6,7,8-tetrahydro-1,8-naphthyridin-2-yl)ethyl)pyrrolidin-1-yl)butanoic acid,
(S)-2-(2-morpholinobenzamido)-4-((R)-3-(2-(5,6,7,8-tetrahydro-1,8-naphthyridin-2-yl)ethyl)pyrrolidin-1-yl)butanoic acid,
(S)-2-(2-morpholinobenzamido)-4-((S)-3-(2-(5,6,7,8-tetrahydro-1,8-naphthyridin-2-yl)ethyl)pyrrolidin-1-yl)butanoic acid,
(S)-2-(2-morpholinobenzamido)-4-((R)-3-(2-(5,6,7,8-tetrahydro-1,8-naphthyridin-2-yl)ethyl)pyrrolidin-1-yl)butanoic acid,
(R)-2-(2-morpholinobenzamido)-4-((S)-3-(2-(5,6,7,8-tetrahydro-1,8-naphthyridin-2-yl)ethyl)pyrrolidin-1-yl)butanoic acid,
2-(3-morpholinobenzamido)-4-(3-(2-(5,6,7,8-tetrahydro-1,8-naphthyridin-2-yl)ethyl)pyrrolidin-1-yl)butanoic acid,
(S)-2-(3-morpholinobenzamido)-4-((R)-3-(2-(5,6,7,8-tetrahydro-1,8-naphthyridin-2-yl)ethyl)pyrrolidin-1-yl)butanoic acid,
(S)-2-(3-morpholinobenzamido)-4-((S)-3-(2-(5,6,7,8-tetrahydro-1,8-naphthyridin-2-yl)ethyl)pyrrolidin-1-yl)butanoic acid,
(R)-2-(3-morpholinobenzamido)-4-((R)-3-(2-(5,6,7,8-tetrahydro-1,8-naphthyridin-2-yl)ethyl)pyrrolidin-1-yl)butanoic acid,
(R)-2-(3-morpholinobenzamido)-4-((S)-3-(2-(5,6,7,8-tetrahydro-1,8-naphthyridin-2-yl)ethyl)pyrrolidin-1-yl)butanoic acid,
2-(4-morpholinobenzamido)-4-(3-(2-(5,6,7,8-tetrahydro-1,8-naphthyridin-2-yl)ethyl)pyrrolidin-1-yl)butanoic acid,
(S)-2-(4-morpholinobenzamido)-4-((R)-3-(2-(5,6,7,8-tetrahydro-1,8-naphthyridin-2-yl)ethyl)pyrrolidin-1-yl)butanoic acid, (S)-2-(4-morpholinobenzamido)-4-((S)-3-(2-(5,6,7,8-tetrahydro-1,8-naphthyridin-2-yl)ethyl)pyrrolidin-1-yl)butanoic acid,
(R)-2-(4-morpholinobenzamido)-4-((R)-3-(2-(5,6,7,8-tetrahydro-1,8-naphthyridin-2-yl)ethyl)pyrrolidin-1-yl)butanoic acid,
(R)-2-(4-morpholinobenzamido)-4-((S)-3-(2-(5,6,7,8-tetrahydro-1,8-naphthyridin-2-yl)ethyl)pyrrolidin-1-yl)butanoic acid,
2-(picolinamido)-4-(3-(2-(5,6,7,8-tetrahydro-1,8-naphthyridin-2-yl)ethyl)pyrrolidin-1-yl)butanoic acid,
(S)-2-(picolinamido)-4-((R)-3-(2-(5,6,7,8-tetrahydro-1,8-naphthyridin-2-yl)ethyl)pyrrolidin-1-yl)butanoic acid,
(S)-2-(picolinamido)-4-((S)-3-(2-(5,6,7,8-tetrahydro-1,8-naphthyridin-2-yl)ethyl)pyrrolidin-1-yl)butanoic acid,
(R)-2-(picolinamido)-4-((R)-3-(2-(5,6,7,8-tetrahydro-1,8-naphthyridin-2-yl)ethyl)pyrrolidin-1-yl)butanoic acid,
(R)-2-(picolinamido)-4-((S)-3-(2-(5,6,7,8-tetrahydro-1,8-naphthyridin-2-yl)ethyl)pyrrolidin-1-yl)butanoic acid,
2-(isonicotinamido)-4-(3-(2-(5,6,7,8-tetrahydro-1,8-naphthyridin-2-yl)ethyl)pyrrolidin-1-yl)butanoic acid,
(S)-2-(isonicotinamido)-4-((R)-3-(2-(5,6,7,8-tetrahydro-1,8-naphthyridin-2-yl)ethyl)pyrrolidin-1-yl)butanoic acid,
(S)-2-(isonicotinamido)-4-((S)-3-(2-(5,6,7,8-tetrahydro-1,8-naphthyridin-2-yl)ethyl)pyrrolidin-1-yl)butanoic acid,
(R)-2-(isonicotinamido)-4-((R)-3-(2-(5,6,7,8-tetrahydro-1,8-naphthyridin-2-yl)ethyl)pyrrolidin-1-yl)butanoic acid,
(R)-2-(isonicotinamido)-4-((S)-3-(2-(5,6,7,8-tetrahydro-1,8-naphthyridin-2-yl)ethyl)pyrrolidin-1-yl)butanoic acid,
2-(nicotinamido)-4-(3-(2-(5,6,7,8-tetrahydro-1,8-naphthyridin-2-yl)ethyl)pyrrolidin-1-yl)butanoic acid,
(S)-2-(nicotinamido)-4-((R)-3-(2-(5,6,7,8-tetrahydro-1,8-naphthyridin-2-yl)ethyl)pyrrolidin-1-yl)butanoic acid,
(S)-2-(nicotinamido)-4-((S)-3-(2-(5,6,7,8-tetrahydro-1,8-naphthyridin-2-yl)ethyl)pyrrolidin-1-yl)butanoic acid,
(R)-2-(nicotinamido)-4-((R)-3-(2-(5,6,7,8-tetrahydro-1,8-naphthyridin-2-yl)ethyl)pyrrolidin-1-yl)butanoic acid,
(R)-2-(nicotinamido)-4-((S)-3-(2-(5,6,7,8-tetrahydro-1,8-naphthyridin-2-yl)ethyl)pyrrolidin-1-yl)butanoic acid,
2-(3,5-dichloroisonicotinamido)-4-(3-(2-(5,6,7,8-tetrahydro-1,8-naphthyridin-2-yl)ethyl)pyrrolidin-1-yl)butanoic acid,
(S)-2-(3,5-dichloroisonicotinamido)-4-((R)-3-(2-(5,6,7,8-tetrahydro-1,8-naphthyridin-2-yl)ethyl)pyrrolidin-1-yl)butanoic acid,
(S)-2-(3,5-dichloroisonicotinamido)-4-((S)-3-(2-(5,6,7,8-tetrahydro-1,8-naphthyridin-2-yl)ethyl)pyrrolidin-1-yl)butanoic acid,
(R)-2-(3,5-dichloroisonicotinamido)-4-((R)-3-(2-(5,6,7,8-tetrahydro-1,8-naphthyridin-2-yl)ethyl)pyrrolidin-1-yl)butanoic acid,
(R)-2-(3,5-dichloroisonicotinamido)-4-((S)-3-(2-(5,6,7,8-tetrahydro-1,8-naphthyridin-2-yl)ethyl)pyrrolidin-1-yl)butanoic acid,
2-(4,4-difluorocyclohexane-1-carboxamido)-4-(3-(2-(5,6,7,8-tetrahydro-1,8-naphthyridin-2-yl)ethyl)pyrrolidin-1-yl)butanoic acid,
(S)-2-(4,4-difluorocyclohexane-1-carboxamido)-4-((R)-3-(2-(5,6,7,8-tetrahydro-1,8-naphthyridin-2-yl)ethyl)pyrrolidin-1-yl)butanoic acid,
(S)-2-(4,4-difluorocyclohexane-1-carboxamido)-4-((S)-3-(2-(5,6,7,8-tetrahydro-1,8-naphthyridin-2-yl)ethyl)pyrrolidin-1-yl)butanoic acid,
(R)-2-(4,4-difluorocyclohexane-1-carboxamido)-4-((R)-3-(2-(5,6,7,8-tetrahydro-1,8-naphthyridin-2-yl)ethyl)pyrrolidin-1-yl)butanoic acid,
(R)-2-(4,4-difluorocyclohexane-1-carboxamido)-4-((S)-3-(2-(5,6,7,8-tetrahydro-1,8-naphthyridin-2-yl)ethyl)pyrrolidin-1-yl)butanoic acid,
2-(4-methyltetrahydro-2H-pyran-4-carboxamido)-4-(3-(2-(5,6,7,8-tetrahydro-1,8-naphthyridin-2-yl)ethyl)pyrrolidin-1-yl)butanoic acid,
(S)-2-(4-methyltetrahydro-2H-pyran-4-carboxamido)-4-((R)-3-(2-(5,6,7,8-tetrahydro-1,8-naphthyridin-2-yl)ethyl)pyrrolidin-1-yl)butanoic acid,
(S)-2-(4-methyltetrahydro-2H-pyran-4-carboxamido)-4-((S)-3-(2-(5,6,7,8-tetrahydro-1,8-naphthyridin-2-yl)ethyl)pyrrolidin-1-yl)butanoic acid,
(R)-2-(4-methyltetrahydro-2H-pyran-4-carboxamido)-4-((R)-3-(2-(5,6,7,8-tetrahydro-1,8-naphthyridin-2-yl)ethyl)pyrrolidin-1-yl)butanoic acid,
(R)-2-(4-methyltetrahydro-2H-pyran-4-carboxamido)-4-((S)-3-(2-(5,6,7,8-tetrahydro-1,8-naphthyridin-2-yl)ethyl)pyrrolidin-1-yl)butanoic acid,
2-(1-cyclopropylpiperidine-4-carboxamido)-4-(3-(2-(5,6,7,8-tetrahydro-1,8-naphthyridin-2-yl)ethyl)pyrrolidin-1-yl)butanoic acid,
(S)-2-(1-cyclopropylpiperidine-4-carboxamido)-4-((R)-3-(2-(5,6,7,8-tetrahydro-1,8-naphthyridin-2-yl)ethyl)pyrrolidin-1-yl)butanoic acid,
(S)-2-(1-cyclopropylpiperidine-4-carboxamido)-4-((S)-3-(2-(5,6,7,8-tetrahydro-1,8-naphthyridin-2-yl)ethyl)pyrrolidin-1-yl)butanoic acid,
(R)-2-(1-cyclopropylpiperidine-4-carboxamido)-4-((R)-3-(2-(5,6,7,8-tetrahydro-1,8-naphthyridin-2-yl)ethyl)pyrrolidin-1-yl)butanoic acid,
(R)-2-(1-cyclopropylpiperidine-4-carboxamido)-4-((S)-3-(2-(5,6,7,8-tetrahydro-1,8-naphthyridin-2-yl)ethyl)pyrrolidin-1-yl)butanoic acid,
2-(1-methyl-1H-indazole-6-carboxamido)-4-(3-(2-(5,6,7,8-tetrahydro-1,8-naphthyridin-2-yl)ethyl)pyrrolidin-1-yl)butanoic acid,
(S)-2-(1-methyl-1H-indazole-6-carboxamido)-4-((R)-3-(2-(5,6,7,8-tetrahydro-1,8-naphthyridin-2-yl)ethyl)pyrrolidin-1-yl)butanoic acid,
(S)-2-(1-methyl-1H-indazole-6-carboxamido)-4-((s)-3-(2-(5,6,7,8-tetrahydro-1,8-naphthyridin-2-yl)ethyl)pyrrolidin-1-yl)butanoic acid,
(r)-2-(1-methyl-1H-indazole-6-carboxamido)-4-((R)-3-(2-(5,6,7,8-tetrahydro-1,8-naphthyridin-2-yl)ethyl)pyrrolidin-1-yl)butanoic acid,
(r)-2-(1-methyl-1H-indazole-6-carboxamido)-4-((s)-3-(2-(5,6,7,8-tetrahydro-1,8-naphthyridin-2-yl)ethyl)pyrrolidin-1-yl)butanoic acid,
2-(1-methyl-1H-indazole-5-carboxamido)-4-(3-(2-(5,6,7,8-tetrahydro-1,8-naphthyridin-2-yl)ethyl)pyrrolidin-1-yl)butanoic acid,
(S)-2-(1-methyl-1H-indazole-5-carboxamido)-4-((R)-3-(2-(5,6,7,8-tetrahydro-1,8-naphthyridin-2-yl)ethyl)pyrrolidin-1-yl)butanoic acid,
(S)-2-(1-methyl-1H-indazole-5-carboxamido)-4-((S)-3-(2-(5,6,7,8-tetrahydro-1,8-naphthyridin-2-yl)ethyl)pyrrolidin-1-yl)butanoic acid,
(R)-2-(1-methyl-1H-indazole-5-carboxamido)-4-((R)-3-(2-(5,6,7,8-tetrahydro-1,8-naphthyridin-2-yl)ethyl)pyrrolidin-1-yl)butanoic acid, (R)-2-(1-methyl-1H-indazole-5-carboxamido)-4-((S)-3-(2-(5,6,7,8-tetrahydro-1,8-naphthyridin-2-yl)ethyl)pyrrolidin-1-yl)butanoic acid,
2-(1H-indazole-7-carboxamido)-4-(3-(2-(5,6,7,8-tetrahydro-1,8-naphthyridin-2-yl)ethyl)pyrrolidin-1-yl)butanoic acid,
(S)-2-(1H-indazole-7-carboxamido)-4-((R)-3-(2-(5,6,7,8-tetrahydro-1,8-naphthyridin-2-yl)ethyl)pyrrolidin-1-yl)butanoic acid,
(S)-2-(1H-indazole-7-carboxamido)-4-((S)-3-(2-(5,6,7,8-tetrahydro-1,8-naphthyridin-2-yl)ethyl)pyrrolidin-1-yl)butanoic acid,
(R)-2-(1H-indazole-7-carboxamido)-4-((R)-3-(2-(5,6,7,8-tetrahydro-1,8-naphthyridin-2-yl)ethyl)pyrrolidin-1-yl)butanoic acid,
(R)-2-(1H-indazole-7-carboxamido)-4-((S)-3-(2-(5,6,7,8-tetrahydro-1,8-naphthyridin-2-yl)ethyl)pyrrolidin-1-yl)butanoic acid,
2-(1-methyl-1H-indazole-4-carboxamido)-4-(3-(2-(5,6,7,8-tetrahydro-1,8-naphthyridin-2-yl)ethyl)pyrrolidin-1-yl)butanoic acid,
(S)-2-(1-methyl-1H-indazole-4-carboxamido)-4-((R)-3-(2-(5,6,7,8-tetrahydro-1,8-naphthyridin-2-yl)ethyl)pyrrolidin-1-yl)butanoic acid,
(S)-2-(1-methyl-1H-indazole-4-carboxamido)-4-((S)-3-(2-(5,6,7,8-tetrahydro-1,8-naphthyridin-2-yl)ethyl)pyrrolidin-1-yl)butanoic acid,
(R)-2-(1-methyl-1H-indazole-4-carboxamido)-4-((R)-3-(2-(5,6,7,8-tetrahydro-1,8-naphthyridin-2-yl)ethyl)pyrrolidin-1-yl)butanoic acid,
(R)-2-(1-methyl-1H-indazole-4-carboxamido)-4-((S)-3-(2-(5,6,7,8-tetrahydro-1,8-naphthyridin-2-yl)ethyl)pyrrolidin-1-yl)butanoic acid,
2-(1-methyl-1H-indazole-7-carboxamido)-4-(3-(2-(5,6,7,8-tetrahydro-1,8-naphthyridin-2-yl)ethyl)pyrrolidin-1-yl)butanoic acid,
(S)-2-(1-methyl-1H-indazole-7-carboxamido)-4-((R)-3-(2-(5,6,7,8-tetrahydro-1,8-naphthyridin-2-yl)ethyl)pyrrolidin-1-yl)butanoic acid,
(S)-2-(1-methyl-1H-indazole-7-carboxamido)-4-((S)-3-(2-(5,6,7,8-tetrahydro-1,8-naphthyridin-2-yl)ethyl)pyrrolidin-1-yl)butanoic acid,
(R)-2-(1-methyl-1H-indazole-7-carboxamido)-4-((R)-3-(2-(5,6,7,8-tetrahydro-1,8-naphthyridin-2-yl)ethyl)pyrrolidin-1-yl)butanoic acid,
(R)-2-(1-methyl-1H-indazole-7-carboxamido)-4-((S)-3-(2-(5,6,7,8-tetrahydro-1,8-naphthyridin-2-yl)ethyl)pyrrolidin-1-yl)butanoic acid,
2-(1-(difluoromethyl)-1H-indazole-6-carboxamido)-4-(3-(2-(5,6,7,8-tetrahydro-1,8-naphthyridin-2-yl)ethyl)pyrrolidin-1-yl)butanoic acid,
(S)-2-(1-(difluoromethyl)-1H-indazole-6-carboxamido)-4-((R)-3-(2-(5,6,7,8-tetrahydro-1,8-naphthyridin-2-yl)ethyl)pyrrolidin-1-yl)butanoic acid,
(S)-2-(1-(difluoromethyl)-1H-indazole-6-carboxamido)-4-((S)-3-(2-(5,6,7,8-tetrahydro-1,8-naphthyridin-2-yl)ethyl)pyrrolidin-1-yl)butanoic acid,
(R)-2-(1-(difluoromethyl)-1H-indazole-6-carboxamido)-4-((R)-3-(2-(5,6,7,8-tetrahydro-1,8-naphthyridin-2-yl)ethyl)pyrrolidin-1-yl)butanoic acid,
(R)-2-(1-(difluoromethyl)-1H-indazole-6-carboxamido)-4-((S)-3-(2-(5,6,7,8-tetrahydro-1,8-naphthyridin-2-yl)ethyl)pyrrolidin-1-yl)butanoic acid,
2-(1-(difluoromethyl)-1H-indazole-5-carboxamido)-4-(3-(2-(5,6,7,8-tetrahydro-1,8-naphthyridin-2-yl)ethyl)pyrrolidin-1-yl)butanoic acid,
(S)-2-(1-(difluoromethyl)-1H-indazole-5-carboxamido)-4-((R)-3-(2-(5,6,7,8-tetrahydro-1,8-naphthyridin-2-yl)ethyl)pyrrolidin-1-yl)butanoic acid,
(S)-2-(1-(difluoromethyl)-1H-indazole-5-carboxamido)-4-((S)-3-(2-(5,6,7,8-tetrahydro-1,8-naphthyridin-2-yl)ethyl)pyrrolidin-1-yl)butanoic acid,
(R)-2-(1-(difluoromethyl)-1H-indazole-5-carboxamido)-4-((R)-3-(2-(5,6,7,8-tetrahydro-1,8-naphthyridin-2-yl)ethyl)pyrrolidin-1-yl)butanoic acid,
(R)-2-(1-(difluoromethyl)-1H-indazole-5-carboxamido)-4-((S)-3-(2-(5,6,7,8-tetrahydro-1,8-naphthyridin-2-yl)ethyl)pyrrolidin-1-yl)butanoic acid,
2-(benzo[d]oxazole-5-carboxamido)-4-(3-(2-(5,6,7,8-tetrahydro-1,8-naphthyridin-2-yl)ethyl)pyrrolidin-1-yl)butanoic acid,
(S)-2-(benzo[d]oxazole-5-carboxamido)-4-((R)-3-(2-(5,6,7,8-tetrahydro-1,8-naphthyridin-2-yl)ethyl)pyrrolidin-1-yl)butanoic acid,
(S)-2-(benzo[d]oxazole-5-carboxamido)-4-((S)-3-(2-(5,6,7,8-tetrahydro-1,8-naphthyridin-2-yl)ethyl)pyrrolidin-1-yl)butanoic acid,
(R)-2-(benzo[d]oxazole-5-carboxamido)-4-((R)-3-(2-(5,6,7,8-tetrahydro-1,8-naphthyridin-2-yl)ethyl)pyrrolidin-1-yl)butanoic acid,
(R)-2-(benzo[d]oxazole-5-carboxamido)-4-((S)-3-(2-(5,6,7,8-tetrahydro-1,8-naphthyridin-2-yl)ethyl)pyrrolidin-1-yl)butanoic acid,
(S)-2-(3-formamido-4-hydroxybenzamido)-4-((R)-3-(2-(5,6,7,8-tetrahydro-1,8-naphthyridin-2-yl)ethyl)pyrrolidin-1-yl)butanoic acid,
(S)-2-(4,4-difluorocyclohexane-1-carboxamido)-4-(4-(5,6,7,8-tetrahydro-1,8-naphthyridine-2-carboxamido)piperidin-1-yl)butanoic acid,
(S)-2-(4,4-difluorocyclohexane-1-carboxamido)-4-(4-(((5,6,7,8-tetrahydro-1,8-naphthyridin-2-yl)methyl)amino)piperidin-1-yl)butanoic acid,
(S)-2-(1H-indazole-4-carboxamido)-4-((R)-3-(2-(5,6,7,8-tetrahydro-1,8-naphthyridin-2-yl)ethyl)pyrrolidin-1-yl)butanoic acid,
(S)-2-((S)-1-benzylpyrrolidine-2-carboxamido)-4-((R)-3-(2-(5,6,7,8-tetrahydro-1,8-naphthyridin-2-yl)ethyl)pyrrolidin-1-yl)butanoic acid,
(S)-2-(2-methyl-2-(pyridin-3-yl)propanamido)-4-((R)-3-(2-(5,6,7,8-tetrahydro-1,8-naphthyridin-2-yl)ethyl)pyrrolidin-1-yl)butanoic acid,
(S)-4-((R)-3-(2-(5,6,7,8-tetrahydro-1,8-naphthyridin-2-yl)ethyl)pyrrolidin-1-yl)-2-(tetrahydro-2H-pyran-4-carboxamido)butanoic acid,
(2S)-2-benzamido-4-(3,3-difluoro-4-(2-(5,6,7,8-tetrahydro-1,8-naphthyridin-2-yl)ethyl)pyrrolidin-1-yl)butanoic acid,
(2S)-2-((tert-butoxycarbonyl)amino)-4-(3,3-difluoro-5-(2-(5,6,7,8-tetrahydro-1,8-naphthyridin-2-yl)ethyl)piperidin-1-yl)butanoic acid,
(2S)-2-benzamido-4-(3,3-difluoro-5-(2-(5,6,7,8-tetrahydro-1,8-naphthyridin-2-yl)ethyl)piperidin-1-yl)butanoic acid,
(2S)-4-(3,3-difluoro-5-(2-(5,6,7,8-tetrahydro-1,8-naphthyridin-2-yl)ethyl)piperidin-1-yl)-2-(3-(3,5-dimethyl-1H-pyrazol-1-yl)benzamido)butanoic acid,
(S)-2-((S)-1-phenylpyrrolidine-2-carboxamido)-4-((R)-3-(2-(5,6,7,8-tetrahydro-1,8-naphthyridin-2-yl)ethyl)pyrrolidin-1-yl)butanoic acid,
(S)-2-(2-methyl-2-phenylpropanamido)-4-((R)-3-(2-(5,6,7,8-tetrahydro-1,8-naphthyridin-2-yl)ethyl)pyrrolidin-1-yl)butanoic acid, (S)-2-(2,2-dimethyl-3-phenylpropanamido)-4-((R)-3-(2-(5,6,7,8-tetrahydro-1,8-naphthyridin-2-yl)ethyl)pyrrolidin-1-yl)butanoic acid, (S)-2-((S)-1-(pyridin-2-yl)pyrrolidine-3-carboxamido)-4-((R)-3-(2-(5,6,7,8-tetrahydro-1,8-naphthyridin-2-yl)ethyl)pyrrolidin-1-yl)butanoic acid, (S)-2-((R)-1-(pyridin-2-yl)pyrrolidine-3-carboxamido)-4-((R)-3-(2-(5,6,7,8-tetrahydro-1,8-naphthyridin-2-yl)ethyl)pyrrolidin-1-yl)butanoic acid, (S)-2-(3-cyanobenzamido)-4-((R)-3-(2-(5,6,7,8-tetrahydro-1,8-naphthyridin-2-yl)ethyl)pyrrolidin-1-yl)butanoic acid, (S)-2-(1-methyl-1H-pyrazole-5-carboxamido)-4-((R)-3-(2-(5,6,7,8-tetrahydro-1,8-naphthyridin-2-yl)ethyl)pyrrolidin-1-yl)butanoic acid, (S)-2-(pyrazine-2-carboxamido)-4-((R)-3-(2-(5,6,7,8-tetrahydro-1,8-naphthyridin-2-yl)ethyl)pyrrolidin-1-yl)butanoic acid, (S)-4-((R)-3-(2-(5,6,7,8-tetrahydro-1,8-naphthyridin-2-yl)ethyl)pyrrolidin-1-yl)-2-(thiophene-2-carboxamido)butanoic acid, (S)-2-benzamido-4-((R)-3-fluoro-3-(2-(5,6,7,8-tetrahydro-1,8-naphthyridin-2-yl)ethyl)piperidin-1-yl)butanoic acid, (S)-2-(3-(3,5-dimethyl-1H-pyrazol-1-yl)benzamido)-4-((R)-3-fluoro-3-(2-(5,6,7,8-tetrahydro-1,8-naphthyridin-2-yl)ethyl)piperidin-1-yl)butanoic acid, (2S)-2-benzamido-4-(3-(2-(5,6,7,8-tetrahydro-1,8-naphthyridin-2-yl)ethyl)piperidin-1-yl)butanoic acid, (S)-4-((R)-3-(2-(5,6,7,8-tetrahydro-1,8-naphthyridin-2-yl)ethyl)pyrrolidin-1-yl)-2-(3-(thiophen-2-yl)benzamido)butanoic acid, (S)-2-([1,1'-biphenyl]-3-carboxamido)-4-((R)-3-(2-(5,6,7,8-tetrahydro-1,8-naphthyridin-2-yl)ethyl)pyrrolidin-1-yl)butanoic acid, (S)-2-(3-(1-methyl-1H-pyrazol-5-yl)benzamido)-4-((R)-3-(2-(5,6,7,8-tetrahydro-1,8-naphthyridin-2-yl)ethyl)pyrrolidin-1-yl)butanoic acid, (S)-2-(3-(1-methyl-1H-pyrazol-4-yl)benzamido)-4-((R)-3-(2-(5,6,7,8-tetrahydro-1,8-naphthyridin-2-yl)ethyl)pyrrolidin-1-yl)butanoic acid, (S)-2-(3-(oxazol-2-yl)benzamido)-4-((R)-3-(2-(5,6,7,8-tetrahydro-1,8-naphthyridin-2-yl)ethyl)pyrrolidin-1-yl)butanoic acid, (S)-2-(1-isopropyl-1H-indazole-4-carboxamido)-4-((R)-3-(2-(5,6,7,8-tetrahydro-1,8-naphthyridin-2-yl)ethyl)pyrrolidin-1-yl)butanoic acid, (S)-2-(1-isobutyl-1H-indazole-4-carboxamido)-4-((R)-3-(2-(5,6,7,8-tetrahydro-1,8-naphthyridin-2-yl)ethyl)pyrrolidin-1-yl)butanoic acid, (S)-2-(2-chloro-3-fluorobenzamido)-4-((R)-3-fluoro-3-(2-(5,6,7,8-tetrahydro-1,8-naphthyridin-2-yl)ethyl)piperidin-1-yl)butanoic acid, (S)-2-(2,6-dichlorobenzamido)-4-((S)-3-fluoro-3-(2-(5,6,7,8-tetrahydro-1,8-naphthyridin-2-yl)ethyl)pyrrolidin-1-yl)butanoic acid, (S)-2-(2,6-dichlorobenzamido)-4-((R)-3-fluoro-3-(2-(5,6,7,8-tetrahydro-1,8-naphthyridin-2-yl)ethyl)pyrrolidin-1-yl)butanoic acid, (S)-4-((R)-3-(2-(5,6,7,8-tetrahydro-1,8-naphthyridin-2-yl)ethyl)pyrrolidin-1-yl)-2-(3-(thiazol-4-yl)benzamido)butanoic acid, (S)-4-((R)-3-(2-(5,6,7,8-tetrahydro-1,8-naphthyridin-2-yl)ethyl)pyrrolidin-1-yl)-2-(3-(thiazol-5-yl)benzamido)butanoic acid, (S)-2-(2,3-difluorobenzamido)-4-((R)-3-(2-(5,6,7,8-tetrahydro-1,8-naphthyridin-2-yl)ethyl)pyrrolidin-1-yl)butanoic acid, (S)-2-(3-(tert-butyl)benzamido)-4-((R)-3-(2-(5,6,7,8-tetrahydro-1,8-naphthyridin-2-yl)ethyl)pyrrolidin-1-yl)butanoic acid, (S)-2-(1-methyl-1H-pyrazole-4-carboxamido)-4-((R)-3-(2-(5,6,7,8-tetrahydro-1,8-naphthyridin-2-yl)ethyl)pyrrolidin-1-yl)butanoic acid, (S)-2-(pyrimidine-4-carboxamido)-4-((R)-3-(2-(5,6,7,8-tetrahydro-1,8-naphthyridin-2-yl)ethyl)pyrrolidin-1-yl)butanoic acid, (S)-2-(2-isopropyl-2H-indazole-4-carboxamido)-4-((R)-3-(2-(5,6,7,8-tetrahydro-1,8-naphthyridin-2-yl)ethyl)pyrrolidin-1-yl)butanoic acid, (S)-2-(2-isobutyl-2H-indazole-4-carboxamido)-4-((R)-3-(2-(5,6,7,8-tetrahydro-1,8-naphthyridin-2-yl)ethyl)pyrrolidin-1-yl)butanoic acid, (S)-2-((S)-1-pentanoylpiperidine-2-carboxamido)-4-((R)-3-(2-(5,6,7,8-tetrahydro-1,8-naphthyridin-2-yl)ethyl)pyrrolidin-1-yl)butanoic acid, (S)-2-((S)-1-(cyclobutanecarbonyl)piperidine-2-carboxamido)-4-((R)-3-(2-(5,6,7,8-tetrahydro-1,8-naphthyridin-2-yl)ethyl)pyrrolidin-1-yl)butanoic acid, (S)-2-(2-(2-chlorophenyl)acetamido)-4-((R)-3-(2-(5,6,7,8-tetrahydro-1,8-naphthyridin-2-yl)ethyl)pyrrolidin-1-yl)butanoic acid, (S)-2-(3-fluoro-5-(trifluoromethyl)benzamido)-4-((R)-3-(2-(5,6,7,8-tetrahydro-1,8-naphthyridin-2-yl)ethyl)pyrrolidin-1-yl)butanoic acid, (S)-2-((S)-1-(2-hydroxy-2-methylpropyl)pyrrolidine-2-carboxamido)-4-((R)-3-(2-(5,6,7,8-tetrahydro-1,8-naphthyridin-2-yl)ethyl)pyrrolidin-1-yl)butanoic acid, (S)-2-((R)-1-pentanoylpiperidine-3-carboxamido)-4-((R)-3-(2-(5,6,7,8-tetrahydro-1,8-naphthyridin-2-yl)ethyl)pyrrolidin-1-yl)butanoic acid, (S)-2-((R)-1-pivaloylpiperidine-3-carboxamido)-4-((R)-3-(2-(5,6,7,8-tetrahydro-1,8-naphthyridin-2-yl)ethyl)pyrrolidin-1-yl)butanoic acid, (S)-2-((R)-1-(methoxycarbonyl)piperidine-3-carboxamido)-4-((R)-3-(2-(5,6,7,8-tetrahydro-1,8-naphthyridin-2-yl)ethyl)pyrrolidin-1-yl)butanoic acid, (S)-2-((S)-1-benzylazetidine-2-carboxamido)-4-((R)-3-(2-(5,6,7,8-tetrahydro-1,8-naphthyridin-2-yl)ethyl)pyrrolidin-1-yl)butanoic acid, (S)-2-(1-methyl-3-phenyl-1H-indazole-7-carboxamido)-4-((R)-3-(2-(5,6,7,8-tetrahydro-1,8-naphthyridin-2-yl)ethyl)pyrrolidin-1-yl)butanoic acid, (R)-2-([1,1'-biphenyl]-3-carboxamido)-4-((R)-3-(2-(5,6,7,8-tetrahydro-1,8-naphthyridin-2-yl)ethyl)pyrrolidin-1-yl)butanoic acid, (R)-4-((R)-3-(2-(5,6,7,8-tetrahydro-1,8-naphthyridin-2-yl)ethyl)pyrrolidin-1-yl)-2-(3-(thiazol-5-yl)benzamido)butanoic acid, (R)-4-((R)-3-(2-(5,6,7,8-tetrahydro-1,8-naphthyridin-2-yl)ethyl)pyrrolidin-1-yl)-2-(3-(thiazol-4-yl)benzamido)butanoic acid, (R)-2-(3-(1-methyl-1H-pyrazol-5-yl)benzamido)-4-((R)-3-(2-(5,6,7,8-tetrahydro-1,8-naphthyridin-2-yl)ethyl)pyrrolidin-1-yl)butanoic acid, (R)-2-(3-(1-methyl-1H-pyrazol-4-yl)benzamido)-4-((R)-3-(2-(5,6,7,8-tetrahydro-1,8-naphthyridin-2-yl)ethyl)pyrrolidin-1-yl)butanoic acid, (R)-2-(3-(oxazol-2-yl)benzamido)-4-((R)-3-(2-(5,6,7,8-tetrahydro-1,8-naphthyridin-2-yl)ethyl)pyrrolidin-1-yl)butanoic acid, (S)-2-((S)-4-benzylmorpholine-3-carboxamido)-4-((R)-3-(2-(5,6,7,8-tetrahydro-1,8-naphthyridin-2-yl)ethyl)pyrrolidin-1-yl)butanoic acid, (S)-2-((S)-1-(pyrimidin-2-ylmethyl)pyrrolidine-2-carboxamido)-4-((R)-3-(2-(5,6,7,8-tetrahydro-1,8-naphthyridin-2-yl)ethyl)pyrrolidin-1-yl)butanoic acid, (S)-2-((S)-1-(cyclopropylmethyl)pyrrolidine-2-carboxamido)-4-((R)-3-(2-(5,6,7,8-tetrahydro-1,8-naphthyridin-2-yl)ethyl)pyrrolidin-1-yl)butanoic acid, (S)-2-((S)-1-(cyclobutylmethyl)pyrrolidine-2-carboxamido)-4-((R)-3-(2-(5,6,7,8-tetrahydro-1,8-naphthyridin-2-yl)ethyl)pyrrolidin-1-yl)butanoic acid, (S)-2-((S)-1-benzylpiperidine-2-carboxamido)-4-((R)-3-(2-(5,6,7,8-tetrahydro-1,8-naphthyridin-2-yl)ethyl)pyrrolidin-1-yl)butanoic acid, (S)-2-(2-ethylbutanamido)-4-((R)-3-fluoro-3-(2-(5,6,7,8-tetrahydro-1,8-naphthyridin-2-yl)ethyl)piperidin-1-yl)butanoic acid, (S)-2-(2-ethylbutanamido)-4-((R)-3-(2-(5,6,7,8-tetrahydro-1,8-naphthyridin-2-yl)ethyl)pyrrolidin-1-yl)butanoic acid, (S)-4-((R)-3-fluoro-3-(2-(5,6,7,8-tetrahydro-1,8-naphthyridin-2-yl)ethyl)piperidin-1-yl)-2-(3-morpholinobenzamido)butanoic acid, (S)-2-(3,5-difluorobenzamido)-4-((R)-3-fluoro-3-(2-(5,6,7,8-tetrahydro-1,8-naphthyridin-2-yl)ethyl)piperidin-1-yl)butanoic acid, (S)-2-(3-(1,3-dimethyl-1H-pyrazol-4-yl)-1-methyl-1H-indazole-7-carboxamido)-4-((R)-3-(2-(5,6,7,8-tetrahydro-1,8-naphthyridin-2-yl)ethyl)pyrrolidin-1-yl)butanoic acid, (S)-2-((S)-1-(pyridin-3-ylmethyl)pyrrolidine-2-carboxamido)-4-((R)-3-(2-(5,6,7,8-tetrahydro-1,8-naphthyridin-2-yl)ethyl)pyrrolidin-1-yl)butanoic acid, (S)-4-((R)-3-fluoro-3-(2-(5,6,7,8-tetrahydro-1,8-naphthyridin-2-yl)ethyl)piperidin-1-yl)-2-(3-(2-methoxyethoxy)benzamido)butanoic acid, (S)-2-(2,6-dichlorobenzamido)-4-((R)-3-fluoro-3-(2-(5,6,7,8-tetrahydro-1,8-naphthyridin-2-yl)ethyl)piperidin-1-yl)butanoic acid, (S)-2-(1-methyl-3-(1-methyl-1H-pyrazol-4-yl)-1H-indazole-7-carboxamido)-4-((R)-3-(2-(5,6,7,8-tetrahydro-1,8-naphthyridin-2-yl)ethyl)pyrrolidin-1-yl)butanoic acid, (S)-2-(2-chloro-3-fluorobenzamido)-4-((S)-3-fluoro-3-(2-(5,6,7,8-tetrahydro-1,8-naphthyridin-2-yl)ethyl)piperidin-1-yl)butanoic acid, (S)-2-(3,5-difluorobenzamido)-4-((S)-3-fluoro-3-(2-(5,6,7,8-tetrahydro-1,8-naphthyridin-2-yl)ethyl)piperidin-1-yl)butanoic acid, (S)-4-((R)-3-fluoro-3-(2-(5,6,7,8-tetrahydro-1,8-naphthyridin-2-yl)ethyl)piperidin-1-yl)-2-(3-fluoro-5-(trifluoromethyl)benzamido)butanoic acid, (S)-4-((R)-3-fluoro-3-(2-(5,6,7,8-tetrahydro-1,8-naphthyridin-2-yl)ethyl)piperidin-1-yl)-2-(1-methyl-1H-indazole-6-carboxamido)butanoic acid, (S)-2-(4,4-difluorocyclohexane-1-carboxamido)-4-((R)-3-fluoro-3-(2-(5,6,7,8-tetrahydro-1,8-naphthyridin-2-yl)ethyl)piperidin-1-yl)butanoic acid, (S)-2-(2-ethylbutanamido)-4-((S)-3-fluoro-3-(2-(5,6,7,8-tetrahydro-1,8-naphthyridin-2-yl)ethyl)piperidin-1-yl)butanoic acid, (S)-2-(4,4-difluorocyclohexane-1-carboxamido)-4-((S)-3-fluoro-3-(2-(5,6,7,8-tetrahydro-1,8-naphthyridin-2-yl)ethyl)piperidin-1-yl)butanoic acid, (S)-4-((S)-3-fluoro-3-(2-(5,6,7,8-tetrahydro-1,8-naphthyridin-2-yl)ethyl)piperidin-1-yl)-2-(1-methyl-1H-indazole-6-carboxamido)butanoic acid, (S)-2-((tert-butoxycarbonyl)amino)-4-((R)-3-((5,6,7,8-tetrahydro-1,8-naphthyridin-2-yl)methoxy)pyrrolidin-1-yl)butanoic acid, (S)-2-benzamido-4-((R)-3-((5,6,7,8-tetrahydro-1,8-naphthyridin-2-yl)methoxy)pyrrolidin-1-yl)butanoic acid, (S)-2-(3-(3,5-dimethyl-1H-pyrazol-1-yl)benzamido)-4-((R)-3-((5,6,7,8-tetrahydro-1,8-naphthyridin-2-yl)methoxy)pyrrolidin-1-yl)butanoic acid, (S)-2-(2,6-dichlorobenzamido)-4-((R)-3-(2-(5,6,7,8-tetrahydro-1,8-naphthyridin-2-yl)ethoxy)pyrrolidin-1-yl)butanoic acid, (S)-2-(2,6-dichlorobenzamido)-4-(3-(2-(5,6,7,8-tetrahydro-1,8-naphthyridin-2-yl)ethoxy)azetidin-1-yl)butanoic acid, (S)-4-((S)-4-acetyl-3-(2-(5,6,7,8-tetrahydro-1,8-naphthyridin-2-yl)ethyl)piperazin-1-yl)-2-benzamidobutanoic acid, (S)-4-((R)-3-(2-(5,6,7,8-tetrahydro-1,8-naphthyridin-2-yl)ethoxy)pyrrolidin-1-yl)-2-(tetrahydro-2H-pyran-4-carboxamido)butanoic acid, (S)-2-(2-methyl-2-phenylpropanamido)-4-((R)-3-(2-(5,6,7,8-tetrahydro-1,8-naphthyridin-2-yl)ethoxy)pyrrolidin-1-yl)butanoic acid, (S)-2-(2,2-dimethyl-3-phenylpropanamido)-4-((R)-3-(2-(5,6,7,8-tetrahydro-1,8-naphthyridin-2-yl)ethoxy)pyrrolidin-1-yl)butanoic acid, (S)-2-(2-methyl-2-phenylpropanamido)-4-(3-(2-(5,6,7,8-tetrahydro-1,8-naphthyridin-2-yl)ethoxy)azetidin-1-yl)butanoic acid, (S)-2-((S)-1-benzylpyrrolidine-2-carboxamido)-4-((R)-3-(2-(5,6,7,8-tetrahydro-1,8-naphthyridin-2-yl)ethoxy)pyrrolidin-1-yl)butanoic acid, (S)-2-(2-methyl-2-(pyridin-3-yl)propanamido)-4-((R)-3-(2-(5,6,7,8-tetrahydro-1,8-naphthyridin-2-yl)ethoxy)pyrrolidin-1-yl)butanoic acid, (S)-2-((S)-1-benzylpyrrolidine-2-carboxamido)-4-(3-(2-(5,6,7,8-tetrahydro-1,8-naphthyridin-2-yl)ethoxy)azetidin-1-yl)butanoic acid, (S)-4-(3-(2-(5,6,7,8-tetrahydro-1,8-naphthyridin-2-yl)ethoxy)azetidin-1-yl)-2-(tetrahydro-2H-pyran-4-carboxamido)butanoic acid, (S)-2-((R)-1-(pyridin-2-yl)pyrrolidine-3-carboxamido)-4-((R)-3-(2-(5,6,7,8-tetrahydro-1,8-naphthyridin-2-yl)ethoxy)pyrrolidin-1-yl)butanoic acid, (S)-2-((S)-1-(pyridin-2-yl)pyrrolidine-3-carboxamido)-4-((R)-3-(2-(5,6,7,8-tetrahydro-1,8-naphthyridin-2-yl)ethoxy)pyrrolidin-1-yl)butanoic acid, (S)-2-((S)-1-phenylpyrrolidine-2-carboxamido)-4-(3-(2-(5,6,7,8-tetrahydro-1,8-naphthyridin-2-yl)ethoxy)azetidin-1-yl)butanoic acid, (S)-2-(2-methyl-2-(pyridin-3-yl)propanamido)-4-(3-(2-(5,6,7,8-tetrahydro-1,8-naphthyridin-2-yl)ethoxy)azetidin-1-yl)butanoic acid, (S)-2-((S)-1-phenylpyrrolidine-2-carboxamido)-4-(3-(2-(5,6,7,8-tetrahydro-1,8-naphthyridin-2-yl)ethyl)azetidin-1-yl)butanoic acid, (S)-2-(2,2-dimethyl-3-phenylpropanamido)-4-(3-(2-(5,6,7,8-tetrahydro-1,8-naphthyridin-2-yl)ethoxy)azetidin-1-yl)butanoic acid, (S)-2-((R)-1-(pyridin-2-yl)pyrrolidine-3-carboxamido)-4-(3-(2-(5,6,7,8-tetrahydro-1,8-naphthyridin-2-yl)ethoxy)azetidin-1-yl)butanoic acid, (S)-2-((S)-1-(pyridin-2-yl)pyrrolidine-3-carboxamido)-4-(3-(2-(5,6,7,8-tetrahydro-1,8-naphthyridin-2-yl)ethoxy)azetidin-1-yl)butanoic acid, (S)-2-((S)-1-phenylpyrrolidine-2-carboxamido)-4-((R)-3-(2-(5,6,7,8-tetrahydro-1,8-naphthyridin-2-yl)ethoxy)pyrrolidin-1-yl)butanoic acid, (2S)-2-(1-(2-hydroxy-2-methylpropyl)pyrrolidine-2-carboxamido)-4-(3-(2-(5,6,7,8-tetrahydro-1,8-naphthyridin-2-yl)ethoxy)azetidin-1-yl)butanoic acid, (2S)-2-(1-benzylpyrrolidine-2-carboxamido)-4-(3-(2-(5,6,7,8-tetrahydro-1,8-naphthyridin-2-yl)ethyl)azetidin-1-yl)butanoic acid, (S)-2-(2-methyl-2-phenylpropanamido)-4-(3-(2-(5,6,7,8-tetrahydro-1,8-naphthyridin-2-yl)ethyl)azetidin-1-yl)butanoic acid, (S)-2-(2,2-dimethyl-3-phenylpropanamido)-4-(3-(2-(5,6,7,8-tetrahydro-1,8-naphthyridin-2-yl)ethyl)azetidin-1-yl)butanoic acid, (S)-2-((S)-1-(pyridin-2-yl)pyrrolidine-3-carboxamido)-4-(3-(2-(5,6,7,8-tetrahydro-1,8-naphthyridin-2-yl)ethyl)azetidin-1-yl)butanoic acid, (S)-2-(2,6-dichlorobenzamido)-4-(3-(2-(5,6,7,8-tetrahydro-1,8-naphthyridin-2-yl)ethyl)azetidin-1-yl)butanoic acid, (S)-2-(3-fluoro-5-(trifluoromethyl)benzamido)-4-((1R,2R,4S)-2-(2-(5,6,7,8-tetrahydro-1,8-naphthyridin-2-yl)ethyl)-7-azabicyclo[2.2.1]heptan-7-yl)butanoic acid, (S)-2-(3-fluoro-5-(trifluoromethyl)benzamido)-4-((1R,2R,4S)-2-(2-(5,6,7,8-tetrahydro-1,8-naphthyridin-2-yl)ethyl)-7-azabicyclo[2.2.1]heptan-7-yl)butanoic acid, (S)-2-((S)-1-(2-hydroxy-2-methylpropyl)pyrrolidine-2-carboxamido)-4-((R)-3-(2-(5,6,7,8-tetrahydro-1,8-naphthyridin-2-yl)ethoxy)pyrrolidin-1-yl)butanoic acid, (S)-2-((S)-1-benzylpyrrolidine-2-carboxamido)-4-(3-(2-(5,6,7,8-tetrahydro-1,8-naphthyridin-2-yl)ethyl)azetidin-1-yl)butanoic acid, (S)-2-(2-methyl-2-(pyridin-3-yl)propanamido)-4-(3-(2-(5,6,7,8-tetrahydro-1,8-naphthyridin-2-yl)ethyl)azetidin-1-yl)butanoic acid, (S)-2-(2-ethylbutanamido)-4-((1R,2R,4S)-2-(2-(5,6,7,8-tetrahydro-1,8-naphthyridin-2-yl)ethyl)-7-azabicyclo[2.2.1]heptan-7-yl)butanoic acid, (S)-2-(2,6-dichlorobenzamido)-4-((S)-3-(2-(5,6,7,8-tetrahydro-1,8-naphthyridin-2-yl)ethyl)pyrrolidin-1-yl)butanoic acid, or (R)-2-(2,6-dichlorobenzamido)-4-((S)-3-(2-(5,6,7,8-tetrahydro-1,8-naphthyridin-2-yl)ethyl)pyrrolidin-1-yl)butanoic acid;

or a salt thereof.

28. A pharmaceutical composition comprising a compound of claim 1, or a salt thereof, and a pharmaceutically acceptable carrier or excipient.

29. A method of treating a fibrotic disease in an individual in need thereof comprising administering a compound of claim 1 or a pharmaceutically acceptable salt thereof.

30. The method of claim 29, wherein the fibrotic disease is pulmonary fibrosis, liver fibrosis, skin fibrosis, cardiac fibrosis, kidney fibrosis, gastrointestinal fibrosis, primary sclerosing cholangitis, or biliary fibrosis.

31. A kit comprising a compound of claim 1, or a pharmaceutically acceptable salt thereof.

32. The kit of claim 31, further comprising instructions for the treatment of a fibrotic disease.

33. A method of inhibiting αvβ6 integrin in an individual comprising administering a compound of claim 1 or a pharmaceutically acceptable salt thereof.

34. A method of inhibiting TGFβ activation in a cell comprising administering to the cell a compound of claim 1 or a pharmaceutically acceptable salt thereof.

* * * * *